US012109310B2

(12) United States Patent
Valadi et al.

(10) Patent No.: US 12,109,310 B2
(45) Date of Patent: Oct. 8, 2024

(54) EXOSOME EXTRACELLULAR VESICLES AND METHODS OF USE

(71) Applicants: AstraZeneca AB; Hadi Valadi, Gothenburg (SE)

(72) Inventors: Hadi Valadi, Gothenburg (SE); Lennart Lindfors, Mölndal (SE)

(73) Assignees: Hadi Valadi, Gothenburg (SE); Astraeneca AB, Sodertalje (SE)

( * ) Notice: Subject to any disclaimer, the term of this patent is extended or adjusted under 35 U.S.C. 154(b) by 920 days.

(21) Appl. No.: 16/972,190

(22) PCT Filed: Jun. 27, 2019

(86) PCT No.: PCT/EP2019/067232
§ 371 (c)(1),
(2) Date: Dec. 4, 2020

(87) PCT Pub. No.: WO2020/002540
PCT Pub. Date: Jan. 2, 2020

(65) Prior Publication Data
US 2021/0315819 A1    Oct. 14, 2021

Related U.S. Application Data

(60) Provisional application No. 62/691,348, filed on Jun. 28, 2018.

(51) Int. Cl.
*A61K 9/127*     (2006.01)
*A61K 31/7115*   (2006.01)
(52) U.S. Cl.
CPC ........ *A61K 9/1272* (2013.01); *A61K 31/7115* (2013.01)

(58) Field of Classification Search
CPC .................. A61K 9/1272; A61K 31/7115
See application file for complete search history.

(56) References Cited

U.S. PATENT DOCUMENTS

2013/0156849 A1   6/2013   De Fougerolles et al.
2016/0354313 A1   12/2016  De Beer et al.
2021/0290556 A1*  9/2021   Williams ............... C12N 15/88

FOREIGN PATENT DOCUMENTS

EP          3292861 A1    3/2018

OTHER PUBLICATIONS

International Application No. PCT/EP2019/067232 International Search Report and Written Opinion dated Oct. 9, 2019.
Biscans et al. "Hydrophobicity of Lipid-Conjugated siRNAs Predicts Productive Loading to Small Extracellular Vesicles." Molecular therapy: the journal of the American Society of Gene and Cell Therapy, Jun. 2018, vol. 26, No. 6, pp. 1520-1528.

(Continued)

*Primary Examiner* — Jennifer Wecker
*Assistant Examiner* — Kathryn Elizabeth Limbaugh

(57) ABSTRACT

Exosomes comprising a modified RNA are disclosed. Aspects of the disclosure further relate to methods and compositions for using exosomes comprising a modified RNA. In certain aspects, the exosomes disclosed herein may be useful in delivering a modified RNA to a cell. In certain aspects, the exosomes disclosed herein may be useful in treating or preventing a disorder in a subject. Methods and compositions for producing the disclosed exosomes are also provided.

16 Claims, 89 Drawing Sheets

Specification includes a Sequence Listing.

(56) References Cited

OTHER PUBLICATIONS

Lin et al. "Exosome-Liposome Hybrid Nanoparticles Deliver CRISPR/Cas9 System in MSCs." Advanced Science, 2018, vol. 5, 1700611, pp. 1-9.
Usman et al. "Efficient RNA drug delivery using red blood cell extracellular vesicles." Nature Communications, 2018, 9;2359.
Wahlgren et al. "Plasma exosomes can deliver exogenous short interfering RNA to monocytes and lymphocytes." Nucleic Acids Research, 2012, vol. 40, No. 17, e130.
Shtam et al. "Exosomes are natural carriers of exogenous siRNA to human cells in vitro." Cell Communication and Signaling, 2013, 11: 88.
El-Andaloussi et al. "Exosome-mediated delivery of siRNA in vitro and in vivo." Nature Protocols, 2012, vol. 7, No. 12, pp. 2112-2126.
Alvarez-Erviti et al. "Delivery of siRNA to the mouse brain by systemic injection of targeted exosomes." Nature Biotechnology, Apr. 2011, vol. 29, No. 4, pp. 341-345.
Ohno et al. "Systemically injected exosomes targeted to EGFR deliver antitumor microRNA to breast cancer cells." Molecular Therapy, Jan. 2013, vol. 21, No. 1, pp. 185-191.
Fatima et al. "Long Distance Metabolic Regulation through Adipose-Derived Circulating Exosomal miRNAs: A Trail for RNA-Based Therapies?" Frontiers in Physiology, Aug. 2017, vol. 8, Article 545.
Kamerkar et al. "Exosomes facilitate therapeutic targeting of oncogenic KRAS in pancreatic cancer." Nature, Jun. 2017, vol. 546.

* cited by examiner

EXOSOME EXTRACELLULAR VESICLES AND METHODS OF USE

The present disclosure relates to exosomes comprising a modified RNA. The present disclosure further relates to methods and compositions for using the exosomes disclosed herein. In certain aspects, the exosomes disclosed herein may be useful in delivering a modified RNA to a cell. In certain aspects, the exosomes disclosed herein may be useful in treating or preventing a disorder in a subject. Methods and compositions for producing the disclosed exosomes are also provided.

RNA is a promising therapeutic molecule for the treatment of various diseases, including cancers, infectious diseases, and inherited genetic conditions (Pardi et al. (2018) Nat Rev Drug Discov. 17(4):261-79; Dunbar et al. (2018) Science 359(6372):eaan4672). RNA therapy generally involves silencing pathological genes using RNA interference (RNAi, e.g., siRNA) or expressing therapeutic proteins by delivering mRNA to cells. To achieve regulatory approval, the vehicles used for RNA delivery should be safe (i.e., non-immunogenic and non-toxic), and capable of efficiently transporting the therapeutic RNA to the cytoplasm of recipient cells.

Known drug carriers, such as lipid nanoparticles (LNPs), facilitate targeted, site-specific delivery of drugs to tissues and cells, thus enhancing their bioavailability. LNPs containing ionizable lipids represent one platform for RNA delivery (Semple et al. (2010) Nat Biotechnol. 28(2):172-6; Patel et al. (2017) Nano Lett. 17(9):5711-8; Rietwyk and Peer (2017) ACS Nano. 11(8):7572-86). However, an obstacle in developing LNPs and other such carriers is the potential immunogenic response associated with components of their formulations.

Despite efforts to minimize the immunogenic response associated with LNPs, such as adding a polyethylene glycol shield to avoid recognition by the mononuclear phagocyte system, LNPs can still evoke an immune response (Kumar et al. (2014) Mol Ther Nucleic Acids 3(e210)). For instance, certain LNP formulations have been shown to be partially toxic to recipient cells, and cause undesirable immune responses in the host (Barros and Gollob (2012) Adv Drug Deliv Rev. 64(15):1730-7; Kulkarni et al. (2017) Nanomedicine 13(4):1377-87).

The immunostimulatory effect of LNPs continues to block their use for safe and effective delivery of therapeutic RNAs. Accordingly, there exists a need to develop alternative vehicles that can effectively deliver RNA to target tissues and cells without triggering an immune response.

Extracellular vesicles (EVs) are a heterogeneous class of nano- and micro-sized vesicles secreted by almost every cell type (Raposo et al. (1996) J Exp Med. 183(3):1161-72; Zitvogel et al. (1998) Nat Med. 4(5):594-600; Nawaz et al. (2016) Stem Cells Int. 2016:1073140). EVs can be detected in most biological fluids, as well as in supernatants of cultured cells (Akers et al. (2015) J Neurooncol. 123(2):205-16; Lasser et al. (2011) J Transl Med. 9:9; Thery et al. (2006) Curr Protoc Cell Biol. Chapter 3: Unit 3.22). During EV biogenesis, EVs may acquire a repertoire of cytosolic components, such as lipids and proteins, as well as coding- and noncoding RNAs (Keerthikumar et al. (2016) J Mol Biol. 428(4):688-92; Kalra et al. (2012) PLoS Biol. 10(12):e1001450; Fatima et al. (2017) Noncoding RNA 3(1):10). Cells can also send RNA messages to one another by packaging the messages into EVs (Valadi et al. (2007) Nat Cell Biol. 9(6):654-9). Thus, EVs can act as endogenous carriers for nucleic acid transfer between cells. The most extensively described EVs are exosomes, which originate from endosomes and are secreted through the exocytosis pathway.

Exosomes are nanoscale EVs that are secreted by almost all kinds of cells and that stably exist in virtually all kinds of bodily fluids (Ibrahim and Marbán (2016) Annu Rev Physiol. 78:67-83). Exosomes can transmit a variety of signaling molecules, including nucleic acids (e.g., mRNA and microRNA), functional proteins, and lipids (Valadi et al. (2007) Nat Cell Biol. 9(6):654-9; Li et al. (2016) Nat Commun. 7:10872; Liu et al. (2015) Cell Metab. 22(4):606-18). Owing to the small size of exosomes, they can also escape from the rapid phagocytosis by mononuclear phagocytes, steadily carry and deliver drugs in circulation, and pass through vascular endothelium to target cells (van den Boorn et al. (2011) Nat Biotechnol. 29(4):325-6). In addition, exosomes are capable of crossing stringent biological barriers, such as the blood-brain barrier and the placental barrier (Alvarez-Erviti et al. (2011) Nat Biotechnol. 29(4):341-5; Holder et al. (2016) Traffic 17(2):168-78; Shi et al. (2017) Biochem Biophys Res Commun. 483(1):602-8). All of these characteristics make exosomes a promising carrier for RNA delivery.

Several exosome-based delivery systems have been described for therapeutic use, such as the exosome-liposome hybrid nanoparticles reported in Lin et al. ((2018) Adv Sci. (Weinh) 5(4):1700611). However, to date, none of these systems have been developed to address the toxic effects that can result from particular RNA delivery formulations. Thus, there remains a need for effective RNA delivery systems that minimize side effects and avoid undue toxicity in cells and tissues.

In various embodiments, the present disclosure provides, in part, exosomes (EVs) for the delivery of therapeutic RNAs. In various embodiments, the exosomes described herein are capable of delivering exogenous RNAs, including high molecular weight mRNAs, to target cells and tissues. In various embodiments, the exosomes described herein are capable of protecting an exogenous RNA during in vitro or in vivo transport, and delivering the RNA to the cytoplasm of recipient cells. In various embodiments, the delivered RNA is functional and can be translated to produce a therapeutic protein. In various embodiments, the exosomes described herein may be non-immunogenic, or may elicit a reduced immune and/or inflammatory response, as compared to the immune and/or inflammatory response observed with alternate delivery vehicles (e.g., LNPs). In various embodiments, the exosomes described herein have an ionizable lipid:modified RNA nucleotides molar ratio of about 1:1 or less than about 1:1, e.g., about 0.1:1, about 0.2:1, about 0.3:1, about 0.4:1, about 0.5:1, about 0.6:1, about 0.7:1, about 0.8:1, or about 0.9:1. In various embodiments, exosomes having an ionizable lipid:modified RNA nucleotides molar ratio of about 1:1 or less than about 1:1 may be non-toxic or less toxic in host cells and tissues, as compared to alternate delivery vehicles having an ionizable lipid:modified RNA nucleotides molar ratio greater than about 1:1 (e.g., LNPs). In various embodiments, the exosomes and the alternate delivery vehicles comprise the same ionizable lipid (e.g., DLin-MC3-DMA or DLin-DMA) and the same modified RNA, but comprise different ionizable lipid:modified RNA nucleotides molar ratios.

In various embodiments, the present disclosure provides an isolated exosome comprising a modified RNA prepared by a process comprising: (a) providing one or more lipid nanoparticles (LNP) comprising the modified RNA; (b) contacting one or more cells with the LNP under conditions that allow LNP uptake by the cell; and (c) isolating exosomes produced by the one or more cells, wherein at least one isolated exosome comprises the modified RNA.

In some embodiments, the LNP comprises at least one ionizable lipid, phospholipid, structural lipid, and/or PEG lipid.

In some embodiments, the at least one ionizable lipid comprised by the LNP is DLin-MC3-DMA and/or DLin-DMA. In some embodiments, the at least one ionizable lipid comprised by the LNP is DLin-MC3-DMA. In some other embodiments, the at least one ionizable lipid comprised by the LNP is DLin-DMA. In some embodiments, the at least one phospholipid comprised by the LNP is DSPC. In some embodiments, the at least one structural lipid comprised by the LNP is cholesterol. In some embodiments, the at least one PEG lipid comprised by the LNP is PEG-DMPE. In some embodiments, the molecular weight of the PEG may be about 2,000 Da (PEG2000). In some embodiments, the at least one PEG lipid comprised by the LNP is PEG2000-DMPE.

In some embodiments, the LNP comprises an ionizable lipid that is DLin-MC3-DMA or DLin-DMA, a phospholipid that is DSPC, a structural lipid that is cholesterol, and/or a PEG lipid that is PEG-DMPE or PEG2000-DMPE. In some embodiments, the LNP comprises an ionizable lipid that is DLin-MC3-DMA, a phospholipid that is DSPC, a structural lipid that is cholesterol, and a PEG lipid that is PEG-DMPE or PEG2000-DMPE. In some embodiments, the LNP comprises an ionizable lipid that is DLin-DMA, a phospholipid that is DSPC, a structural lipid that is cholesterol, and a PEG lipid that is PEG-DMPE or PEG2000-DMPE.

In some embodiments, the LNP comprises an ionizable lipid:modified RNA nucleotides molar ratio of about 2:1 to about 4:1, or about 4:1, about 3:1, or about 2:1. In some embodiments, the LNP comprises an ionizable lipid:modified RNA nucleotides molar ratio of about 3:1.

In some embodiments, the exosome produced by contacting one or more cells with the LNP comprises at least one ionizable lipid, phospholipid, structural lipid, and/or PEG lipid. In some embodiments, the at least one ionizable lipid, phospholipid, structural lipid, and/or PEG lipid comprised by the exosome is derived from the LNP.

In some embodiments, the at least one ionizable lipid comprised by the exosome is DLin-MC3-DMA and/or DLin-DMA. In some embodiments, the at least one ionizable lipid comprised by the exosome is DLin-MC3-DMA. In some embodiments, the at least one ionizable lipid comprised by the exosome is DLin-DMA. In some embodiments, the at least one phospholipid comprised by the exosome is DSPC. In some embodiments, the at least one structural lipid comprised by the exosome is cholesterol.

In some embodiments, the exosome comprises an ionizable lipid that is DLin-MC3-DMA or DLin-DMA, a phospholipid that is DSPC, and/or a structural lipid that is cholesterol. In some embodiments, the exosome comprises an ionizable lipid that is DLin-MC3-DMA, a phospholipid that is DSPC, and a structural lipid that is cholesterol. In some other embodiments, the exosome comprises an ionizable lipid that is DLin-DMA, a phospholipid that is DSPC, and a structural lipid that is cholesterol.

In some embodiments, the exosome comprises an ionizable lipid:modified RNA nucleotides molar ratio of about 1:1 to about 3:1, or about 3:1, about 2:1, about 1:1, or less than about 1:1. In some embodiments, the exosome comprises an ionizable lipid:modified RNA nucleotides molar ratio of about 1:1 or less than about 1:1, e.g., about 0.1:1, about 0.2:1, about 0.3:1, about 0.4:1, about 0.5:1, about 0.6:1, about 0.7:1, about 0.8:1, or about 0.9:1. In some embodiments, the exosome comprises an ionizable lipid:modified RNA nucleotides molar ratio that is less than the ionizable lipid:modified RNA nucleotides molar ratio comprised by the LNP. In some embodiments, the exosome comprises an ionizable lipid:modified RNA nucleotides molar ratio of about 1:1 or less than about 1:1, and the LNP comprises an ionizable lipid:modified RNA nucleotides molar ratio of about 3:1.

In some embodiments, the exosome has a diameter of about 30 nm to about 300 nm. In some embodiments, the exosome has a diameter of about 40 nm to about 150 nm. In some embodiments, the exosome has a diameter of about 40 nm to about 120 nm.

In some embodiments, the cell for contacting with the LNP and producing the exosome is obtained from a subject. In some embodiments, the cell is an epithelial cell, an immune cell, a progenitor cell, or a stem cell. In some embodiments, the cell is a B-lymphocyte, a T-lymphocyte, or a monocyte.

In some embodiments, the modified RNA encodes a polypeptide of interest. In some embodiments, the modified RNA encodes a polypeptide effective to treat a disorder. In some embodiments, the modified RNA encodes an erythropoietin polypeptide. In some embodiments, the modified RNA encodes a human erythropoietin polypeptide. In some embodiments, the modified RNA encodes an erythropoietin polypeptide of SEQ ID NO:1.

In some embodiments, the exosome is prepared by a process performed in vitro. In some embodiments, contacting one or more cells with the LNP is performed in the presence of human serum. In some embodiments, the human serum is present at about 0.5%, about 1%, or about 1.5% by volume. In some embodiments, the human serum is present at about 1% by volume. In some embodiments, contacting one or more cells with the LNP comprises contacting the one or more cells with at least 2, at least 3, or at least 4 different doses of the LNP. In some embodiments, contacting one or more cells with the LNP comprises contacting the one or more cells with at least 3 different doses of the LNP. In some embodiments, isolating exosomes comprises isolating exosomes from a sample of in vitro cell culture medium.

In various embodiments, the present disclosure also provides a method of delivering a modified RNA to a cell by contacting the cell with an effective amount of an exosome or a pharmaceutical composition comprising at least one exosome (e.g., any of the exosomes or pharmaceutical compositions described herein), thereby delivering the modified RNA to the cell. In some embodiments, contacting the cell comprises adding the exosomes or pharmaceutical composition to an in vitro cell culture or administering the exosomes or pharmaceutical composition to a subject.

Also provided herein, in various embodiments, is a use of an effective amount of an exosome or a pharmaceutical composition comprising at least one exosome (e.g., any of the exosomes or pharmaceutical compositions described herein) in delivering a modified RNA to a cell.

In some embodiments of the methods and uses described herein, the cell is present in an in vitro cell culture. In some embodiments, the cell is obtained from a subject. In some embodiments, the cell is present in a subject. In some embodiments, the cell is an epithelial cell, an immune cell, a progenitor cell, or a stem cell. In some embodiments, the cell is a B-lymphocyte, a T-lymphocyte, or a monocyte.

In some embodiments of the methods and uses described herein, delivering the modified RNA to the cell does not alter cell generation time. In some embodiments, delivering the modified RNA to the cell does not alter total cell protein content by weight.

Further provided herein, in various embodiments, are pharmaceutical compositions comprising at least one exosome (e.g., any of the exosomes described herein), and a pharmaceutically acceptable carrier.

Still further provided herein, in various embodiments, are therapeutic methods and uses for the exosomes and pharmaceutical compositions disclosed herein, e.g., in treating a disorder.

For instance, in certain aspects, the present disclosure provides a method of treating or preventing a disorder in a subject by administering to the subject an effective amount of an exosome or pharmaceutical composition comprising at least one exosome (e.g., any of the exosomes or pharmaceutical compositions described herein), wherein the exosomes comprise a modified RNA effective to treat the disorder. In some embodiments, the exosomes are isolated from a cell obtained from the subject.

In certain other aspects, the present disclosure provides a use of an effective amount of an exosome or pharmaceutical composition comprising at least one exosome (e.g., any of the exosomes or pharmaceutical compositions described herein) in treating or preventing a disorder in a subject, wherein the exosomes comprise a modified RNA effective to treat the disorder. In some embodiments, the exosomes are isolated from a cell obtained from the subject.

In still other aspects, the present disclosure provides a method of treating or preventing a disorder in a subject by (a) providing one or more cells obtained from the subject; (b) contacting the one or more cells with one or more lipid nanoparticles (LNP) comprising a modified RNA under conditions that allow LNP uptake by the cell; (c) isolating exosomes produced by the one or more cells, wherein at least one isolated exosome comprises the modified RNA; and (d) administering to the subject an effective amount of the isolated exosome, wherein the modified RNA is effective to treat the disorder. In some embodiments, the cell is an epithelial cell, an immune cell, a progenitor cell, or a stem cell. In some embodiments, the cell is a B-lymphocyte, a T-lymphocyte, or a monocyte.

In still other aspects, the present disclosure provides a use of an effective amount of an isolated exosome in treating or preventing a disorder in a subject by (a) providing one or more cells obtained from the subject; (b) contacting the one or more cells with one or more lipid nanoparticles (LNP) comprising a modified RNA under conditions that allow LNP uptake by the cell; (c) isolating exosomes produced by the one or more cells, wherein at least one isolated exosome comprises the modified RNA; and (d) administering to the subject an effective amount of the isolated exosome, wherein the modified RNA is effective to treat the disorder. In some embodiments, the cell is an epithelial cell, an immune cell, a progenitor cell, or a stem cell. In some embodiments, the cell is a B-lymphocyte, a T-lymphocyte, or a monocyte.

In some embodiments of the methods and uses disclosed herein, the disorder is selected from anemia, myelodysplasia, an immune or inflammatory disease, a monogenetic disorder, and a complex disease. In some embodiments, the disorder is anemia. In some embodiments, the disorder is myelodysplasia. In some embodiments, the disorder is an immune or inflammatory disease. In some embodiments, the immune or inflammatory disease is inflammatory bowel disease. In some embodiments, the disorder is a monogenetic disorder. In some embodiments, the monogenetic disorder is a neurodegenerative disease. In some embodiments, the disorder is a complex disease. In some embodiments, the complex disease is a myocardial infarction. In some embodiments, the complex disease is a cancer.

In some embodiments of the methods and uses disclosed herein, the modified RNA encodes a polypeptide effective to treat the disorder. In some embodiments, the modified RNA encodes an erythropoietin polypeptide. In some embodiments, the modified RNA encodes a human erythropoietin polypeptide. In some embodiments, the modified RNA encodes an erythropoietin polypeptide of SEQ ID NO:1.

In some embodiments of the methods and uses disclosed herein, the subject has a reduced immune and/or inflammatory response to treatment in the presence of an exosome as compared to treatment in the absence of an exosome. In some embodiments, the reduced immune and/or inflammatory response comprises an increase or decrease in the level of at least one cytokine. In some embodiments, the reduced immune and/or inflammatory response comprises a decrease in the level of at least one cytokine, wherein the cytokine is selected from IL-6, IP-10, RANTES, MCP-1, and KC.

In some embodiments of the methods and uses disclosed herein, contacting one or more cells with the LNP is performed in the presence of human serum. In some embodiments, the human serum is present at about 0.5%, about 1%, or about 1.5% by volume. In some embodiments, the human serum is present at about 1% by volume. In some embodiments, contacting one or more cells with the LNP comprises contacting the one or more cells with at least 2, at least 3, or at least 4 different doses of the LNP. In some embodiments, contacting one or more cells with the LNP comprises contacting the one or more cells with at least 3 different doses of the LNP. In some embodiments, isolating exosomes comprises isolating exosomes from a sample of in vitro cell culture medium.

BRIEF DESCRIPTION OF THE DRAWINGS

FIG. 4O and FIG. 4P show quantification of hEPO mRNA (FIG. 4O) and hEPO protein (FIG. 4P) in mouse brain. 5 hours, 24 hours, and 96 hours after EV injection (1.5 µg of hEPO mRNA per mouse), levels of hEPO mRNA in brain were quantified by RT-qPCR and levels of hEPO protein was quantified by ELISA. Data are presented as mean values with standard deviation (SD) of four replicates (n=4) at each time point as a scattered plot. EV treated and untreated groups were compared at each time point using a parametric unpaired two-tailed t test. Significant values are shown as P-values: *$P<0.05$, $P<0.01$, *$P<0.001$.

FIG. 14O and FIG. 14P show quantification of hEPO mRNA (FIG. 14O) and hEPO protein (FIG. 14P) in mouse brain. Mice were intravenously injected with 100 μL of MC3-LNPs, containing 1.5 μg of hEPO mRNA (per mouse), or with the equivalent volume of PBS as a control. Levels of hEPO mRNA and hEPO protein were quantified 5 hours, 24 hours, and 96 hours after injection by RT-qPCR and ELISA, respectively. Data are presented as total amount of hEPO mRNA or protein detected in the entire organ normalized to organ weight. For each time point, and each kind of treatment (LNPs or PBS), four mice (n=4) were used. Data are presented as mean values with standard deviation (SD) of four replicates (n=4), at each time point. Each dot in the scattered plot represents each replicate. For each time point, the MC3-LNPs and PBS groups were compared using a parametric unpaired two-tailed t test. Only significant P-values are shown: *P<0.05, P<0.01, *P<0.001, ****P<0.0001.

FIG. 16A shows the size distribution and concentration of EVs derived from untreated HTB-177 cells (n=3, (i)-(iii)). FIG. 16B shows the size distribution and concentration of EVs derived from MC3-LNP treated HTB-177 cells (n=3, (i)-(iii)). Mean size, mode size, standard deviation (SD), D10, D50, D90, and particle concentration are shown in Tables 3-8.

FIG. 17A shows FACs dot plots representing Cy5-mRNA (y-axis) vs. CD9 (x-axis). The percentage of CD63/CD9 positive EVs containing Cy5-mRNA is presented in the upper right quadrant. Sole beads incubated with PBS instead of EVs are shown as a negative control. One of two biological replicates is shown.

FIG. 17B shows the effects of RNase treatment on control pure hEPO mRNA (cell free and EV free (left side)) or on MC3-EVs (right side). The experiment was performed in three biological replicates (n=3) and hEPO mRNA qPCR data are represented as a scatter dot plot and mean standard deviation (SD).

DETAILED DESCRIPTION OF ILLUSTRATIVE EMBODIMENTS

Figure 1A:
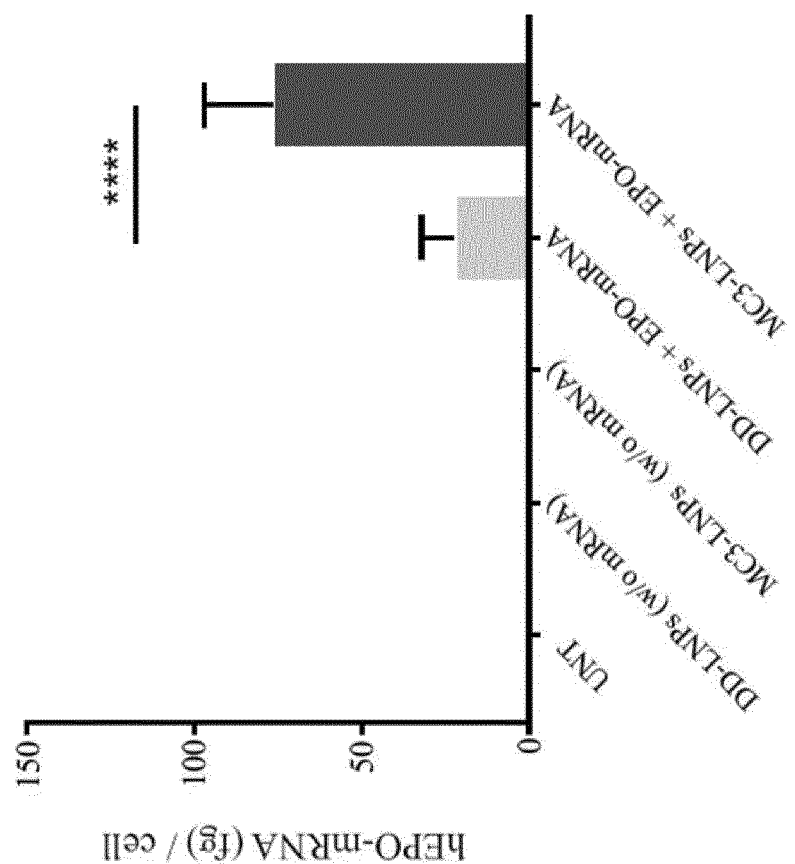
FIG. 1A shows the amount of hEPO mRNA detected in human epithelial (HTB-177) cells after LNP delivery. LNPs with DLin-DMA ionizable lipids (DD-LNPs), and LNPs with DLin-MC3-DMA ionizable lipids (MC3-LNPs), each containing 100 µg of hEPO mRNA, were transferred to HTB-177 cells in independent experiments. Untreated cells and cells treated with LNPs without hEPO mRNA were used as controls. After 96 hours of LNP treatment, hEPO mRNA was quantified in recipient cells by RT-qPCR. The amount of hEPO mRNA detected in cells was normalized to the total number of harvested cells after 96 hours of LNP treatment.

In order that the disclosure may be more readily understood, certain terms are defined throughout the detailed description. Unless defined otherwise herein, all scientific and technical terms used in connection with the present disclosure have the same meaning as commonly understood by those of ordinary skill in the art.

As used herein, the term "extracellular vesicle" or "EV" refers to a nano- or micro-sized membrane vesicle secreted or shed from a cell. EVs are enclosed by a lipid bilayer and range in size from approximately 30 nm to 10,000 nm in diameter. In certain embodiments, the EVs are exosomes.

As used herein, the terms "exosome" and "endo-EV" are used interchangeably herein to refer to an endosomal-derived EV. Without wishing to be bound by theory, it is believed that materials endocytosed by a cell or other cellular components may be sorted into endosomal compartments, forming intraluminal vesicles (multivesicular endosomes or multivesicular bodies (MVBs)). The vesicles may then be released into the extracellular environment upon the fusion of MVBs with the plasma membrane. The released vesicles may be referred to herein as exosomes. In some embodiments, an exosome is secreted or shed from a cell after the endocytosis of LNPs. In some embodiments, an exosome secreted or shed from a cell that has been contacted or treated with LNPs may comprise one or more LNP components (e.g., one or more ionizable lipids and/or one or more modified RNAs). In some embodiments, an exosome is secreted through the exocytosis pathway. In some embodiments, an exosome has a diameter of about 30 nm to about 300 nm. In some embodiments, an exosome has a diameter of about 30 nm to about 150 nm. In some embodiments, the exosome has a diameter of about 40 nm to about 150 nm. In some embodiments, an exosome has a diameter of about 40 nm to about 120 nm. Exemplary exosomes include MC3-EVs and DD-EVs, as described and exemplified herein.

As used herein, the term "endosomal escape" refers to an RNA exiting the endosomal pathway and entering the cytosol, following endocytosis. The endocytosis pathway is believed to be the major cellular uptake mechanism of biological agents, such as DNA, RNA, or proteins. Such agents can be entrapped in endosomes and degraded by specific enzymes in the lysosome. Thus, in some embodiments, a limiting step in achieving an effective biological-based therapy is to facilitate the endosomal escape of therapeutic agents (e.g., modified RNAs, e.g., mRNAs) and ensure their cytosolic delivery. In some embodiments, less than about 1% of the total modified RNA delivered to a cell via an LNP may undergo endosomal escape and be released into the cytosol. In some embodiments, a portion of the LNP components (e.g., a portion of the non-escaped modified RNA and/or a portion of the LNP lipid component) may end up in exosomes secreted from the cell, following LNP endocytosis.

As used herein, a "lipid nanoparticle" or "LNP" is a nanoparticle comprising one or more lipids and one or more therapeutic agents (e.g., one or more modified RNAs). Nanoparticles are typically sized on the order of micrometers or smaller. In some embodiments, the LNPs disclosed herein have an average particle size of about 200 nm in diameter or less, about 150 nm in diameter or less, about 100 nm in diameter or less, about 75 nm in diameter or less, or about 50 nm in diameter or less. In some embodiments, the LNPs disclosed herein have an electron dense nanostructured core produced by microfluidic mixing of lipid-containing solutions in ethanol with aqueous solutions containing modified RNAs (e.g., mRNAs). In some embodiments, the LNPs disclosed herein do not have continuous aqueous regions exceeding 50% by volume and thus, exclude conventional liposomes such as unilamellar vesicles and the like.

In various embodiments, an isolated exosome can be prepared by a process comprising: (a) providing one or more lipid nanoparticles (LNP) comprising a modified RNA; (b) contacting one or more cells with the LNP under conditions that allow LNP uptake by the cell; and (c) isolating exosomes produced by the one or more cells, wherein at least one isolated exosome comprises the modified RNA.

In various embodiments, the LNP has a mean diameter of about 50 nm to about 100 nm, for example, about 60 nm to about 90 nm, about 70 nm to about 80 nm, or about 80 nm to about 90 nm. In some embodiments, the LNP has a mean diameter of about 70 nm, about 71 nm, about 72 nm, about 73 nm, about 74 nm, about 75 nm, about 76 nm, about 77 nm, about 78 nm, about 79 nm, about 80 nm, about 81 nm, about 82 nm, about 83 nm, about 84 nm, about 85 nm, about 86 nm, about 87 nm, about 88 nm, about 89 nm, or about 90 nm. In some embodiments, the LNP has a mean diameter of about 83 nm, about 84 nm, about 85 nm, about 86 nm, about 87 nm, or about 88 nm.

In various embodiments, the LNP has a polydispersity index (PDI) of about 0.01 to about 0.15, for example, about 0.01, about 0.02, about 0.03, about 0.04, about 0.05, about 0.06, about 0.07, about 0.08, about 0.09, about 0.10, about 0.11, about 0.12, about 0.13, about 0.14, or about 0.15. As used herein, the term "polydispersity index" or "PDI" refers to the measure of the distribution of nanoparticle sizes in a nanoparticulate sample (see NIST Special Publication 1200-6, "Measuring the Size of Nanoparticles in Aqueous Media Using Batch Mode Dynamic Light Scattering").

In various embodiments, the LNP has an encapsulation efficiency (% EE) of modified RNAs of about 80% or higher, about 85% or higher, about 90% or higher, about 94% or higher, about 95% or higher, about 96% or higher, about 97% or higher, about 98% or higher, or about 99% or higher. As used herein, the term "encapsulation efficiency" or "% EE" refers to the ratio of encapsulated modified RNA in the LNPs to total modified RNA content in the composition measured by lysis of the LNPs using a detergent, e.g., Triton X-100.

In various embodiments, the LNP comprises a lipid component and at least one modified RNA. In various embodiments, the one or more exosomes produced by contacting one or more cells with the LNP (e.g., any of the LNPs disclosed herein) comprises a lipid component and at least one modified RNA. In various embodiments, the lipid component of the exosomes may, at least in part, be derived from the lipid component of the LNP. In various embodiments, the lipid component of the exosomes may comprise one or more of the same lipids as the lipid component of the LNP.

As used herein, the term "lipid component" refers to a component of an LNP and/or exosome that includes one or more lipids. For example, the lipid component of an LNP and/or exosome disclosed herein may include one or more ionizable lipids, one or more phospholipids, one or more structural lipids, and/or one or more PEG lipids. In various embodiments, the lipid component of an LNP and/or exosome may comprise a lipid monolayer and/or a lipid bilayer.

In various embodiments, the lipid component of an LNP may be constructed from any materials used in conventional nanoparticle technology, for example, ionizable lipids, phospholipids, structural lipids, and/or PEG lipids. In various embodiments, at least one lipid present in the lipid component of an LNP is also present in the lipid component of an exosome, wherein the exosome is produced by contacting one or more cells with the LNP.

In various embodiments, the lipid component of an LNP and/or an exosome disclosed herein may include one or more ionizable lipids.

Non-limiting examples of ionizable lipids include, for instance, lipids containing a positive charge at acidic pH, for example, 1,2-dilinoleyloxy-3-dimethylaminopropane (DLin-DMA), dilinoleylmethyl-4-dimethylaminobutyrate (DLin-MC3-DMA; see, e.g., U.S. Pat. No. 8,158,601, which is incorporated herein by reference), 2-dilinoleyl-4-dimethylaminoethyl-[1,3]-dioxolane (DLin-KC2-DMA), Merck-32 (see, e.g., WO 2012/018754, which is herein incorporated by reference), Acuitas-5 (see, e.g., WO 2015/199952, which is herein incorporated by reference), KL-10 (see, e.g., US 2012/0295832, which is herein incorporated by reference), C12-200 (see, e.g., Love et al. (2009) PNAS 107(5):1864-69), and the like. In various embodiments, the ionizable lipid is DLin-MC3-DMA. In various embodiments, the ionizable lipid is DLin-DMA.

In some embodiments, the LNP comprises at least one ionizable lipid. In some embodiments, the at least one ionizable lipid may be present in the LNP in an amount ranging from about 5% to about 90%, about 10% to about 80%, about 25% to about 75%, or about 40% to about 60%, such as about 50%, molar percent, relative to the total lipid present in the LNP. In some embodiments, the at least one ionizable lipid is present in the LNP at about 50% molar percent relative to the total lipid present in the LNP. In some embodiments, the at least one ionizable lipid is DLin-MC3-DMA. In some other embodiments, the at least one ionizable lipid is DLin-DMA.

As used herein, the term "MC3-LNPs" may be used to refer to LNPs comprising an ionizable lipid majority of DLin-MC3-DMA ionizable lipids.

As used herein, the term "DD-LNPs" may be used to refer to LNPs comprising an ionizable lipid majority of DLin-DMA ionizable lipids.

In some embodiments, an exosome comprises at least one ionizable lipid. In some embodiments, the at least one ionizable lipid is DLin-MC3-DMA. In some other embodiments, the at least one ionizable lipid is DLin-DMA.

As used herein, the term "MC3-EVs" may be used to refer to exosomes (EVs) isolated from cells contacted or treated with MC3-LNPs.

As used herein, the term "DD-EVs" may be used to refer to exosomes (EVs) isolated from cells contacted or treated with DD-LNPs.

In various embodiments, the lipid component of an LNP and/or an exosome disclosed herein may include one or more phospholipids. In various embodiments, phospholipids may assemble into one or more lipid bilayers. In general, phospholipids may include a phosphate moiety and one or more carbon chains, such as saturated fatty acid chains. In various embodiments, a phospholipid may include one or more multiple (e.g., double or triple) bonds (i.e., one or more unsaturations). In various embodiments, a phospholipid may facilitate fusion to a membrane. In various embodiments, fusion of a phospholipid to a membrane may allow one or more elements of a lipid-containing composition to pass through the membrane permitting, e.g., delivery of the one or more elements to a cell.

Exemplary phospholipids include, but are not limited to, 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine,1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin. In various embodiments, the phospholipid is DSPC.

Exemplary phospholipids also include, for instance, neutral lipids containing a zero net charge at physiological pH. Non-limiting examples of neutral lipids include those lipids that exist in an uncharged form or neutral zwitterionic form at physiological pH, such as 1,2-distearoyl-sn-glycero-3-phosphocholine (DSPC), 1,2-dioleoyl-sn-glycero-3-phosphoethanolamine (DOPE), 1,2-dipalmitoyl-sn-glycero-3-phosphocholine (DPPC), 1,2-dimyristoyl-sn-gly cero-phosphocholine (DMPC), and the like. In various embodiments, the phospholipid is DSPC.

In some embodiments, an LNP comprises at least one phospholipid. In some embodiments, the at least one phospholipid may be present in an LNP in an amount ranging from about 1% to about 50%, about 5% to about 20%, about 7.5% to about 12.5%, such as about 10%, molar percent, relative to the total lipid present in the LNP. In some embodiments, the at least one phospholipid is present in the LNP at about 10% molar percent relative to the total lipid present in the LNP. In some embodiments, the at least one phospholipid is DSPC.

In some embodiments, an exosome comprises at least one phospholipid. In some embodiments, the at least one phospholipid is DSPC.

In various embodiments, the lipid component of an LNP and/or an exosome disclosed herein may include one or more structural lipids. As used herein, the term "structural lipid" refers to a molecule capable of stabilizing and/or maintaining the structure or fluidity of a lipid component, such as a sterol (e.g., an animal sterol, a plant sterol, a fungi sterol). An exemplary structural lipid is cholesterol.

Non-limiting examples of structural lipids include, for instance, cholesterol, fecosterol, sitosterol, ergosterol, campesterol, stigmasterol, brassicasterol, tomatidine, tomatine, ursolic acid, alpha-tocopherol, and mixtures thereof. In various embodiments, the structural lipid is cholesterol.

In some embodiments, an LNP comprises at least one structural lipid. In some embodiments, the at least one structural lipid may be present in an LNP in an amount ranging from about 10% to about 90%, about 20% to about 50%, about 35% to 45%, such as about 38.5%, molar percent, relative to the total lipid present in the LNP. In some embodiments, the at least one structural lipid is present in the LNP at about 38.5% molar percent relative to the total lipid present in the LNP. In some embodiments, the least one structural lipid is cholesterol.

In some embodiments, an exosome comprises at least one structural lipid. In some embodiments, the at least one structural lipid is cholesterol.

In various embodiments, the lipid component of an LNP and/or an exosome disclosed herein may include one or more PEG or PEG-modified lipids. Such lipids may be alternately referred to as PEGylated lipids. In various embodiments, a PEG lipid comprises both a lipid portion and a polyethylene glycol portion.

Exemplary PEG lipids include, but are not limited to, PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, in various embodiments, a PEG lipid may be PEG-c-DOMG, PEG-DMG (1,2-dimyristoyl-OT-glycerol methoxypoly ethylene glycol, obtainable from Avanti Polar Lipids), PEG-DLPE, PEG-DMPE, PEG-DPPC, or PEG-DSPE. In various embodiments, the molecular weight of the PEG may be about 2,000 Da (PEG2000). In various embodiments, a PEG lipid may be PEG2000-DMPE, PEG2000-DPPE, PEG2000-DMG, PEG2000-DPG, PEG2000-c-DOMG, or PEG2000-C-DOPG. In various embodiments, the PEG lipid is PEG-DMPE or PEG2000-DMPE. In various embodiments, the molecular weight of the PEG may range from about 500 to about 10,000 Da, or from about 1,000 to about 5,000 Da.

In some embodiments, an LNP comprises at least one PEG lipid. In some embodiments, the at least one PEG lipid may be present in an LNP in an amount ranging from about 0% to about 20%, about 0.5% to about 5%, about 1% to about 2%, for instance, about 1.5%, molar percent, relative to the total lipid present in the LNP. In some embodiments, the at least one PEG lipid is present in the LNP at about 1.5% molar percent relative to the total lipid present in the LNP. In some embodiments, the least one PEG lipid is PEG-DMPE or PEG2000-DMPE.

In some embodiments, an exosome comprises at least one PEG lipid. In some embodiments, the at least one PEG lipid is PEG-DMPE or PEG2000-DMPE.

In various embodiments, the LNPs disclosed herein may be prepared by combining multiple lipid components. For example, in various embodiments, an LNP may be prepared by combining one or more of an ionizable lipid, a phospholipid, a structural lipid, and a PEG lipid. In various embodiments, an LNP may be prepared by combining an ionizable lipid, a phospholipid, a structural lipid, and a PEG lipid, wherein the PEG lipid is present in the LNP at about 1.5% molar percent relative to the total lipid present in the LNP. In various embodiments, an LNP may be prepared by combining an ionizable lipid (such as DLin-MC3-DMA or DLin-DMA), a phospholipid (such as DSPC), a structural lipid (such as cholesterol), and a PEG lipid (such as PEG-DMPE) at a molar ratio of about 50:10:38.5:1.5 (mol/mol), with respect to total lipids present.

The selection of ionizable lipids, phospholipids, structural lipids, and/or PEG lipids that comprise the LNPs disclosed herein, as well as the relative molar ratio of such lipids to each other, may be determined by the characteristics of the selected lipid(s), the nature of the intended target cells, and the characteristics of the modified RNA, such as, for example, mRNA, to be delivered. For instance, in some embodiments, the molar percent of ionizable lipid in the LNP may be greater than about 10%, greater than about 20%, greater than about 30%, greater than about 40%, greater than about 50%, greater than about 60%, or greater than about 70%, relative to the total lipids present. In some embodiments, the molar percent of phospholipid in the LNP may be greater than about 5%, greater than about 10%, greater than about 20%, greater than about 30%, or greater than about 40%, relative to the total lipids present. In some embodiments, the molar percent of structural lipid in the LNP may be greater than about 10%, greater than about 20%, greater than about 30%, greater than about 40%, or greater than about 50%, relative to the total lipids present. In some embodiments, the molar percent of PEG lipid in the LNP may be greater than about 0.25%, such as greater than about 1%, greater than about 1.5%, greater than about 2%, greater than about 5%, or greater than about 10%, relative to the total lipids present.

In various embodiments, the LNPs disclosed herein may comprise each of the ionizable lipids, phospholipids, structural lipids, and/or PEG lipids in any useful orientation desired. In some embodiments, the core of the LNP may comprise an ionizable lipid and a structural lipid and one or more layers comprising phospholipids and/or PEG lipids may subsequently surround the core. For instance, in some embodiments, the LNP may comprise a core comprising an ionizable lipid (e.g., DLin-MC3-DMA or DLin-DMA) and a structural lipid (e.g., cholesterol) in any particular ratio, surrounded by a phospholipid monolayer (e.g., DSPC) of any particular thickness, further surrounded by an outer PEG lipid monolayer of any particular thickness. In some embodiments, the modified RNA (e.g., mRNA) may be incorporated into any one of the core or subsequent layers depending upon the nature of the intended target cells, and the characteristics of the modified RNA, such as, for example, mRNA, to be delivered. In some embodiments, the core and outer layers may further comprise other components typically incorporated into LNPs known in the art.

In addition, in some embodiments, the molar percent of ionizable lipids, phospholipids, structural lipids, and/or PEG lipids that comprise the LNPs may be selected in order to provide a particular physical parameter of the overall LNP, such as the surface area of one or more of the lipids. For example, in some embodiments, the molar percent of ionizable lipids, phospholipids, structural lipids, and/or PEG lipids that comprise the LNPs may be selected to yield a surface area per phospholipid (e.g., DSPC). In some embodiments, the molar percent of ionizable lipids, phospholipids, structural lipids, and/or PEG lipids may be determined to yield a surface area per phospholipid (e.g., DSPC) of about 1.0 nm$^2$ to about 2.0 nm$^2$.

In addition to a lipid component, in various embodiments, an LNP and/or an exosome disclosed herein further comprises at least one modified RNA (e.g., mRNA).

As used herein, the term "modified RNA" refers to any ribonucleic acid (RNA) sequence that has been modified with respect to a reference (unmodified) RNA sequence (e.g., a naturally-occurring counterpart). In some embodiments, a modified RNA contains one or more nucleoside/nucleotide substitutions, deletions, and/or insertions as compared to a reference RNA. In some embodiments, a modified RNA contains a chemical change to one or more nucleosides/nucleotides as compared to a reference RNA. In some embodiments, for example, a modified RNA can include at least one uridine monophosphate (UMP) that is modified to form N1-methyl-pseudo-UMP. In some embodiments, all UMPs in a modified RNA have been replaced by N1-methyl-pseudo-UMP. A modified RNA does not necessarily require physical manipulation of the reference RNA. As long as a modified RNA sequence contains at least one modification as compared to a reference RNA sequence, it is considered "modified" regardless of how it was synthesized. In some embodiments, the modified RNA is a low molecular weight modified RNA. In some embodiments, the modified RNA is a high molecular weight modified RNA. In some embodiments, the modified RNA is a modified messenger RNA (mRNA). In some embodiments, the modified RNA is a low molecular weight modified mRNA. In some other embodiments, the modified RNA is a high molecular weight modified mRNA. In some embodiments, the modified RNA encodes an erythropoietin polypeptide. In some embodiments, the modified RNA encodes a human erythropoietin polypeptide. In some embodiments, the modified RNA encodes an erythropoietin polypeptide of SEQ ID NO:1. Exemplary RNA and amino acid sequences are set forth in Table 1.

TABLE 1

Exemplary RNA and amino acid sequences.

| Name | SEQ ID NO | Sequence |
|---|---|---|
| Human erythropoietin (protein) | 1 | MGVHECPAWLWLLLSLLSLPLGLPVLGAPPRLICDS RVLERYLLEAKEAENITTGCAEHCSLNENITVPDTK VNFYAWKRMEVGQQAVEVWQGLALLSEAVLRGQALL VNSSQPWEPLQLHVDKAVSGLRSLTTLLRALGAQKE AISPPDAASAAPLRTITADTFRKLFRVYSNFLRGKL KLYTGEACRTGDR |
| Human erythropoietin (mRNA) | 2 | CCCGGAGCCGGACCGGGGCCACCGCGCCCGCTCTGC TCCGACACCGCGCCCCTGGACAGCCGCCCTCTCCT CCAGGCCCGTGGGGCTGGCCCTGCACCGCCGAGCTT CCCGGGATGAGGGCCCCGGTGTGGTCACCCGGCGC GCCCCAGGTCGCTGAGGGACCCCGGCCAGGCGCGGA GATGGGGGTGCACGAATGTCCTGCCTGGCTGTGGCT TCTCCTGTCCCTGCTGTCGCTCCCTCTGGGCCTCCA AGTCCTGGGCGCCCACCACGCCTCATCTGTGACAG CCGAGTCCTGGAGAGGTACCTCTTGGAGGCCAAGGA GGCCGAGAATATCACGACGGGCTGTGCTGAACACTG CAGCTTGAATGAGAATATCACTGTCCCAGACACCAA AGTTAATTTCTATGCCTGGAAGAGGATGGAGGTCGG GCAGCAGGCCGTAGAAGTCTGGCAGGGCCTGGCCCT GCTGTCGGAAGCTGTCCTGCGGGGCCAGGCCCTGTT GGTCAACTCTTCCCAGCCGTGGGAGCCCCTGCAGCT GCATGTGGATAAAGCCGTCAGTGGCCTTCGCAGCCT CACCACTCTGCTTCGGGCTCTGGGAGCCCAGAAGGA AGCCATCTCCCCTCCAGATGCGGCCTCAGCTGCTCC ACTCCGAACAATCACTGCTGACACTTTCCGCAAACT CTTCCGAGTCTACTCCAATTTCCTCCGGGGAAAGCT GAAGCTGTACACAGGGGAGGCCTGCAGGACAGGGA CAGATGACCAGGTGTGTCCACCTGGGCATATCCACC ACCTCCTCACCAACATTGCTTGTGCCACACCCTCC CCCGCCACTCCTGAACCCCGTCGAGGGGCTCTCAGC TCAGCGCCAGCCTGTCCCATGGACACTCCAGTGCCA GCAATGACATCTCAGGGGCCAGAGGAACTGTCCAGA GAGCAACTCTGAGATCTAAGGATGTCACAGGGCCAA CTTGAGGGCCCAGAGCAGGAAGCATTCAGAGAGCAG CTTTAAACTCAGGGACAGAGCCATGCTGGGAAGACG CCTGAGCTCACTCGGCACCCTGCAAAATTTGATGCC AGGACACGCTTTGGAGGCGATTTACCTGTTTTCGCA CCTACCATCAGGGACAGGATGACCTGGATAACTTAG GTGGCAAGCTGTGACTTCTCCAGGTCTCACGGGCAT GGGCACTCCCTTGGTGGCAAGAGCCCCCTTGACACC GGGGTGGTGGGAACCATGAAGACAGGATGGGGGCTG GCCTCTGGCTCTCATGGGGTCCAAGTTTTGTGTATT |

TABLE 1-continued

Exemplary RNA and amino acid sequences.

| Name | SEQ ID NO | Sequence |
|---|---|---|
| | | CTTCAACCTCATTGACAAGAACTGAAACCACCAAAA AAAAAAAA |
| Human erythropoietin (mRNA, coding region) | 3 | ATGGGGGTGCACGAATGTCCTGCCTGGCTGTGGCTT CTCCTGTCCCTGCTGTCGCTCCCTCTGGGCCTCCCA GTCCTGGGCGCCCCACCACGCCTCATCTGTGACAGC CGAGTCCTGGAGAGGTACCTCTTGGAGGCCAAGGAG GCCGAGAATATCACGACGGGCTGTGCTGAACACTGC AGCTTGAATGAGAATATCACTGTCCCAGACACCAAA GTTAATTTCTATGCCTGGAAGAGGATGGAGGTCGGG CAGCAGGCCGTAGAAGTCTGGCAGGGCCTGGCCCTG CTGTCGGAAGCTGTCCTGCGGGGCCAGGCCCTGTTG GTCAACTCTTCCCAGCCGTGGGAGCCCCTGCAGCTG CATGTGGATAAAGCCGTCAGTGGCCTTCGCAGCCTC ACCACTCTGCTTCGGGCTCTGGGAGCCCAGAAGGAA GCCATCTCCCCTCCAGATGCGGCCTCAGCTGCTCCA CTCCGAACAATCACTGCTGACACTTTCCGCAAACTC TTCCGAGTCTACTCCAATTTCCTCCGGGGAAAGCTG AAGCTGTACACAGGGGAGGCCTGCAGGACAGGGGAC AGATGA |

As used herein, the term "low molecular weight" when describing a modified RNA refers to an RNA molecule less than about 750, less than about 650, less than about 550, less than about 450, less than about 350, less than about 250, or less than about 150 nucleotides in length.

As used herein, the term "high molecular weight" when describing a modified RNA refers to an RNA molecule greater than about 550, greater than about 650, greater than about 750, greater than about 850, greater than about 950, greater than about 1000, greater than about 1500, or greater than about 2000 nucleotides in length. An exemplary high molecular weight RNA is human erythropoietin mRNA (SEQ ID NO:2; coding region, SEQ ID NO:3), as described and exemplified herein.

As used herein, the term "exogenous" refers to a substance or molecule originating or produced outside of a cell or organism. In some embodiments, the modified RNA delivered to a cell or administered to a subject is an exogenous RNA (e.g., an exogenous mRNA).

In some embodiments, the LNP and/or the exosome comprises a plurality of modified RNAs (e.g., mRNAs). In some embodiments, the LNP and/or the exosome comprises one or more modified RNAs (e.g., mRNAs) that encode a polypeptide or protein of interest.

In some embodiments, the LNP and/or the exosome comprises an ionizable lipid:modified RNA nucleotides molar ratio of about 1:1 to about 4:1, or about 4:1, about 3:1, about 2:1, about 1.1, or less than about 1:1. In some embodiments, the LNP and/or the exosome comprises an ionizable lipid:modified RNA nucleotides molar ratio of about 1:1. In some embodiments, the LNP and/or the exosome comprises an ionizable lipid:modified RNA nucleotides molar ratio of less than about 1:1, e.g., about 0.1:1, about 0.2:1, about 0.3:1, about 0.4:1, about 0.5:1, about 0.6:1, about 0.7:1, about 0.8:1, or about 0.9:1. As used herein, the phrase "ionizable lipid:modified RNA nucleotides molar ratio" refers to the approximate molar ratio of ionizable lipid to modified RNA nucleotides in the LNPs and/or exosomes disclosed herein.

In some embodiments, the LNP comprises an ionizable lipid:modified RNA nucleotides molar ratio of about 2:1 to about 4:1, or about 4:1, about 3:1, or about 2:1. In some embodiments, the LNP comprises an ionizable lipid:modified RNA nucleotides molar ratio of about 3:1. In some embodiments, the exosome comprises an ionizable lipid:modified RNA nucleotides molar ratio of about 1:1 to about 3:1, or about 3:1, about 2:1, about 1:1, or less than about 1:1. In some embodiments, the exosome comprises an ionizable lipid:modified RNA nucleotides molar ratio of about 1:1 or less than about 1:1. In some embodiments, the exosome comprises an ionizable lipid:modified RNA nucleotides molar ratio that is less than the ionizable lipid:modified RNA nucleotides molar ratio comprised by the LNP. In some embodiments, the exosome comprises an ionizable lipid:modified RNA nucleotides molar ratio of about 1:1 or less than about 1:1, and the LNP comprises an ionizable lipid:modified RNA nucleotides molar ratio of about 3:1. In some embodiments, the exosome comprising an ionizable lipid:modified RNA nucleotides molar ratio of about 1:1 or less than about 1:1 may be non-toxic or less toxic in host cells and tissues, as compared to the LNP or another alternate delivery vehicle comprising an ionizable lipid:modified RNA nucleotides molar ratio greater than about 1:1. In some embodiments, the exosome and the LNP or alternate delivery vehicle comprise the same ionizable lipid (e.g., DLin-MC3-DMA or DLin-DMA) and the same modified RNA nucleotides, but comprise different ionizable lipid:modified RNA nucleotides molar ratios. In some embodiments, modified RNAs and/or exosomes that are neutrally charged (i.e., comprise an ionizable lipid:modified RNA nucleotides molar ratio of about 1:1) are capable of crossing the endosomal membrane, whereas modified RNAs and/or LNPs that are positively charged (i.e., comprise an ionizable lipid:modified RNA nucleotides molar ratio greater than about 1:1) are not capable of crossing the endosomal membrane.

Compositions

In various embodiments, the present disclosure provides pharmaceutical compositions comprising at least one exosome (e.g., any of the exosomes described herein). In some embodiments, the pharmaceutical compositions comprise a plurality of exosomes. The term "pharmaceutical composition," as used herein, refers to a preparation of at least one exosome in addition to other components suitable for administration to a subject, such as a pharmaceutically acceptable carrier and/or excipient. The pharmaceutical compositions provided herein are in such form as to permit administration and subsequently provide the intended biological activity of the active ingredient(s) and/or to achieve a therapeutic effect. The pharmaceutical compositions provided herein preferably contain no additional components which are unacceptably toxic to a subject to which the formulation would be administered.

The phrase "pharmaceutically acceptable" is employed herein to refer to compounds, materials, compositions, and/or dosage forms which are, within the scope of sound medical judgment, suitable for use in contact with the tissues of humans and animals without excessive toxicity, irritation, allergic response, or other problem or complication, commensurate with a reasonable benefit/risk ratio. Drug-approval agencies (e.g., EMA, US-FDA) provide guidance and approve pharmaceutically acceptable compounds, materials, compositions, and/or dosage forms.

As used herein, the term "pharmaceutically acceptable carrier" refers to a carrier or a diluent that does not cause significant irritation to a subject and does not abrogate the biological activity and properties of the administered exosomes in the composition. Pharmaceutically acceptable carriers may enhance or stabilize the composition or can be used to facilitate preparation of the composition. Pharmaceutically acceptable carriers can include solvents, dispersion media, coatings, antibacterial and antifungal agents, isotonic and absorption delaying agents, and the like that are physiologically compatible. The carrier may be selected to minimize adverse side effects in the subject, and/or to minimize degradation of the active ingredient(s). An adjuvant may also be included in any of these formulations.

As used herein, the term "pharmaceutically acceptable excipient" refers to an inert substance added to a pharmaceutical composition to further facilitate administration of an active ingredient. Formulations for parenteral administration can, for example, contain excipients such as sterile water or saline, polyalkylene glycols such as polyethylene glycol, vegetable oils, or hydrogenated napthalenes. Other exemplary excipients include, but are not limited to, calcium bicarbonate, calcium phosphate, various sugars and types of starch, cellulose derivatives, gelatin, ethylene-vinyl acetate co-polymer particles, and surfactants, including, for example, polysorbate 20.

A pharmaceutical composition of the present disclosure can be administered by a variety of methods known in the art. The route and/or mode of administration may vary depending upon the desired results. In some embodiments, the administration is intravitreal, intravenous, intramuscular, intraperitoneal, or subcutaneous. The pharmaceutically acceptable carrier should be suitable for intravitreal, intravenous, intramuscular, subcutaneous, parenteral, spinal or epidermal administration (e.g., by injection or infusion). In some embodiments, a pharmaceutical composition comprising at least one exosome and a pharmaceutically acceptable carrier or excipient may be in a form suitable for parenteral administration. In some embodiments, the pharmaceutical composition may be in the form of a sterile injectable aqueous or suspension, which may be formulated according to known procedures. A sterile injectable preparation may also be a sterile injectable suspension in a non-toxic parenterally acceptable buffer.

The amount of modified RNA in the exosomes and/or the number of exosomes comprising a modified RNA combined with one or more carriers or excipients to produce a single dosage form will necessarily vary depending upon the subject treated and the particular route of administration. Typically, a therapeutically effective amount or efficacious dose of the modified RNA and/or the exosomes comprising a modified RNA is employed in the pharmaceutical compositions of the present disclosure. The exosomes comprising a modified RNA may be formulated into pharmaceutically acceptable dosage forms by conventional methods known to those of skill in the art.

Dosage regimens for exosomes may be adjusted to provide the optimum desired response (e.g., a therapeutic response). For example, a single bolus of exosomes may be administered at one time, several divided doses may be administered over a predetermined period of time, or the dose may be proportionally reduced or increased as indicated by the exigencies of the therapeutic situation. For any particular subject, specific dosage regimens may be adjusted over time according to the individual's need, and the professional judgment of the treating clinician. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active ingredient(s) (i.e., exosomes) calculated to produce the desired therapeutic effect in association with the required pharmaceutical carrier.

Dosage values for compositions comprising at least one exosome may be selected based on the unique characteristics of the active ingredient(s), and the particular therapeutic effect to be achieved. A physician or veterinarian can start doses of the exosomes or pharmaceutical compositions of the disclosure at levels lower than that required to achieve the desired therapeutic effect and gradually increase the dosage until the desired effect is achieved. In general, effective doses of the exosomes or pharmaceutical compositions of the disclosure, for the treatment of a disorder may vary depending upon many different factors, including means of administration, target site, physiological state of the patient, whether the patient is human or an animal, other medications administered, and whether treatment is prophylactic or therapeutic. The selected dosage level may also depend upon a variety of pharmacokinetic factors including the activity of the particular exosomes or pharmaceutical compositions employed, the route of administration, the time of administration, the rate of excretion, the duration of the treatment, other drugs, compounds and/or materials used in combination with the particular exosomes or pharmaceutical compositions employed, the age, sex, weight, condition, general health and prior medical history of the patient being treated, and like factors. Treatment dosages may be titrated to optimize safety and efficacy.

Toxicity and therapeutic efficacy of the exosomes and pharmaceutical compositions provided herein can be determined by standard pharmaceutical procedures in cell culture or in animal models. For example, LD50, ED50, EC50, and 1050 may be determined, and the dose ratio between toxic and therapeutic effects (LD50/ED50) may be calculated as the therapeutic index. The data obtained from in vitro and in vivo assays can be used in estimating or formulating a range of dosage for use in humans.

In various embodiments, kits for use in the therapeutic applications described herein are also within the scope of the present disclosure. In various embodiments, the present disclosure provides a kit comprising at least one exosome. In various embodiments, the kit comprises a plurality of exosomes. In various embodiments, the kit further comprises one or more additional components, including but not limited to: instructions for use; other reagents, e.g., a second therapeutic agent; devices, containers, or other materials for preparing the exosomes for administration; pharmaceutically acceptable carriers; and devices, containers, or other materials for administering the exosomes to a subject. Instructions for use, either as inserts or labels, can include guidance for therapeutic applications including suggested dosages and/or modes of administration. In various embodiments, the kit comprises an effective amount of an exosome or pharmaceutical composition comprising at least one exosome (e.g., any of the exosomes or pharmaceutical compositions described herein), and instructions for using the exosome or pharmaceutical composition to treat or prevent a disorder.

Methods

In various embodiments, the present disclosure provides a method of delivering a modified RNA to a cell by contacting the cell with an effective amount of an exosome or pharmaceutical composition comprising at least one exosome (e.g., any of the exosomes or pharmaceutical compositions described herein), thereby delivering the modified RNA to the cell.

The present disclosure further provides, in various embodiments, a use of an effective amount of an exosome or pharmaceutical composition comprising at least one exosome (e.g., any of the exosomes or pharmaceutical compositions described herein) in delivering a modified RNA to a cell.

As used herein, the term "delivering" means providing an entity to a destination. For example, in some embodiments, delivering a modified RNA to a cell may involve contacting the cell with at least one exosome containing the modified RNA or a pharmaceutical composition comprising at least one exosome containing the modified RNA. In some embodiments, delivering a modified RNA to a subject may involve administering at least one exosome containing the modified RNA or a pharmaceutical composition comprising at least one exosome containing the modified RNA to the subject. Administration of at least one exosome or a pharmaceutical composition comprising at least one exosome to mammalian tissue or to a subject may involve contacting one or more cells with the exosome(s) or pharmaceutical composition.

As used herein, the term "administering" refers to the placement of at least one exosome and/or a pharmaceutical composition comprising at least one exosome into a mammalian tissue or into a subject by a method or route that results in at least partial localization of the exosome(s) and/or pharmaceutical composition components at a desired site or tissue location.

The terms "subject" and "patient" are used interchangeably herein to refer to any human or non-human animal to whom treatment, including prophylactic treatment, with methods and compositions described herein, is provided. For treatment of conditions or disease states which are specific for a specific animal such as a human subject, the term "subject" refers to that specific animal. Non-human animals include all vertebrates (e.g., mammals and non-mammals) such as any mammal. Non-limiting examples of mammals include humans, mice, rats, rabbits, dogs, monkeys, and pigs. In some embodiments, the subject is a human.

In some embodiments, contacting the cell with an effective amount of an exosome or pharmaceutical composition comprises adding the exosomes or pharmaceutical composition to an in vitro cell culture or administering the exosomes or pharmaceutical composition to a subject.

In some embodiments, the cell is present in an in vitro cell culture. In some embodiments, the cell is obtained from a subject. In some embodiments, the cell is present in a subject. In some embodiments, the cell is an epithelial cell, an immune cell, a progenitor cell, or a stem cell. In some embodiments, the cell is a B-lymphocyte, a T-lymphocyte, or a monocyte.

In some embodiments, delivering the modified RNA to the cell does not alter cell generation time. In other embodiments, delivering the modified RNA to the cell does alter cell generation time. In some embodiments, delivering the modified RNA to the cell does not alter total cell protein content by weight. In other embodiments, delivering the modified RNA to the cell does alter total cell protein content by weight.

In various other embodiments, the present disclosure also provides therapeutic methods and uses for the exosomes and pharmaceutical compositions disclosed herein, e.g., in treating a disorder. In some embodiments, the exosomes are isolated from a cell obtained from a subject that has a disorder and/or is in need of treatment.

For instance, in certain aspects, the present disclosure provides a method of treating or preventing a disorder in a subject by administering to the subject an effective amount of an exosome or pharmaceutical composition comprising at least one exosome (e.g., any of the exosomes or pharmaceutical compositions described herein), wherein the exosomes comprise a modified RNA effective to treat the disorder.

In certain other aspects, the present disclosure provides a use of an effective amount of an exosome or pharmaceutical composition comprising at least one exosome (e.g., any of the exosomes or pharmaceutical compositions described herein) in treating or preventing a disorder in a subject, wherein the exosomes comprise a modified RNA effective to treat the disorder.

In certain other aspects, the present disclosure provides a method of treating or preventing a disorder in a subject by (a) providing one or more cells obtained from the subject; (b) contacting the one or more cells with one or more lipid nanoparticles (LNP) comprising a modified RNA under conditions that allow LNP uptake by the cell; (c) isolating exosomes produced by the one or more cells, wherein at least one isolated exosome comprises the modified RNA; and (d) administering to the subject an effective amount of the isolated exosome, wherein the modified RNA is effective to treat the disorder. In some embodiments, the cell is an epithelial cell, an immune cell, a progenitor cell, or a stem cell. In some embodiments, the cell is a B-lymphocyte, a T-lymphocyte, or a monocyte.

As used herein, the term "treat" and its cognates refer to an amelioration of a disease, disorder, or condition (e.g., anemia, myelodysplasia, an immune or inflammatory disease, a monogenetic disorder (e.g., a neurodegenerative disease), or a complex disease (e.g., a myocardial infarction or a cancer)), or at least one discernible symptom thereof. In some embodiments, "treat" refers to an amelioration of at least one measurable physical parameter, not necessarily discernible by the patient. In some embodiments, "treat" refers to inhibiting the progression of a disease, disorder, or condition, either physically (e.g., stabilization of a discernible symptom), physiologically (e.g., stabilization of a physical parameter), or both. In some embodiments, "treat" refers to slowing the progression or reversing the progression of a disease, disorder, or condition. As used herein, "treat" and its cognates also encompass delaying the onset or reducing the risk of acquiring a given disease, disorder, or condition.

The terms "disease" or "disorder" are used interchangeably herein, and refer to any alteration in state of the body or of some of the organs, interrupting or disturbing the performance of the functions and/or causing symptoms such as discomfort, dysfunction, distress, or even death to the person afflicted or those in contact with a person. A disease or disorder can also relate to a distemper, ailing, ailment, malady, sickness, illness, complaint, indisposition, or affection. In some embodiments, the disorder is selected from anemia, myelodysplasia, an immune or inflammatory disease, a monogenetic disorder (e.g., a neurodegenerative disease), and a complex disease (e.g., a myocardial infarction or a cancer). In some embodiments, the disorder is anemia. In some embodiments, the disorder is myelodysplasia. In some embodiments, the disorder is inflammatory bowel disease. In some embodiments, the modified RNA encodes an erythropoietin polypeptide. In some embodiments, the modified RNA encodes a human erythropoietin polypeptide. In some embodiments, the modified RNA encodes an erythropoietin polypeptide of SEQ ID NO:1.

The term "effective amount" as used herein refers to the number of exosomes comprising a modified RNA or the amount of a pharmaceutical composition comprising exosomes comprising a modified RNA sufficient to reduce at least one or more symptom(s) of the disease or disorder, or to provide the desired effect. For example, it can be the amount that induces a therapeutically significant reduction in a symptom or clinical marker associated with wound healing. The term "effective amount" in the context of an exosome or a pharmaceutical composition comprising at least one exosome refers to the amount of exosome or pharmaceutical composition sufficient to deliver a modified RNA and modulate protein expression in a target tissue and/or cell type. In some embodiments, an effective amount of an exosome or a pharmaceutical composition is the amount sufficient to treat a disease or disorder associated with the protein expressed by the modified RNA.

In some embodiments, the exosomes and pharmaceutical compositions disclosed herein may reduce and/or inhibit the expression or activity of at least one biomarker or symptom of an immune response, e.g., an immune response observed with an alternate treatment (e.g., LNPs). In some embodiments, the therapeutic methods disclosed herein reduce and/or inhibit the production or amount of pro-inflammatory markers (e.g., cytokines, chemokines), as compared to treatment methods using alternate delivery vehicles (e.g., LNPs). Non-limiting examples of pro-inflammatory markers include cytokines and chemokines, for instance, IL-1, IL-2, IL-3, IL-4, IL-5, IL-6, IL-8, IL-9, IP-10, IL-12 (p40), IL-12 (p70), IL-13, IL-15, IL-16, IL-17, KC, MCP-1, Exotaxin, FGF-basic, G-CSF, GM-CSF, LIF, MIG, MIP-1, MIP-2, MCP-1, INF-γ, INFα2, RANTES, TNFα, and IL-1β.

As used herein, the phrase "reduce and/or inhibit" refers to a change (positive or negative) of about 10, 20, 30, 40, 50, 60, 70, 80, or 90 percent or greater as compared to a control level. The term "control level," as used herein, indicates either an untreated sample or subject, or a sample or subject treated in the absence of an exosome. In some embodiments, a control level is the level of expression or activity (e.g., expression level of one or more pro-inflammatory markers) in a control sample or subject treated in the absence of an exosome.

In some embodiments, the subject has a reduced immune and/or inflammatory response to treatment in the presence of an exosome containing a modified RNA as compared to treatment in the absence of an exosome, or in the absence of an exosome that does not contain a modified RNA. In some embodiments, the reduced immune and/or inflammatory response comprises an increase or decrease in the level of at least one cytokine. In some embodiments, the reduced immune and/or inflammatory response comprises a decrease in the level of at least one cytokine, wherein the cytokine is selected from IL-6, IP-10, RANTES, MCP-1, and KC.

In some embodiments, contacting one or more cells with the LNP is performed in the presence of human serum. In some embodiments, the human serum is present at about 0.5%, about 1%, or about 1.5% by volume. In some embodiments, the human serum is present at about 1% by volume. In some embodiments, contacting one or more cells with the LNP comprises contacting the one or more cells with at least 2, at least 3, or at least 4 different doses of the LNP. In some embodiments, contacting one or more cells with the LNP comprises contacting the one or more cells with at least 3 different doses of the LNP. In some embodiments, isolating exosomes comprises isolating exosomes from a sample of in vitro cell culture medium.

EXAMPLES

The following examples provide illustrative embodiments of the disclosure. One of ordinary skill in the art will recognize the numerous modifications and variations that may be performed without altering the spirit or scope of the disclosure. Such modifications and variations are encompassed within the scope of the disclosure. The examples provided do not in any way limit the disclosure.

I. Materials and Methods

Formulation and characterization of lipid nanoparticles (LNPs)

Two different types of LNPs, namely DLin-MC3-DMA (MC3-LNPs) and DLin-DMA LNPs (DD-LNPs), containing modified hEPO mRNA (858 nucleotides) (5 meC, ψ) (Trilink) were prepared by precipitating the mRNAs with four different lipid components as described previously (Yanez Arteta et al. (2018) PNAS 115(15):E3351-60). The four components comprised an ionizable lipid (DLin-MC3-DMA or DLin-DMA) which is ionizable (cationic) at low pH; two helper lipids (DSPC and cholesterol); and a PEGylated lipid (PEG2000-DMPE). A solution of hEPO mRNA in water was prepared by mixing mRNA dissolved in MilliQ-water, 100 mM Citrate buffer (pH 3), and MilliQ-water to give a solution of 50 mM Citrate. Lipid solutions in ethanol (99.5%) were prepared with a composition of the four lipid components (ionizable lipid:DSPC:cholesterol:PEG2000-DMPE=50:10:38.5:1.5 molar percent) and a total lipid content of 12.5 mM. The mRNA and lipid solutions were mixed in a NanoAssemblr (Precision Nanosystems) microfluidic mixing system at a volume mixing ratio of Aq:EtOH=3:1 and a constant total flow rate of 12 mL/min. At the time of mixing, the ratio between the nitrogen atoms on the ionizable lipid and phosphorus atoms on the mRNA chain was equal to 3.1. If "empty" LNPs were prepared (i.e. LNPs without any mRNA), then the ethanol phase was mixed with only 50 mM Citrate buffer (pH 3). The initial 0.35 mL and the last 0.05 mL of the LNP solution prepared were discarded while the rest of the volume was collected as the sample fraction.

MC3-LNPs and DD-LNPs containing Cyanine 5-EGFP-mRNA (996 nucleotides) (5 meC, ψ) (Trilink) were prepared using the same procedure as above, although instead of hEPO mRNA, Cyanine 5-EGFP-mRNA was incorporated into LNPs.

For the characterization of formulated LNPs, 25 μL of the sample fraction was injected into 975 μL of 10 mM phosphate buffer (pH 7.4) and used to measure the intensity averaged particle size (Z-average) on a Malvern ZetaSizer (ZetaSizer Nano ZS, Malvern Instruments Inc.). The sample fraction was transferred immediately to a Slide-a-lyzer G2 dialysis cassette (10000 MWCO, Thermo Fischer Scientific) and dialyzed overnight at 4° C. against PBS (pH 7.4). The volume of the PBS buffer was 650-800× the sample fraction volume. The sample fraction was then collected. From this volume, 25 μL was injected into 975 μL of 10 mM phosphate buffer (pH 7.4) and the particle size was measured once again (post-dialysis particle size). The final mRNA concentration and encapsulation efficiency (EE) was measured by Quant-it Ribogreen Assay Kit (Thermo Fischer Scientific).

Cell Culturing

Human epithelial HTB-177 (NCI-H460) cell line was purchased from the American Type Culture Collection (ATCC) and cultured as described by ATCC guidelines. RPMI-1640 growth medium (Sigma Aldrich) containing sodium bicarbonate, without sodium pyruvate and HEPES, was supplemented with 10% exosome-depleted fetal bovine serum (FBS) (Sigma Aldrich), 1% of L-glutamine (2 mM) (Thermo Fisher Scientific) and 1% penicillin-streptomycin (10,000 U/mL) (Thermo Fisher Scientific), at 37° C. in the presence of 5% $CO_2$. The heat inactivated FBS was exosome depleted by ultracentrifugation at 120,000×g for 2 hours at 4° C. on an Optima L-100 XP ultracentrifuge with a 70Ti rotor (Beckman Coulter), and exosome depleted supernatant was filtered through 0.2 μm filters.

Fresh buffy coats from healthy donors were obtained from Sahlgrenska University hospital (Gothenburg, Sweden), and peripheral blood mononuclear cells (PBMCs) were isolated by density-gradient centrifugation. PBMCs were cultured in complete RPMI-1640 growth medium supplemented with L-glutamine, non-essential amino acids, sodium pyruvate, 1% penicillin-streptomycin, β-mercaptoethanol, and 10% FBS (exosome-depleted), and stimulated with goat anti-human IgA/IgG/IgM F(ab')2 fragments (2.5 μg/mL; Jackson ImmunoResearch Laboratories, Inc.) and phorbol myristate acetate (PMA) (1 μg/mL; InvivoGen).

mRNA Delivery to Epithelial Cells Via LNPs

Human epithelial (HTB-177) cells were seeded at a density of $3\times10^6$ cells per 175T flask in 30 mL of growth medium and incubated for 24 hours. After the 24 hour incubation period, cells were treated with 1 mL of DD-LNPs or MC3-LNPs containing 100 μg of hEPO mRNA per flask in the presence of 1% human serum (Sigma Aldrich). This 100 μg of hEPO mRNA in 1 mL of LNPs solution was administered in 3 different doses, as follows: day (1) 200 μL LNPs (20 μg mRNA); day (2) 400 μL LNPs (40 μg mRNA); day (3) 400 μL LNPs (40 μg mRNA), and harvested after 96 hours. Cells treated with an equal volume (200 μL, 400 μL, 400 μL) of corresponding empty DD-LNPs or empty MC3-LNPs (i.e., LNPs without mRNA), as well as untreated cells, were used as negative controls.

Isolation and Characterization of Exosome Extracellular Vesicles (EVs)

EVs were isolated from conditioned culture medium of LNP-treated cells and negative controls as described previously (El-Andaloussi et al. (2012) Nat Protoc. 7(12):2112-26). Briefly, to remove cell debris, the cultured medium was centrifuged at 3000×g for 15 min at 4° C. on a 4K15 centrifuge (Sigma). The resultant supernatant was collected and ultracentrifuged at 60,000×g for 35 min at 4° C., followed by filtration through 0.2 μm filters to obtain EVs with diameter below 200 nm. The filtered supernatant was then ultracentrifuged at 120,000×g for 70 min at 4° C. to pellet EVs. The EV pellets were resuspended in an appropriate volume (50-80 μL) of PBS (Sigma Aldrich). All ultracentrifugation steps were performed on an Optima L-100 XP ultracentrifuge using a 70Ti rotor (Beckman Coulter).

EVs were quantified based on their protein concentration. 2 μL of EV suspension, incubated together with 2 μL of M-PER Mammalian Protein Extraction Reagent (Thermo Fischer Scientific), was sonicated on an Ultrasonic cleaner (VWR) for 5 min at 54° C. to generate EV extracts. EV proteins were quantified using a Qubit 2.0 fluorometer (Thermo Fischer Scientific). 1 μL of EVs, 1 μL of Qubit protein reagent, and 198 μL Qubit buffer were mixed and incubated at room temperature for 15 min. Readings were recorded on a Qubit 2.0 fluorometer.

RNA Isolation from EVs and Cells after LNP Administration

Total RNA from EVs and from LNP-treated cells was isolated using miRCURY™ RNA isolation kit—Cell and Plant (Exiqon) according to the manufacturer's instructions. Total RNA was quantified using a Qubit 2.0 fluorometer (Thermo Fisher Scientific). RNA quality (230/260 ratio) was assessed using a NanoDrop 1000 (Thermo Fisher Scientific).

Nanoparticle Tracking Analysis (NTA) for EV Size and Concentration Determination HTB-177 MC3-EVs and untreated EVs were assessed for size (nm) and concentration (particles/mL) using a Nano- Sight LM10 instrument (Malvern Panalytical) equipped with a Hamamatsu C11440-50B/A11893-02 camera. Before analysis, the particles were diluted 500 times in 0.1 µM filtered PBS (Sigma) to reduce the number of particles in the field of view below 180 particles per frame. Three independent measurements (biological replicates) were performed in scatter mode. Measurement readings for each EV sample were taken in 5 captures for 60 seconds each at 25 frames per second (fps) at an adjusted camera level (10-16) and detection threshold (5-15), depending on the individual sample and manual monitoring of temperature. Blur and Max Jump Distance were set to automatic. Readings, the acquisition, and the data analysis were performed using NanoSight Fluorescent NTA LM10 software version 3.3 (Malvern Panalytical).

Detection and qPCR-Based Quantification of LNP-Derived Exogenous hEPO mRNA in EVs The hEPO mRNA in EVs, the lysate of their parental cells after LNP administration, and corresponding negative controls were quantified using quantitative Real-Time PCR (RT-qPCR). Based on RNA yield, 0.25 to 1 µg of total EV RNA and cellular total RNA were converted into cDNA using a high-capacity cDNA kit (Thermo Fisher Scientific). 100 ng of total cDNA was used for hEPO mRNA quantification using TaqMan probe assays on a ViiA™ 7 instrument (Thermo Fisher Scientific) according to the manufacturer's instructions. 2 µg of pure hEPO mRNA (RNA from Trilink) was reverse transcribed, and the resultant cDNA was serially diluted (ten-fold) to prepare seven standards (highest point: 100 ng), which were run in technical triplicate to generate the standard curve. Subsequently, EV cDNA and cellular cDNA was used for hEPO mRNA analysis; absolute quantification was interpolated against the standard curve with minimal $R^2 > 0.975$. GAPDH was used as an internal control. To calculate the molar amount of hEPO mRNA, the following was assumed: 1 mole hEPO mRNA=858 hEPO mRNA nucleotides.

Detection of EV Markers (CD63 and CD9) and Identification of Foreign mRNA in CD63/CD9 Positive EVs HTB-177 cells were treated with MC3-LNPs containing 100 µg of Cy5-mRNA (Trilink) as described above. Untreated cells were included as control. After 96 hours, total EVs were isolated from the culturing medium of LNP treated cells (MC3-EVs) and untreated cells (EVs) by differential ultracentrifugation (pre-enrichment), resuspended in PBS, and quantified. After pre-enrichment, CD63/CD9 positive EVs were isolated using an affinity-based method and evaluated for the presence of Cy5-mRNA by FACS. An Exosome-Human CD63 Isolation/Detection reagent for cell culture medium (Thermo Fisher Scientific) was used to immobilize the CD63 positive EVs to paramagnetic Dynabeads according to the manufacturer's instructions. In the binding reaction, 20 µL of paramagnetic Dynabeads were incubated with 25 µg or 50 µg of total MC3-EVs. As a negative control, 20 µL of paramagnetic Dynabeads were incubated with an equivalent volume of PBS (no EVs). After the immobilization of CD63 positive EVs, the EVs were stained with a mouse anti-human PE-CD9 antibody (BD Pharmingen, Cat. No. 555372) according to the manufacturer's instructions. EVs were acquired on a BD FACSLyric system (BD Biosciences) and CD9 and Cy5-mRNA were detected. Data were analyzed using FlowJo software (Tree-Star Inc.). The experiment was performed in biological duplicate.

Analysis of Direct Transfer of mRNA from LNPs into EVs in the Absence of Cells

LNPs and EVs were directly mixed and incubated (in the absence of cells) at 37° C. using different proportions (amounts) of LNPs and EVs. Two different proportions (amounts) of EVs naïve of any prior treatment were incubated with 300 µL of DD-LNPs or MC3-LNPs (39 µg of hEPO mRNA) for 2 hours in 30 mL of PBS at 37° C. In the first setup, the proportion between EVs and LNPs was 200 µg EVs+300 µL LNPs (1×), whereas in the second setup the proportion was 50 µg EVs+300 µL LNPs (4×). After 2 hours of incubation, EVs were re-isolated by ultracentrifugation, total RNA from EVs was isolated, and hEPO mRNA was quantified by qPCR to evaluate the direct transfer of hEPO mRNA from LNPs into EVs. As a negative control, equivalent volumes of DD-LNPs or MC3-LNPs were incubated in PBS without EVs and ultracentrifuged. As a positive control, cells were administered DD-LNPs or MC3-LNPs containing hEPO mRNA and EVs were isolated (DD-EVs or MC3-EVs, respectively). RNA was isolated and hEPO mRNA was quantified by qPCR. The experiment was performed in biological triplicate. Data are presented as percentage of hEPO mRNA detected in EVs relative to the administered amount of hEPO mRNA delivered by LNPs to cells or amount of hEPO mRNA directly mixed with EVs. Mean values with standard deviation (SD) of replicates are shown.

EV-mRNA Protection Assay

HTB-177 cells were treated with MC3-LNPs containing 100 µg of hEPO mRNA as described above. Untreated cells were included as control. After 96 hours, EVs were isolated and quantified. First, in order to evaluate the efficiency of RNase A activity (Thermo Fisher Scientific), 280 ng of pure hEPO mRNA (Trilink) were incubated with RNase A (0.5 µg/µL) or with an equal volume of PBS at 37° C. for 20 minutes. Next, 200 µg of MC3-EVs were treated with RNase A using the same conditions. As negative controls, 200 µg of MC3-EVs and 150 µg of untreated EVs were incubated in the same conditions except that RNase A was replaced by PBS. After the incubation, total RNA from EVs was isolated using a miRCURY™ RNA Isolation Kit-Cell and Plant (Exiqon). hEPO mRNA was quantified by qPCR to assess the effect of the RNase A on hEPO mRNA content if present outside of EVs. The experiments were performed in biological triplicate.

Analysis of Ionizable Cationic Lipids in EVs by Gradient UPLC

Fractions of EVs were used to examine the presence of LNP-derived ionizable lipids in EVs. 5-10 µL of each EV sample (obtained from MC3-LNP- and DD-LNP-treated cells) was diluted 50 times with PBS and further diluted 1+1 with a mixture of 2% w/v of Triton® X-100 in Tris/EDTA buffer. Samples were incubated at 37° C. for 30 min, and then injected on an Acquity Ultra Performance LC coupled to a Single Quad Detector (SQD) (Waters). The analytical column was a Waters Acquity UPLC® CSH C18, 1.7 µm, 2.1×100 mm kept at 60° C. The flow rate was 0.50 mL/min using a mobile phase of 0.1% formic acid in water (A), and 0.1% formic acid in an equal mixture of acetonitrile and isopropylalcohol (B). A gradient run was applied where 10% B at 0.0 min was increased to 85% B at 1.0 to 5.0 min and kept at 85% B to 7.5 min. A washing step of 99% B at 7.6 min to 9.5 min was included in the gradient run. Then, 10% B was applied for conditioning from 9.6 min to 12.0 min. The elution time for DLin-DMA was 6.3 min and the elution time for DLin-MC3-DMA was 6.5 min, under these conditions. Quantification was determined using external standard solutions of DLin-DMA and DLin-MC3-DMA dissolved in ethanol 99.5%. The SQD was run using electrospray, positive mode, and tuned using auto tune with a solution of DLin-MC3-DMA. Recording of the cationic lipids was made using Single Ion Recording (SIR) at M+1 for each cationic lipid.

Lastly, the molar ratios of ionizable lipids and hEPO mRNA nucleotides (ionizable lipids per hEPO mRNA) were determined in both EVs and LNPs. Experiments were performed in at least six biological replicates.

hEPO Protein Quantification

After LNP treatment, the cell-conditioned supernatant was collected and directly used for hEPO protein detection, whereas total cellular proteins were extracted from cell lysate using 500 µL of M-PER Mammalian Protein Extraction Reagent (Thermo Fisher Scientific) in the presence of 1% halt protease inhibitor cocktail (Thermo Fisher Scientific). Briefly, cells were gently agitated on a three-dimensional Bio-rocker for 10 min at 4° C. and centrifuged at 14,000×g for 10 min to pellet the cell debris. The resultant supernatant (containing proteins) was transferred to a new tube. In parallel, the cultured supernatant was centrifuged at 3000×g for 15 min at 4° C. on a 4K15 centrifuge (Sigma) to remove cell debris. The resultant supernatant was transferred to a new tube. The hEPO protein was also analyzed in EV lysates using an Erythropoietin ELISA Kit (STEM-CELL Technologies), according to the manufacturer's instructions. 2 µL of EV suspension was incubated together with 2 µL of M-PER Mammalian Protein Extraction Reagent (Thermo Fisher Scientific), and was sonicated on an Ultrasonic cleaner (VWR) for 5 min at 54° C. to generate EV extracts. Total cellular proteins and total proteins from cultured supernatant, as well as total EV proteins, were quantified using a Qubit 2.0 fluorometer (Thermo Fisher Scientific) according to the manufacturer's protocol. To detect hEPO protein, the Erythropoietin ELISA Kit (STEM-CELL Technologies) was used according to the manufacturer's instructions. 50 µL of total proteins solution (for both cells and cultured supernatant) was used and hEPO protein levels were calculated according to the relative standard curve as mU/mL. The concentration was converted into fg/mL using the conversion (119 mU=1 ng) and normalized to the total number of cells.

Effect of LNP Administration on Cell Growth, RNA, and Protein Content

To determine the effect of LNPs on cellular behavior and assess cell tolerance against LNP treatment (DD-LNPs or MC3-LNPs), cell generation time (cellular growth), cellular total RNA, total content of intracellular proteins, and total content of secreted proteins were calculated after a treatment period of 96 hours with DD-LNPs or MC3-LNPs. The effect of LNPs on EVs was also examined by quantifying total EV RNA and protein content after treatment with LNPs.

The cell generation time (G) (defined as the time (in hours) to double the population of cells) was calculated based on the difference between the number of cells at the beginning and at the end of the treatment interval (ΔN) using the following formula:

$$G = t/n$$

$$t = LNPs \text{ adminstration interval } (h)$$

$$n = \frac{\log(n.\text{cells post-administration}) - \log(n.\text{cells pre-administration})}{\log 2}$$

The variation of total RNA in cells and in EVs, total protein in EVs, total protein in cells (intracellular), and total protein in cultured supernatants (secreted) were normalized to the corresponding ΔN (change in cell number).

hEPO mRNA Delivery to Human Epithelial (HTB-177) Cells Via EVs

Human epithelial (HTB-177) cells were seeded at a density of 5×10⁶ cells per T175 flask and cultured in RPMI-1640 complete medium. 600 µg of MC3-EVs (700 ng hEPO mRNA) isolated from MC3-LNP-treated cells, and 600 µg of DD-EVs (1100 ng hEPO mRNA) isolated from DD-LNP-treated cells, were dissolved in RPMI-1640 medium and transferred to recipient cells in independent assays over 2 days: day (1) 300 µg of MC3-EVs, and day (2) 300 µg of MC3-EVs in two individual doses of 150 µg each after 8 hours. Similarly, 300 µg of DD-EVs (day 1) and 300 µg (day 2) were transferred to recipient cells in independent assays. Empty EVs (without hEPO mRNA) and EVs from untreated cells were delivered to recipient cells as controls. After 48 hours, cells and cultured supernatant were collected and total RNA was isolated. hEPO mRNA and hEPO protein were evaluated by RT-qPCR and ELISA, respectively, according to protocols described above. The experiment was performed in two independent biological replicates.

Cyanine 5-EGFP-mRNA Delivery to Epithelial and Primary Blood Cells Via EVs 1 mL of DD-LNPs containing fluorescent Cyanine 5 (Cy5)-EGFP-mRNA was delivered to HTB-177 cells in different doses (200 µL, 400 µL, 400 µL) according to the above-mentioned protocol, with the exception that 1 mL of LNPs contained 76 µg of fluorescent Cy5-EGFP-mRNA per flask (in contrast, hEPO mRNA was 100 µg/mL). 96 hours after administration of LNPs, the conditioned medium (supernatant) as well as the parental cells were harvested and analyzed for hEPO mRNA and hEPO protein, or stored for further experiments. Empty DD-LNPs (having no mRNA) and untreated cells were used as controls. HTB-177 cells and immune cells such as B cells, T cells, and monocytes purified from peripheral blood mononuclear cells (PBMCs, isolated from buffy coat as described above) were seeded at a density of 2×10⁵ cells per well, cultured in 200 µL of culturing medium in 96-well round bottom plates, and incubated overnight at 37° C., 5% CO₂. After a 24-hour stimulation of cultured cells, 78 µg of DD-EVs containing Cy5-EGFP-mRNA (Trilink) in 25 µL PBS solution were delivered to recipient cells. For control assays, empty DD-EVs (without EGFP-mRNA) and native EVs (EVs from untreated cells) were delivered to cells or cells were left untreated. After 5 hours, 24 hours, and 48 hours of EV treatment, cells were harvested and stained for surface markers with monoclonal antibodies (mAbs) against CD19 (B cells), CD3 (T cells), and CD14 (monocytes) (Becton-Dickinson Biosciences). Cells were acquired on a FACS-Verse (BD Biosciences). Cy5-EGFP-mRNA was detected based on fluorescence in each cell type, and data were analyzed using FlowJo software (TreeStar Inc.).

Effect of pH on hEPO mRNA Release from LNPs

MC3-LNPs containing hEPO mRNA at a concentration of 0.011 mg/mL were incubated in 10 mM Citric Acid-Na₂HPO₄ buffer solutions with 150 mM NaCl (pH 7.4, 6.6, or 5.8) at 37° C. under quiescent conditions. The total amount of mRNA was measured at time zero using 0.125 mM TritonX-100 (VWR Proteomics Grade) and 0.125 mM Sodium Dodecyl Sulfate (Sigma) in a RiboGreen Assay. To assess the fraction of mRNA released from LNPs at various pH (pH 7.4, 6.6, or 5.8), the free amount of mRNA was analyzed with a Quant-iT RiboGreen RNA Reagent Assay kit (Invitrogen by Thermo Fisher Scientific) using a Perkin Elmer LS55 Luminescence Spectrometer (ex: 480 nm, em: 525 nm).

In Vivo Transfer of hEPO mRNA Via EVs and MC3-LNPs

Experimental procedures were approved (ethical application number 83-2015) by the Regional Laboratory Animal Ethics Committee of Gothenburg, Sweden. All procedures conform to the Swedish Animal Welfare Act and regulations SJVFS 2012: 26. C57BL6/N Crl female mice (n=36), 9-10 weeks of age, were purchased from Charles River Laboratory (Germany) and housed in the animal facility at AstraZeneca, Mölndal, Sweden. Mice were kept in groups of 4 mice per cage under standard conditions (21° C. RT, 12:12 h light-dark cycle, 45-55% humidity) with access to a normal chow diet (R70, Lactamin AB) and water ad libitum. Environmental enrichment was provided (cartons, wooden tongue depressors, and cotton nesting pads). 100 µL of MC3-LNP-derived EVs or MC3-LNPs containing an equal dose of 1.5 µg hEPO mRNA were intravenously injected to mice (n=4 per group). 100 µL of PBS were injected into control mice. Blood samples were collected from groups (n=4) of mice by Vena Saphena microsampling at 2, 5, 24, and 48 hours after injection of EVs and LNPs. Blood samples, collected in 35 µL EDTA-prepped capillary tubes, were centrifuged at 1700×g to collect plasma, which was kept frozen −86° C. until time for analysis. 5, 24, and 96 hours after injection, groups of mice were terminated to collect organs. Mice were sedated, by isoflurane anesthesia, and bled from the orbital sinus, followed by cutting of the heart. Subsequently, entire organs (liver, kidney, spleen, pancreas, heart, thymus, lung, and brain) were collected, snap frozen in liquid nitrogen and stored in −86° C. until time for analysis.

Detection of Human EPO Protein in Mouse Plasma

To analyze hEPO protein in mouse plasma after hEPO mRNA delivery via MC3-LNPs and MC3-EVs, a hEPO assay was developed in-house on the Gyros platform. The capture antibody (3F6, MAIIA Diagnostics) was biotinylated according to kit insert using EZ-Link Sulfo-NHS-LC-Biotin kit (Thermo Fisher Scientific, #21327). The detection antibody (7D3, MAIIA Diagnostics) was Alexa 647 labelled using a monoclonal antibody labeling kit (Thermo Fisher Scientific, #A20186). hEPO protein (in-house) was used to generate a standard curve in Rexxip A buffer (Gyros Protein Technologies), ranging from 12.2 µg/mL to 50 ng/mL. Mouse plasma samples were diluted 1:1 (v:v) in Rexxip A-max buffer (Gyros Protein Technologies) prior to analysis. Samples were analyzed on a Gyrolab Bioaffy 1000 CD (Gyros Protein Technologies) with a Gyrolab instrument (Gyrolab xP workstation, Gyros Protein Technologies). A 5-parametric curve fitting was used for the standard curve. All standards and samples had CVs below 10%.

Detection of Human EPO Protein in Mouse Tissues

Total protein from organs was extracted using M-PER Mammalian Protein Extraction Reagent (Thermo Fisher Scientific) in the presence of 1% halt protease inhibitor cocktail (Thermo Fisher Scientific), according to the manufacturer's instructions. Briefly, 20-70 mg of tissue was lysed in 200-350 µL of lysis buffer (depending on tissue weight) with the addition of protease inhibitors (Thermo Fisher Scientific) in a Tissue Lyser II (Qiagen) for 3-5 min at maximum speed (30 Hz), and centrifuged at 10,000×g for 15 min at 4° C. to get rid of any tissue debris. Resultant supernatant was used for protein quantification using a Qubit 2.0 fluorometer (Thermo Fisher Scientific). 50 µL of total protein were analyzed for hEPO protein detection using Erythropoietin ELISA Kit (STEMCELL Technologies) according to the manufacturer's instructions. The amount of hEPO protein (ng) in each organ was normalized to the relative organ weight (g).

Cytokine Analysis in Mouse Plasma

After intravenous administration of MC3-LNPs and MC3-EVs, plasma concentrations of mouse cytokines were measured by EMD Millipore's MILLIPLEX® MAP Mouse Cytokine magnetic bead kit (Merck KGaA, #MCY-TOMAG-70K) for simultaneous quantification of IL-6, KC, MCP-1, RANTES, TNFα, IFN-γ, IL-1β, and IP-10. The sample was first diluted 1:2 with assay buffer, then together with standards and quality controls placed in a 96-well plate. A solution containing beads was added; beads are magnetic microspheres coated with a specific antibody. The mixture was incubated overnight at 4° C., then incubated with Streptavidin-PE conjugate to complete the reaction on the surface of each microsphere. The plate was read on an analyzer Bio Rad Luminex 200®. Each individual microsphere was identified and the result of its bioassay was quantified based on fluorescent reporter signals. The concentration was measured using Median Fluorescent Intensity (MFI) data using a 5-parameter logistic curve-fitting method.

Detection of Human EPO mRNA in Mouse Organs

Total RNA from mouse organs was isolated using the RNeasy kit (Qiagen) according to the manufacturer's recommendations. 10-50 mg of tissue were lysed in RLT buffer (600 µL) in a Tissue Lyser II (Qiagen) for 3-4 min at maximum speed (30 Hz), and centrifuged at 10,000×g for 3 min at 20° C. to get rid of any tissue debris. Subsequently, the supernatant was transferred to columns and further processed. RNA was quantified using a Qubit 2.0 fluorometer (Thermo Fisher Scientific) and RNA quality was assessed using a NanoDrop 1000 (Thermo Fisher Scientific). Based on RNA yield, between 0.5 and 1 µg of total RNA was retro-transcribed into cDNA, and 100 ng was used to detect hEPO mRNA using RT-qPCR according to the above-mentioned protocol. The amount of hEPO mRNA in each organ (µg) was normalized to the relative organ weight (g).

Statistical Analysis

For all experiments, statistical analyses were performed using GraphPad Prism v.7 (GraphPad). The in vitro data were analyzed by using an unpaired two-tailed Student's t test, except for the effects of LNP administration on HTB-177 growth, RNA content, and protein content, which were analyzed using a one-way ANOVA followed by a Tukey's multiple comparisons test (significant P-value <0.05). The hEPO content in mouse plasma and organs was analyzed using an unpaired two-tailed Student's t test, while the levels of cytokines in mouse plasma were analyzed using a one-way ANOVA followed by a Sidak's multiple comparisons test. The level of significance of p-values were indicated as follows: *$p<0.05$, $p<0.01$, *$p<0.001$, and ****$p<0.0001$.

II. RESULTS

Example 1: Characterization of Lipid Nanoparticles (LNPs)

The LNPs used in the experiments described herein were comprised of five major components, namely ionizable lipid (DLin-MC3-DMA or DLin-DMA), DSPC (1,2-distearoyl-sn-glycero-3-phosphocholine), cholesterol, PEGylated lipid (PEG2000-DMPE), and mRNA (hEPO mRNA). LNPs containing DLin-MC3-DMA ionizable lipids are referred to as MC3-LNPs; LNPs containing DLin-DMA ionizable lipids are referred to as DD-LNPs. Both LNP formulations were characterized with respect to several biophysical parameters, including loading efficiency, average size, polydispersity index (PDI), and molar percentage ratio between individual LNP components (Table 2). Data are presented as mean±standard error of the mean (SEM) in Table 2 (MC3-LNPs, n=4; DD-LNPs, n=9).

Figure 8A:
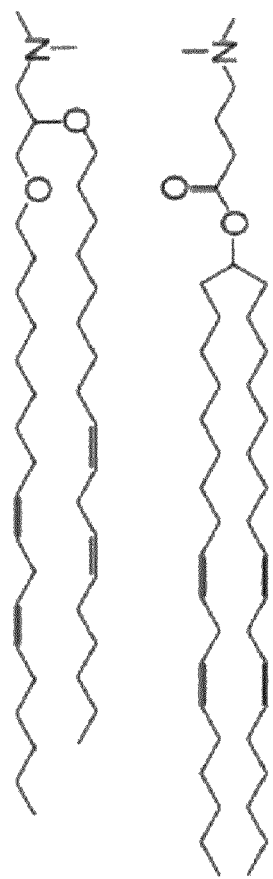
FIG. 8A shows structures of exemplary lipid nanoparticles (LNPs) with two different ionizable lipids, DLin-MC3-DMA and DLin-DMA.

The loading efficiencies of hEPO mRNA constructs in LNPs (defined as encapsulation efficiency (% EE)) ranged between 93-97%. The average measured size of LNPs containing mRNA constructs ranged between 82-90 nm. The concentration of hEPO mRNA constructs in LNPs was 0.1 mg (100 µg). The molar percentage ratio between individual components in the LNPs was 50:10:38.5:1.5 (DLin-DMA: DSPC:cholesterol:PEG2000-DMPE) and 50:10:38.5:1.5 (DLin-MC3-DMA:DSPC:cholesterol:PEG2000-DMPE). The structures of exemplary LNPs with two different ionizable lipids, DLin-DMA and DLin-MC3, are shown in FIG. 8A.

Pharm Biopharm. 79(1):150-61). Nanoparticles may also induce autophagic-lysosomal activation as a result of their chemical composition and/or mRNA content (Klionsky et al. (2016) Autophagy 12(1):1-222; Mizushima et al. (2011) Annu Rev Cell Dev Biol. 27:107-32; Yang and Klionsky (2010) Nat Cell Biol. 12(9):814-22; Zabirnyk et al. (2007) Autophagy 3(3):278-81).

Figure 8B:
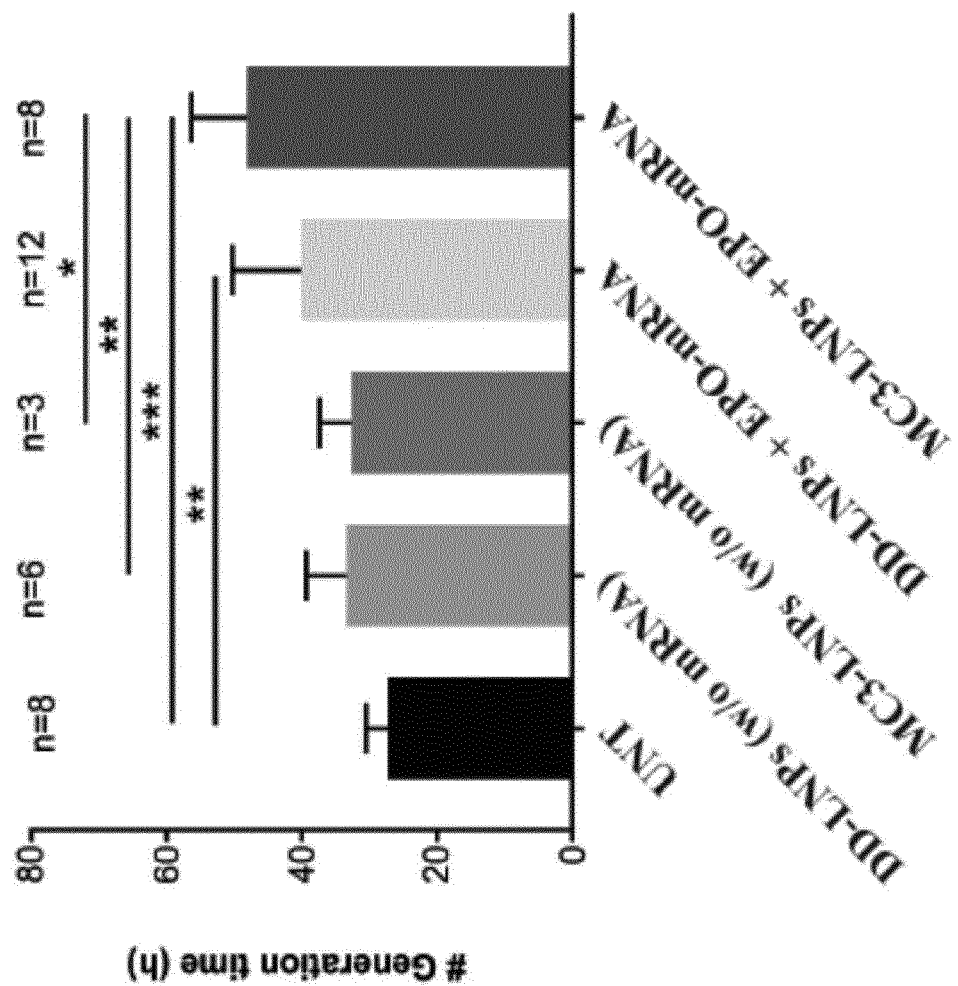
FIG. 8B shows the effect of LNPs on cell growth. DD-LNPs or MC3-LNPs, each containing 100 µg of hEPO mRNA, were transferred to recipient cells in independent experiments. Cells were also treated with control LNPs without hEPO mRNA. After 96 hours of LNP treatment, cells were harvested, counted, and the cell generation time (i.e., the time (in hours) to double the population of cells) was calculated based on the difference between the number of cells at the beginning and at the end of the LNP treatment interval (defined as ΔN (change in cell number)). The number (n) represents biological replicates assessed for each treatment. Significant difference between each group was assessed by using a one-way ANOVA test, followed by a Tukey multiple comparisons test (significant P-value<0.05). Only significant P-values are shown: *P<0.05, P<0.01, *P<0.001, ****P<0.0001.

To determine whether DD-LNPs or MC3-LNPs may affect cellular growth, total RNA synthesis, and/or protein production, HTB-177 epithelial cells were harvested after treating the cells with the LNPs for 96 hours. Following harvest, cells were counted and the generation time (i.e., the time (in hours) to double the population of cells) was calculated. Cell generation time was significantly increased after LNP treatment, particularly treatment with LNPs containing hEPO mRNA (FIG. 8B). This suggests that cells may grow at a slower rate when they receive LNPs with hEPO mRNA, as compared to when they receive empty LNPs (without hEPO mRNA) or when they receive no LNPs (untreated cells).

TABLE 2

Biophysical characteristics of exemplary lipid nanoparticles.*

| Ionizable lipid | Size (nm)** | PDI | mRNA Concentration (mg/mL) | Lipid Concentration (mg/mL) | EE (%) |
|---|---|---|---|---|---|
| DLin-DMA | 88 ± 4 | 0.1 ± 0.01 | 0.1 ± 0.002 | 0.97 ± 0.029 | 94 ± 1.3 |
| DLin-MC3 | 84 ± 2 | 0.08 ± 0.02 | 0.1 ± 0.002 | 1.02 ± 0.026 | 97 ± 0.2 |

*Abbreviations: PDI—polydispersity index; EE (%)—encapsulation efficiency of mRNA into LNPs.
**Size (nm) is given as the Z-average diameter.

Example 2: Delivery of hEPO mRNA to Cells Via LNPs

The delivery of mRNA encoding human erythropoietin (hEPO protein) to cells via two different formulations of LNPs was investigated. The efficacy of mRNA delivery via DLin-DMA-LNPs (designated as DD-LNPs) and DLin-MC3-LNPs (designated as MC3-LNPs) was examined by determining the amount of intracellular hEPO mRNA, as well as the amount of hEPO protein produced in both the intracellular and extracellular environment.

Figure 1B:
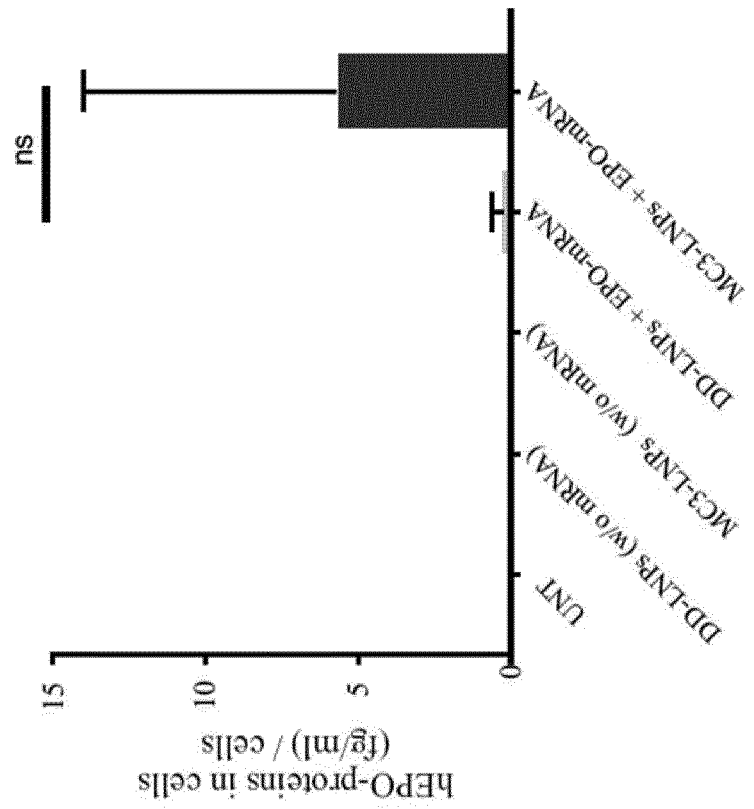
FIG. 1B shows the intracellular amount of hEPO protein detected in HTB-177 cells after LNP delivery. 100 µg of hEPO mRNA was delivered to HTB-177 cells via LNPs. After 96 hours of LNP treatment, the hEPO protein from exogenously delivered mRNA was quantified in recipient cells by ELISA. The amount of hEPO protein was normalized to the total number of harvested cells after 96 hours of LNP treatment.
Figure 1C:
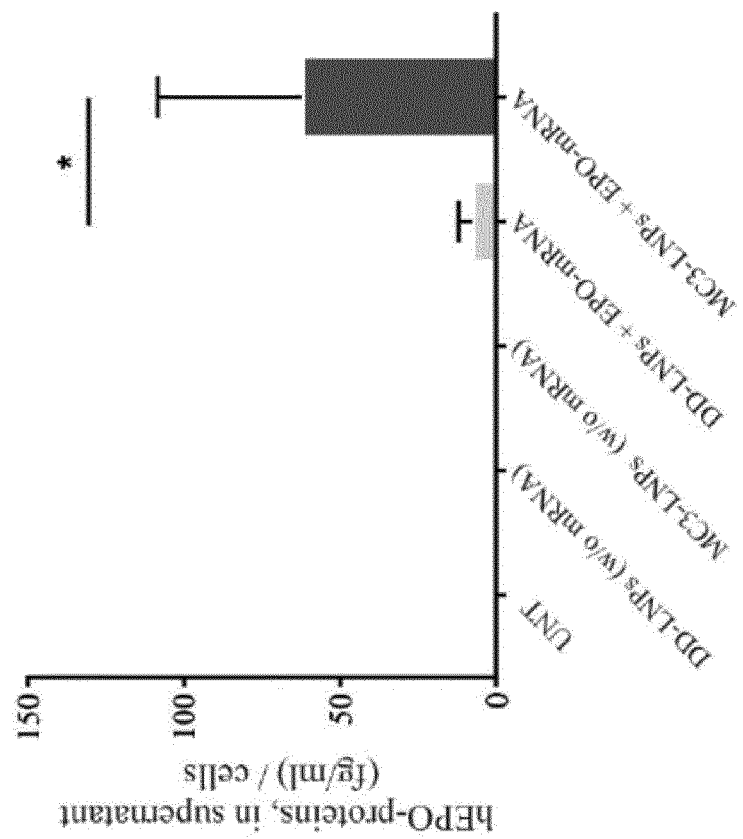
FIG. 1C shows the extracellular amount of hEPO protein detected in supernatants of HTB-177 cell conditioned media after LNP delivery. 100 µg of hEPO mRNA was delivered to HTB-177 cells via LNPs. After 96 hours of LNP treatment, the secreted hEPO protein was quantified in supernatants of cell culture conditioned media using ELISA. The amount of hEPO protein was normalized to the total number of harvested cells after 96 hours of LNP treatment.

100 µg of hEPO mRNA was transferred to human epithelial (HTB-177) cells via DD-LNPs or MC3-LNPs in independent experiments. After 96 hours of LNP treatment, hEPO mRNA was quantified in the lysates of recipient cells. hEPO protein was also quantified in the lysates of recipient cells, as well as in the supernatant of the cell-cultured medium. Both formulations of LNPs were capable of delivering hEPO mRNA to cells (FIG. 1A). Both formulation of LNPs also resulted in the production of hEPO protein from exogenously delivered mRNA, which the recipient cells lack (FIG. 1B and FIG. 1C). MC3-LNPs delivered significantly higher amounts of hEPO mRNA to cells, as compared to DD-LNPs. Likewise, significantly higher amounts of hEPO protein were observed following MC3-LNP delivery relative to DD-LNP delivery. Higher amounts of hEPO protein, which has been characterized as a secretory protein (Bettan et al. (2000) Mol Ther. 2(3):204-10; Shapir et al. (2015) Hum Gene Ther Clin Dev. 26(4):216-27), were detected in the extracellular fractions (FIG. 1C) as compared to the cytosol (FIG. 1B).

Figure 8C:
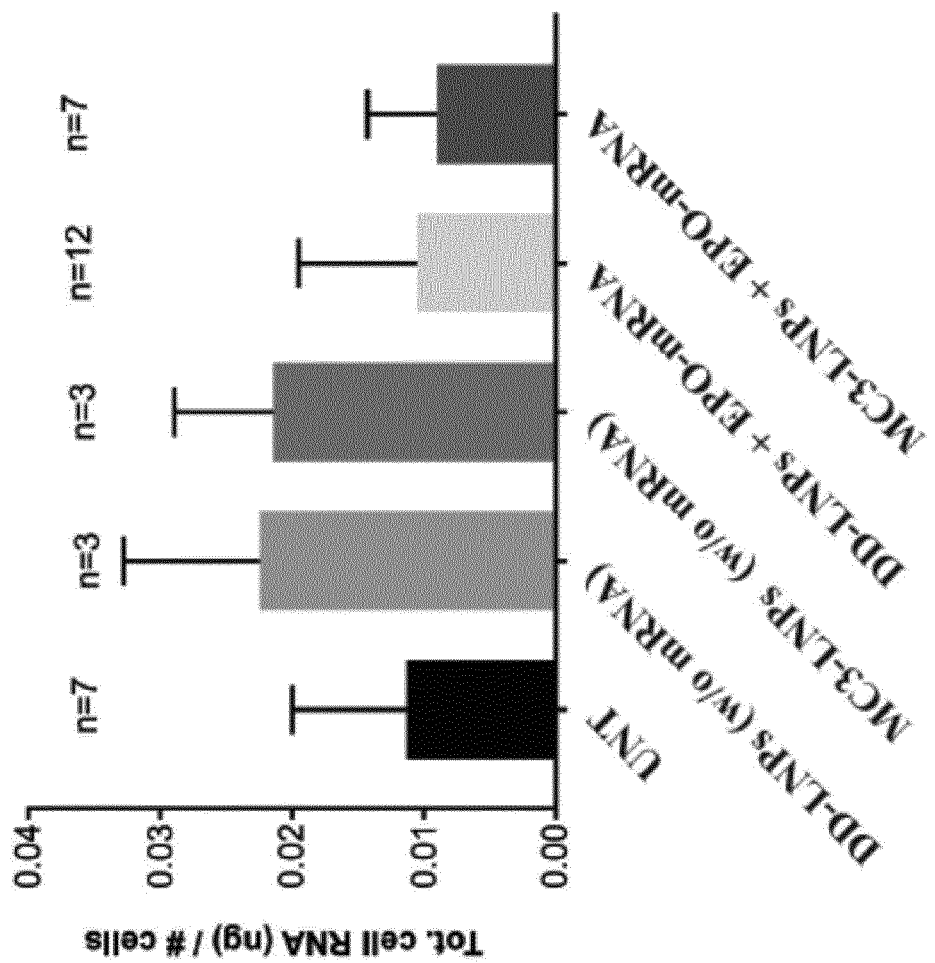
FIG. 8C shows the effect of LNPs on total cellular RNA. After 96 hours of LNP treatment, total cellular RNA was quantified and normalized to ΔN. The number (n) represents biological replicates assessed for each treatment. Significant difference between each group was assessed by using a one-way ANOVA test, followed by a Tukey multiple comparisons test (significant P-value<0.05). Only significant P-values are shown: *P<0.05, P<0.01, *P<0.001, ****P<0.0001.
Figure 8D:
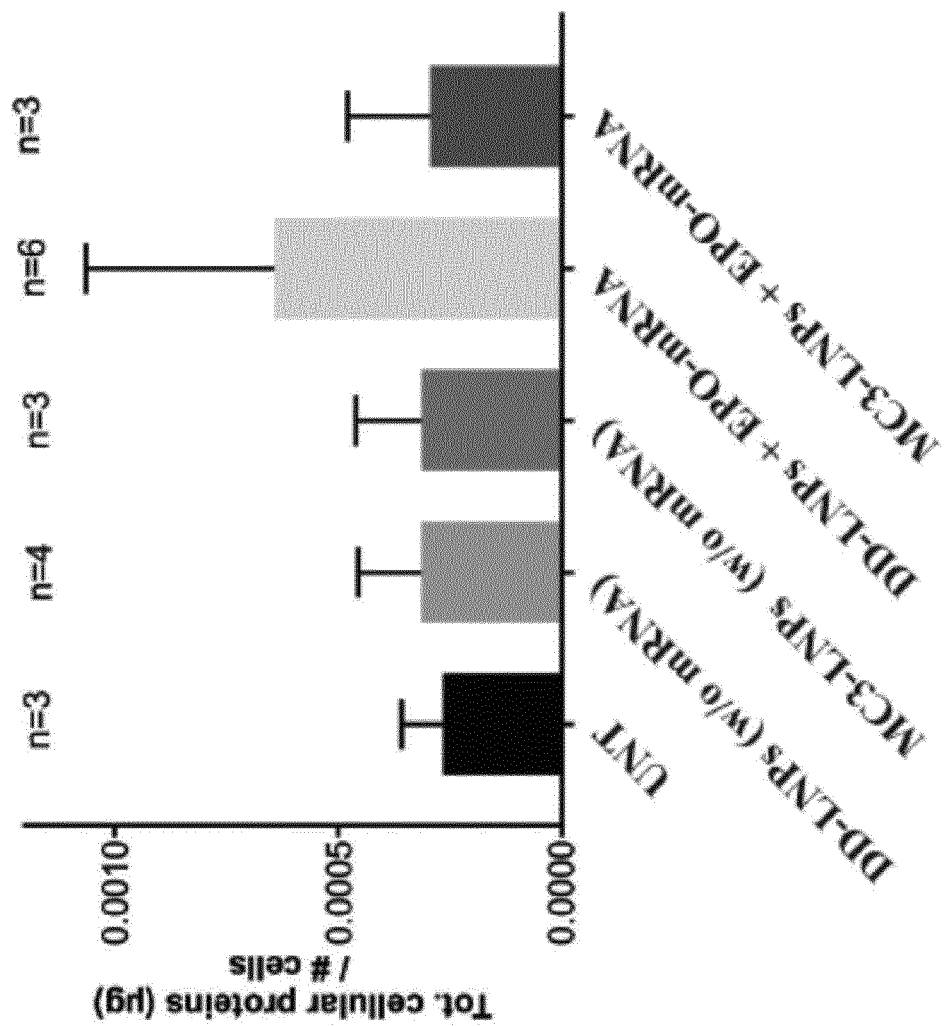
FIG. 8D and FIG. 8E show the effect of LNPs on total intracellular protein (FIG. 8D) and total secreted protein (FIG. 8E). After 96 hours of LNP treatment, total cellular protein (intracellular and secreted) was quantified and normalized to ΔN. The number (n) represents biological replicates assessed for each treatment. Significant difference between each group was assessed by using a one-way ANOVA test, followed by a Tukey multiple comparisons test (significant P-value<0.05). Only significant P-values are shown: *P<0.05, P<0.01, *P<0.001, ****P<0.0001.
Figure 8E:
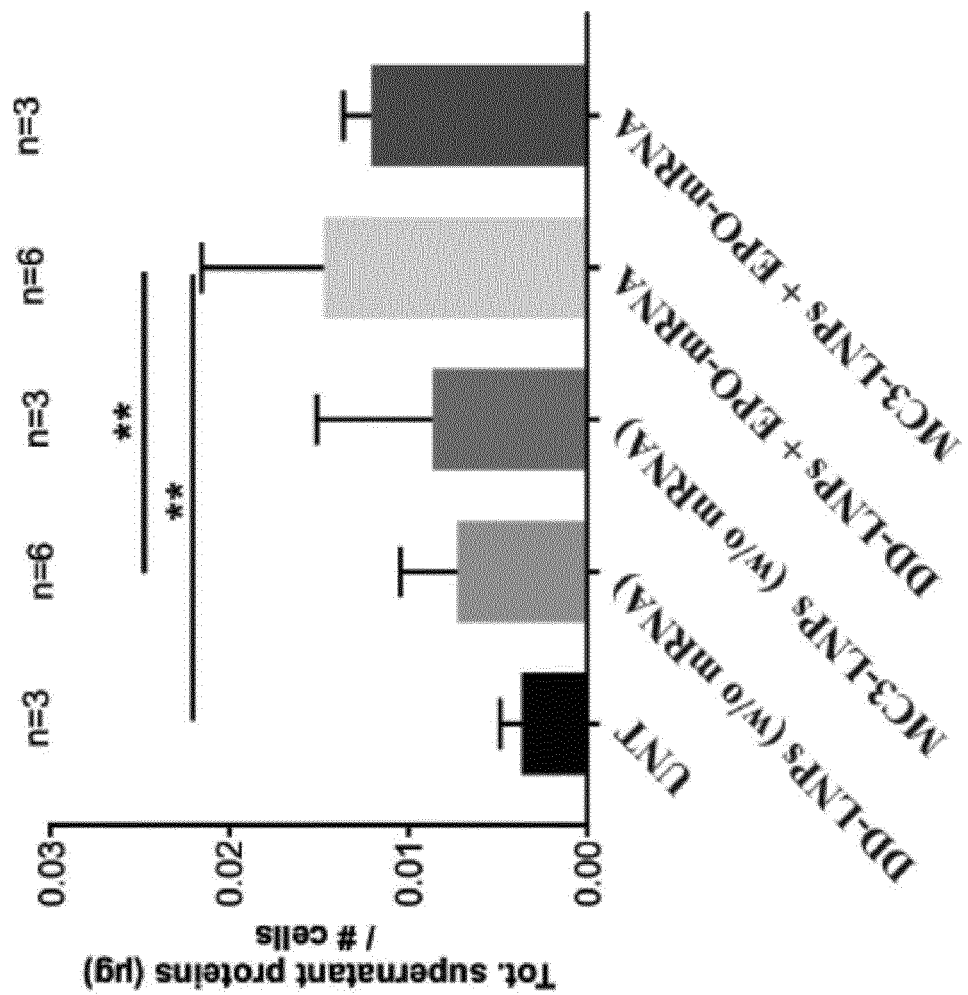

Nanoparticles have been shown to cause cell stress and to change cellular behavior (Panariti et al. (2012) Nanotechnol Sci Appl. 5:87-100; Halamoda Kenzaoui et al. (2012) Biochem J. 441(3):813-21; Petersen et al. (2011) Eur J The total RNA content was slightly increased in cells treated with LNPs without mRNA, but did not reach statistical significance (FIG. 8C). The total content of intracellular proteins remained unchanged after LNP treatment (FIG. 8D). However, the total content of secreted proteins in the extracellular environment increased significantly after treatment with DD-LNPs, particularly those with hEPO mRNA (FIG. 8E).

Figure 8F:
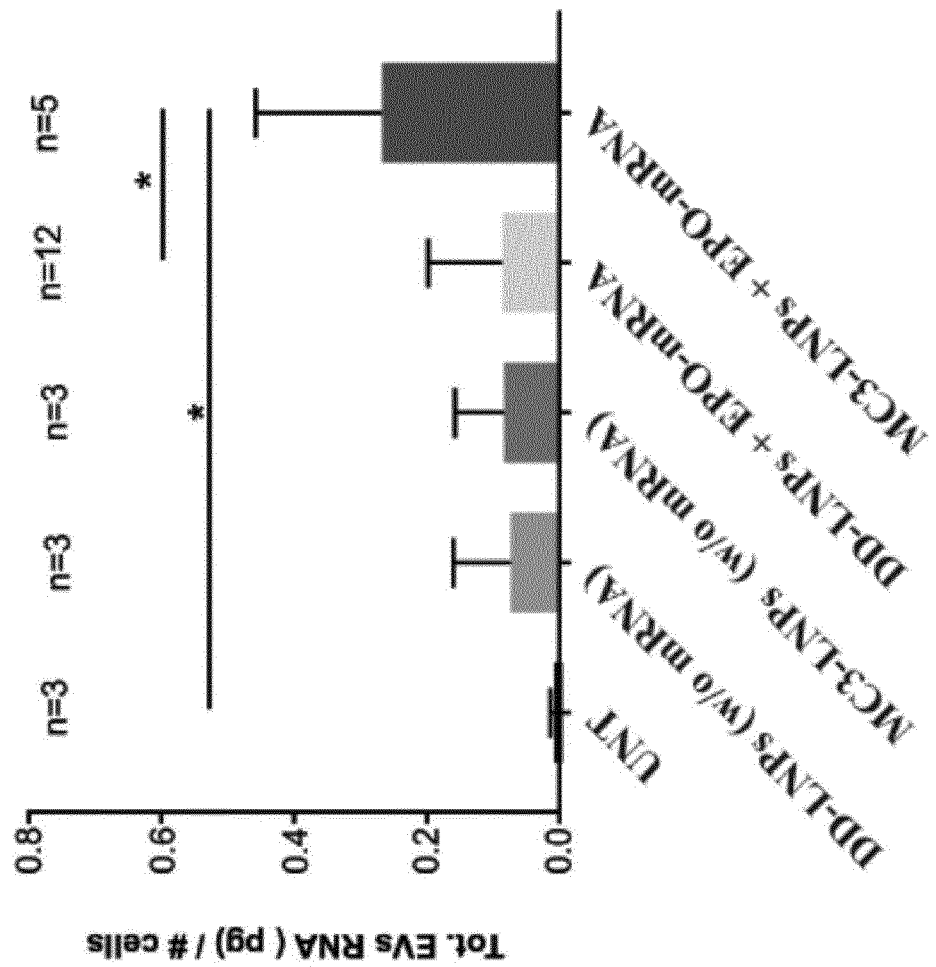
FIG. 8F shows the effect of LNPs on total RNA in EVs. After 96 hours of LNP treatment, total RNA in EVs was quantified and normalized to ΔN. The number (n) represents biological replicates assessed for each treatment. Significant difference between each group was assessed by using a one-way ANOVA test, followed by a Tukey multiple comparisons test (significant P-value<0.05). Only significant P-values are shown: *P<0.05, P<0.01, *P<0.001, ****P<0.0001.
Figure 8G:
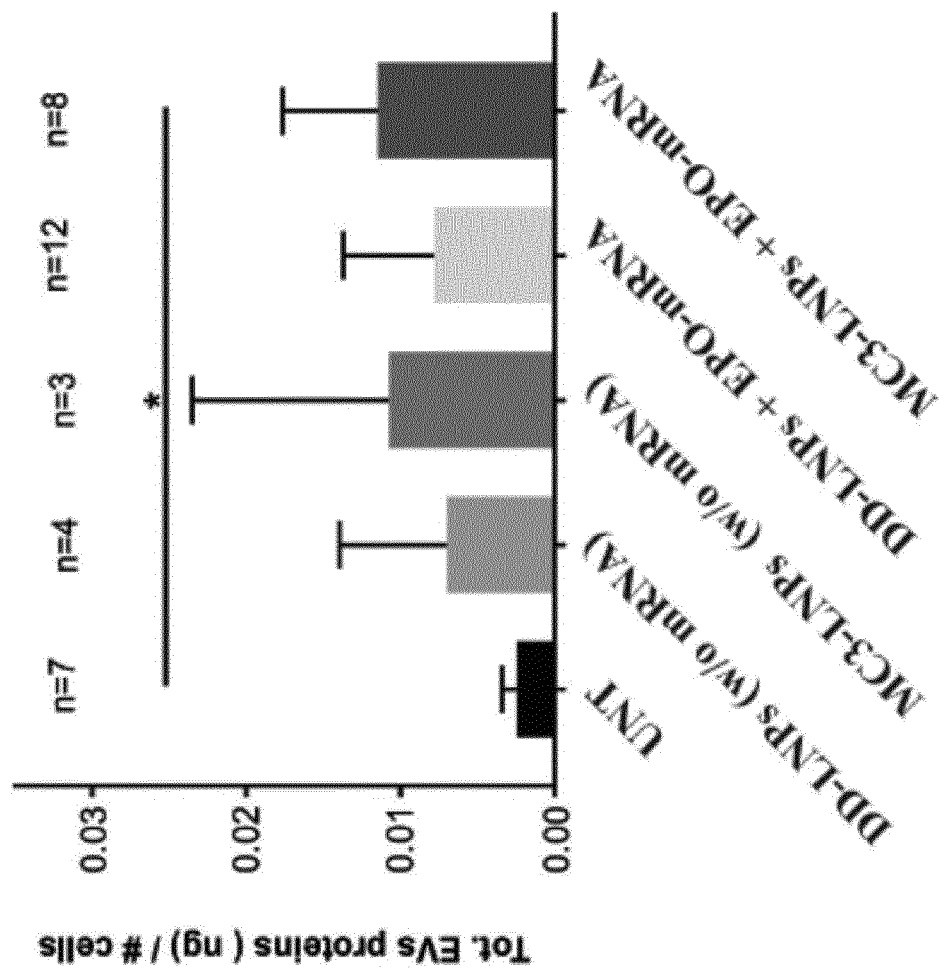
FIG. 8G shows the effect of LNPs on total protein in EVs. After 96 hours of LNP treatment, total proteins in EVs were quantified and normalized to ΔN. The number (n) represents biological replicates assessed for each treatment. Significant difference between each group was assessed by using a one-way ANOVA test, followed by a Tukey multiple comparisons test (significant P-value<0.05). Only significant P-values are shown: *P<0.05, P<0.01, *P<0.001, ****P<0.0001.

Quantification of total RNA and protein content of EVs: Assessment of the effect of hEPO mRNA containing LNPs on cell-derived extracellular vesicles (EVs) showed that the total RNA content of EVs from cells treated with mRNA-loaded MC3-LNPs was higher than the total RNA content of EVs from untreated cells or cells treated with mRNA-loaded DD-LNPs. The total RNA content of EVs increased after treatment with MC3-LNPs, particularly those with hEPO mRNA (FIG. 8F). This suggests that, following MC3-LNP treatment, cellular RNA may end up in EVs. Additionally, total EV protein content was increased after MC3-LNP treatment (FIG. 8G). Taken together, these results suggest that cells may secrete more proteins when they receive LNPs, and the secreted proteins may be detected in both cultured supernatants and in secreted EVs (FIG. 8E and FIG. 8G). Thus, administration of LNPs may cause cellular stress, resulting in alterations to cell growth and/or the amount of proteins secreted by cells.

Figure 16A:
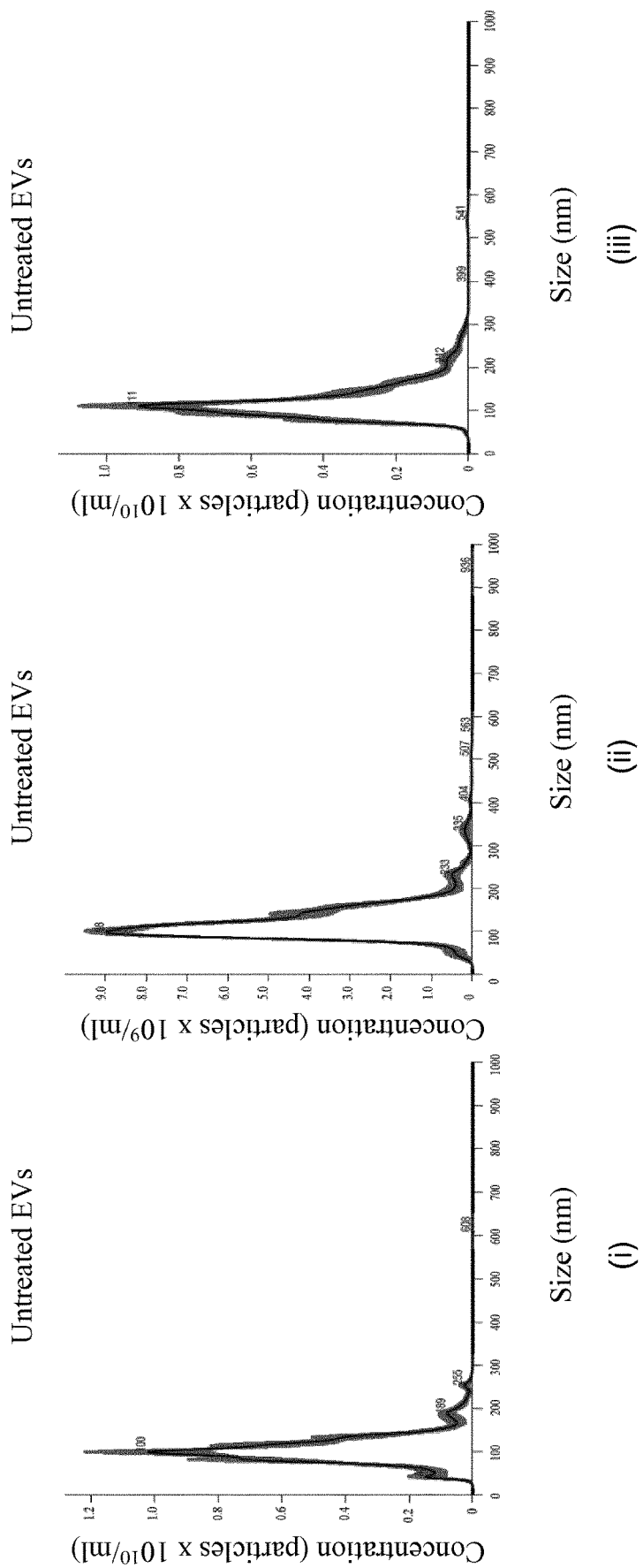
FIG. 16A and FIG. 16B show the results of a nanoparticle tracking analysis (NTA) of isolated EVs derived from untreated or MC3-LNP treated HTB-177 cells.
Figure 16B:
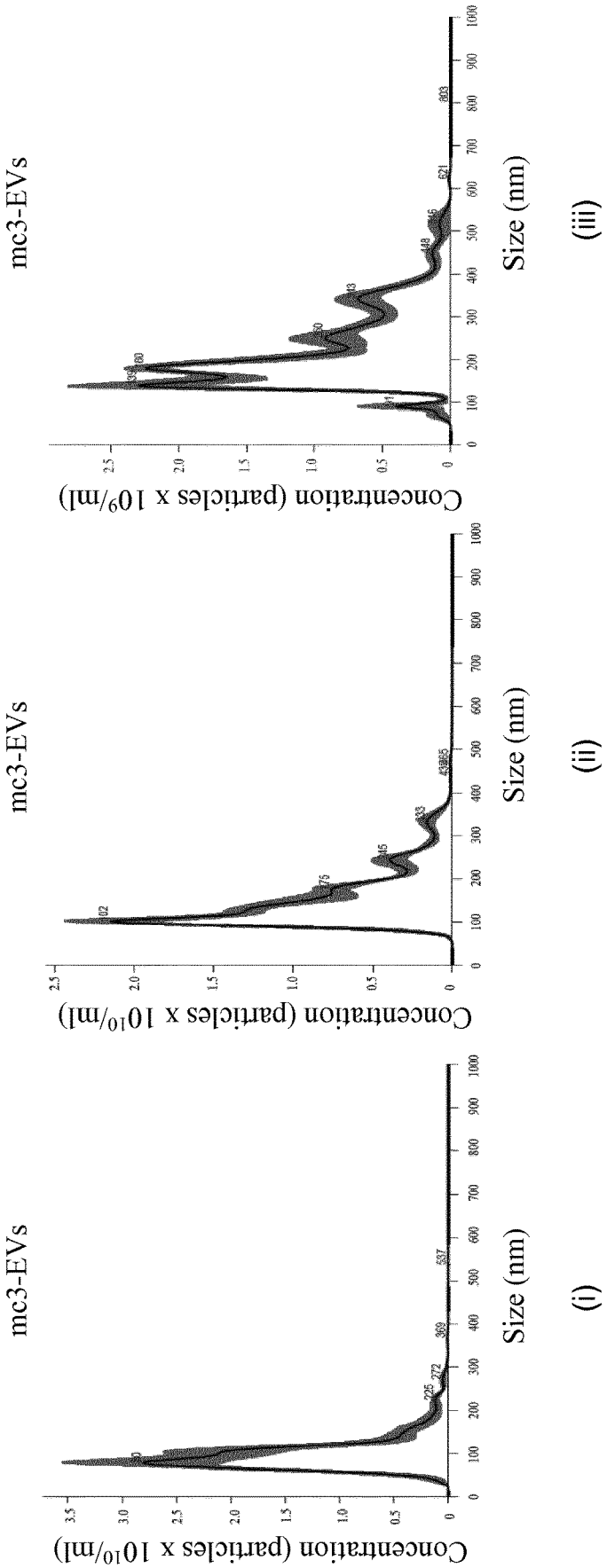

Size determination and concentration of EVs: EVs were characterized for size and concentration by nanoparticle tracking analysis (NTA). The mean±SEM EV mode size (measured from triplicate samples) was 100.2±3.7 nm from untreated cells, and 116.4±9.23 nm from MC3-LNP treated cells (FIG. 16A and FIG. 16B; see also Tables 3-8). The mean±SEM EV concentration (measured from triplicate samples) was $5.81 \times 10^{11} \pm 2.25 \times 10^{10}$ particles/mL from untreated cells, and $1.25 \times 10^{12} \pm 1.54 \times 10^{11}$ particles/mL from MC3-LNP treated cells.

TABLE 3

Untreated EVs (i).

| | |
|---|---|
| Mean | 107.2 +/− 2.4 nm |
| Mode | 93.5 +/− 3.4 nm |
| Standard deviation (SD) | 35.0 +/− 2.7 nm |
| D10 | 70.3 +/− 2.2 nm |
| D50 | 102.7 +/− 1.5 nm |
| D90 | 146.8 +/− 8.5 nm |
| Particles/mL | $5.77 \times 10^{11}$ +/− $2.39 \times 10^{10}$ |

TABLE 4

Untreated EVs (ii).

| | |
|---|---|
| Mean | 127.5 +/− 4.8 nm |
| Mode | 101.3 +/− 3.2 nm |
| Standard deviation (SD) | 53.7 +/− 5.4 nm |
| D10 | 84.1 +/− 2.3 nm |
| D50 | 114.0 +/− 1.9 nm |
| D90 | 180.8 +/− 13.1 nm |
| Particles/mL | $6.09 \times 10^{11}$ +/− $2.03\ 10^{10}$ |

TABLE 5

Untreated EVs (iii).

| | |
|---|---|
| Mean | 125.2 +/− 4.2 nm |
| Mode | 103.9 +/− 4.5 nm |
| Standard deviation (SD) | 44.2 +/− 5.6 nm |
| D10 | 83.5 +/− 2.6 nm |
| D50 | 114.7 +/− 2.6 nm |
| D90 | 179.6 +/− 11.7 nm |
| Particles/mL | $5.58 \times 10^{11}$ +/− $2.34 \times 10^{10}$ |

TABLE 6

MC3-EVS (i).

| | |
|---|---|
| Mean | 98.6 +/− 5.2 nm |
| Mode | 83.7 +/− 7.9 nm |
| Standard deviation (SD) | 41.0 +/− 3.0 nm |
| D10 | 62.1 +/− 3.5 nm |
| D50 | 88.7 +/− 5.0 nm |
| D90 | 145.9 +/− 10.0 nm |
| Particles/mL | $1.78 \times 10^{12}$ +/− $3.35 \times 10^{11}$ |

TABLE 7

MC3-EVs (ii).

| | |
|---|---|
| Mean | 160.0 +/− 5.3 nm |
| Mode | 109.7 +/− 10.2 nm |
| Standard deviation (SD) | 70.3 +/− 3.1 nm |
| D10 | 95.4 +/− 2.0 nm |
| D50 | 137.1 +/− 5.1 nm |
| D90 | 263.9 +/− 8.3 nm |
| Particles/mL | $1.70 \times 10^{12}$ +/− $1.12 \times 10^{11}$ |

TABLE 8

MC3-EVs (iii).

| | |
|---|---|
| Mean | 228.9 +/− 9.7 nm |
| Mode | 155.9 +/− 9.6 nm |
| Standard deviation (SD) | 89.4 +/− 7.8 nm |

TABLE 8-continued

MC3-EVs (iii).

| | |
|---|---|
| D10 | 139.9 +/− 4.0 nm |
| D50 | 204.1 +/− 9.0 nm |
| D90 | 364.5 +/− 26.0 nm |
| Particles/mL | $2.94 \times 10^{11}$ +/− $1.37 \times 10^{10}$ |

Example 3: Detection of LNP-Derived Ionizable Lipids and mRNA in EVs

Studies have shown that the majority of LNP-delivered RNA undergoes lysosomal degradation and/or the endocytosis recycling pathway, while only a minor amount escapes from endosomes; for instance, it has been estimated that the net egress of LNP-delivered siRNA may be less than 2% (Semple et al. (2010) Nat Biotechnol. 28(2):172-6; Sahay et al. (2013) Nat Biotechnol. 31(7):653-8; Sahay et al. (2010) J Control Release 145(3):82-95).

Consistent with these results, the experiments performed and described herein also show that, with the delivery of LNP-mRNA, less than 1% of administered mRNA can be detected in the cytosol of LNP-treated cells (FIG. 1D). mRNA delivered via LNPs with DLin-MC3-DMA formulations exhibit approximately two times more endosomal escape than mRNA delivered via LNPs with DLin-DMA formulations.

Figure 1D:
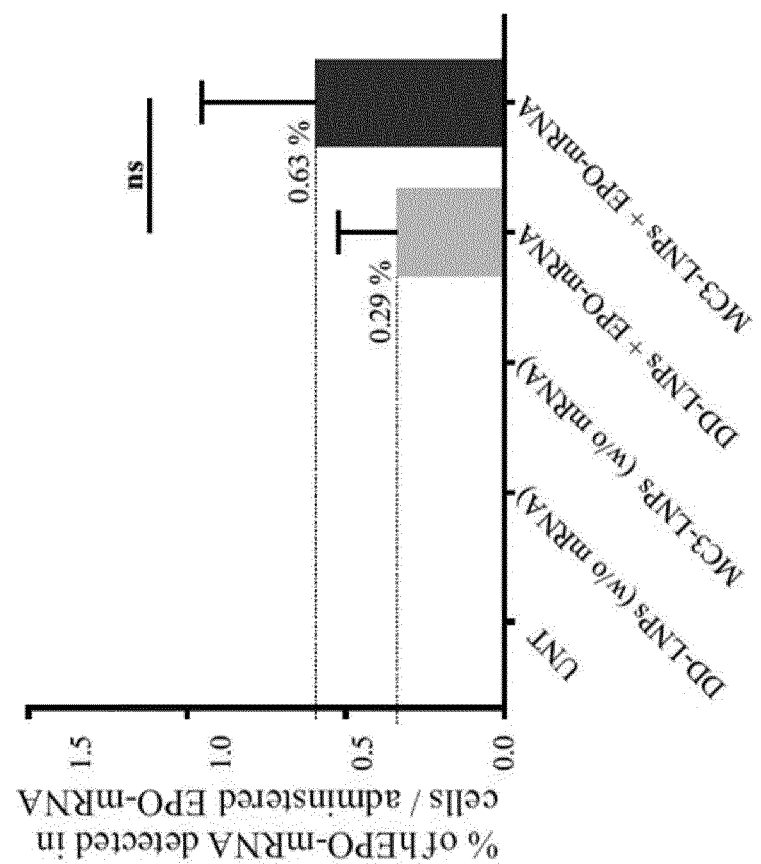
FIG. 1D shows the percentage of hEPO mRNA detected in the cytosol of LNP-treated cells relative to the total amount of hEPO mRNA administered via LNPs (100 µg).
Figure 1E:
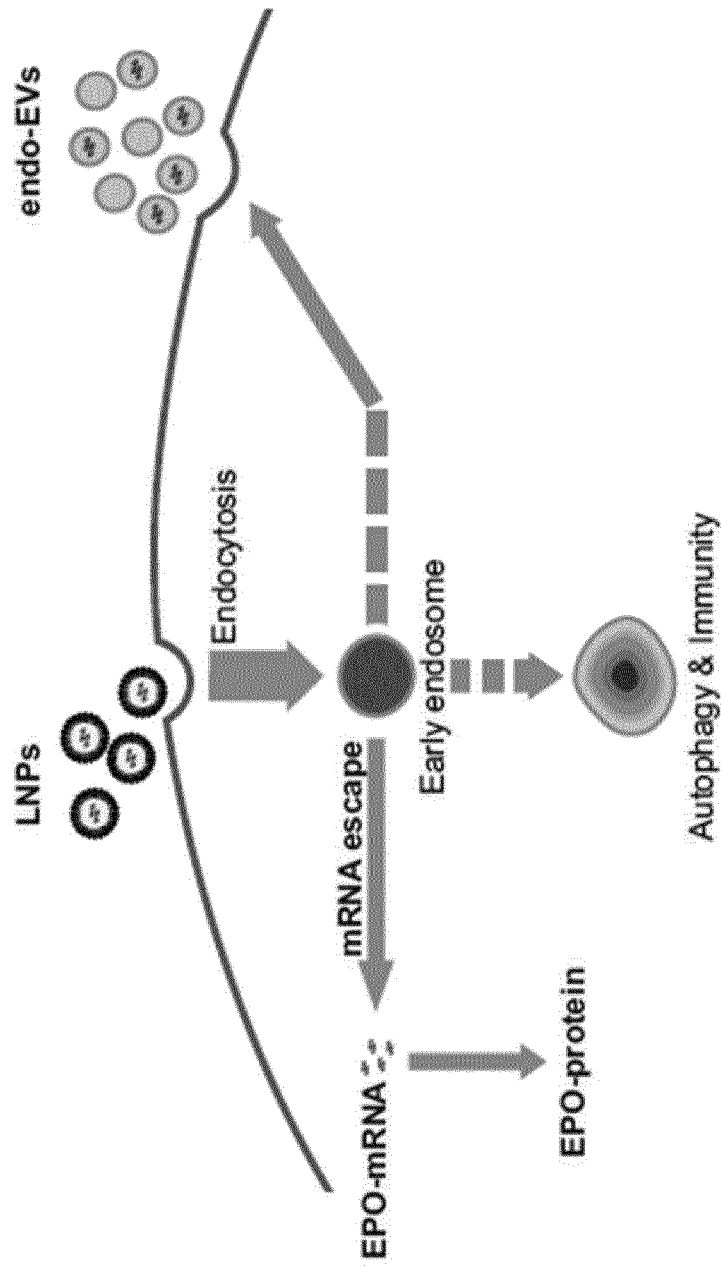
FIG. 1E shows an exemplary schematic of endosomal escape of hEPO mRNA into the cytosol after the endocytosis of LNPs, and the translation of hEPO mRNA into protein. Alternatively, hEPO mRNA may be packaged into endosome-derived EVs (endo-EVs) and secreted via exocytosis.
Figure 1F:
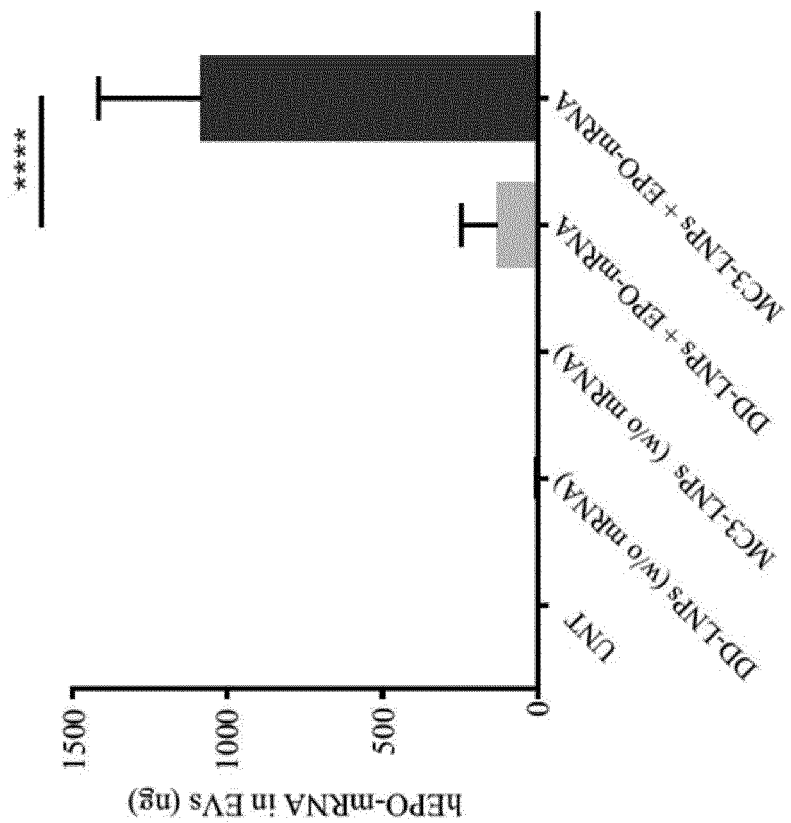
FIG. 1F shows the total amount of hEPO mRNA quantified in EVs isolated from LNP-treated cells. After detecting LNP-delivered hEPO mRNA in the cell cytosol, the remainder of the hEPO mRNA was evaluated in the EVs secreted from these cells. EVs were isolated and hEPO mRNA in EVs was quantified in by RT-qPCR (absolute quantification).

Without wishing to be bound by theory, it was hypothesized that there may be a link between endocytosis (uptake of LNPs) and exocytosis, in that some of the endocytosed LNP components might end up in secreted endosome-derived EVs ("exosomes" or "endo-EVs") (FIG. 1E). To investigate the fate of LNP-delivered mRNA and other components of LNPs when taken up by cells, hEPO mRNA in EVs was quantified by qPCR after a 96 hour period of LNP administration to cells (100 μg of hEPO mRNA). The results suggest that endo-EVs secreted from LNP-treated cells gained hEPO mRNA (FIG. 1F). The endo-EVs obtained from MC3-LNP-treated cells contained nearly 1000 times more hEPO mRNA than the endo-EVs obtained from DD-LNP-treated cells using the same dose of administered hEPO mRNA (FIG. 1F). Notably, hEPO mRNA quantification both in the cytoplasm of LNP-treated cells and in their secreted EVs indicated that mRNA with DLin-MC3-DMA formulations exhibited more endosomal escape than mRNA with DLin-DMA formulations. With DLin-MC3-DMA formulations, more mRNA was also detected in EVs (FIG. 1D and FIG. 1F).

Figure 1G:
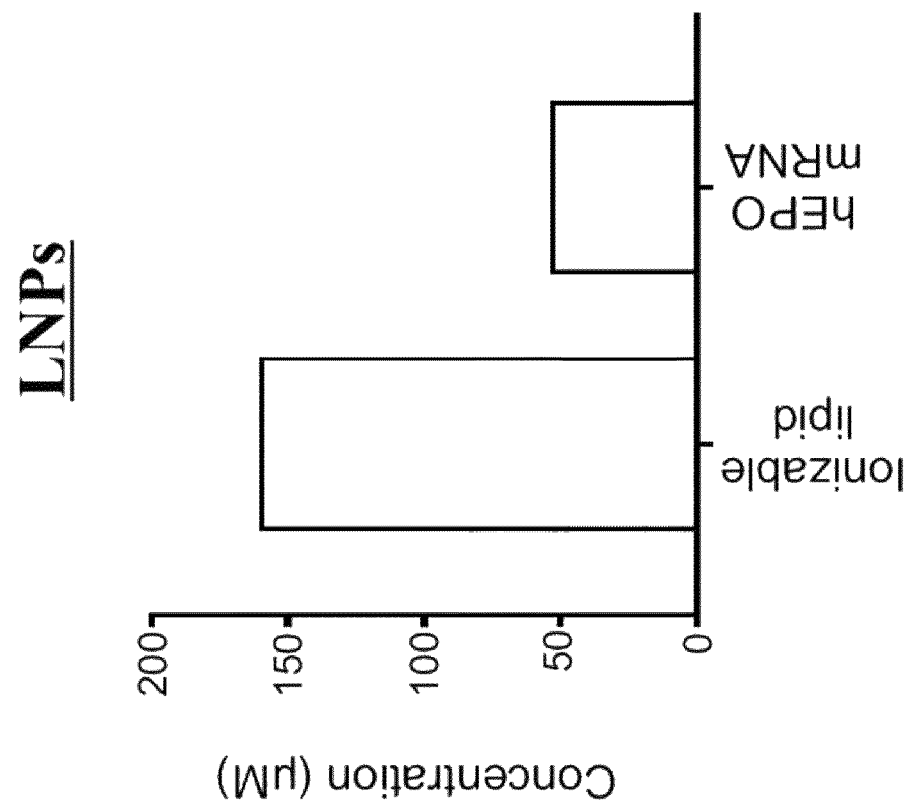
FIG. 1G shows molar concentrations of ionizable lipids and hEPO mRNA nucleotides (ionizable lipids per hEPO mRNA) in LNPs. The LNPs used for cellular delivery (MC3-LNPs and DD-LNPs) were analyzed for molar concentrations of ionizable lipids and hEPO mRNA nucleotides using gradient high-performance liquid chromatography (UPLC). In general, LNPs contained approximately 3 times more ionizable lipids (μmol) than hEPO mRNA nucleotides (μmol).
Figure 1H:
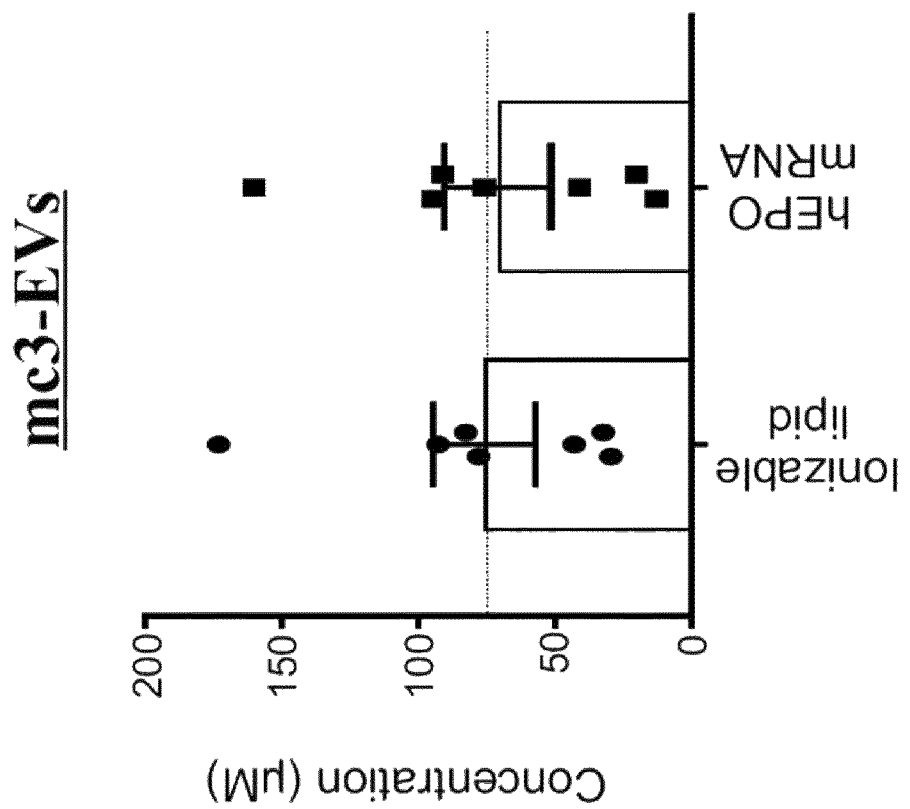
FIG. 1H and FIG. 1I show molar concentrations of ionizable lipids and hEPO mRNA nucleotides (ionizable lipids per hEPO mRNA) in EVs. EVs were isolated from LNP-treated cells, and the molar concentrations of ionizable lipids and hEPO mRNA nucleotides were analyzed in EVs using gradient high-performance liquid chromatography (UPLC). In general, MC3-EVs (FIG. 1H) and DD-EVs (FIG. 1I) contained approximately equal concentrations of ionizable lipids (μmol) and of hEPO mRNA nucleotides (μmol).
Figure 1I:
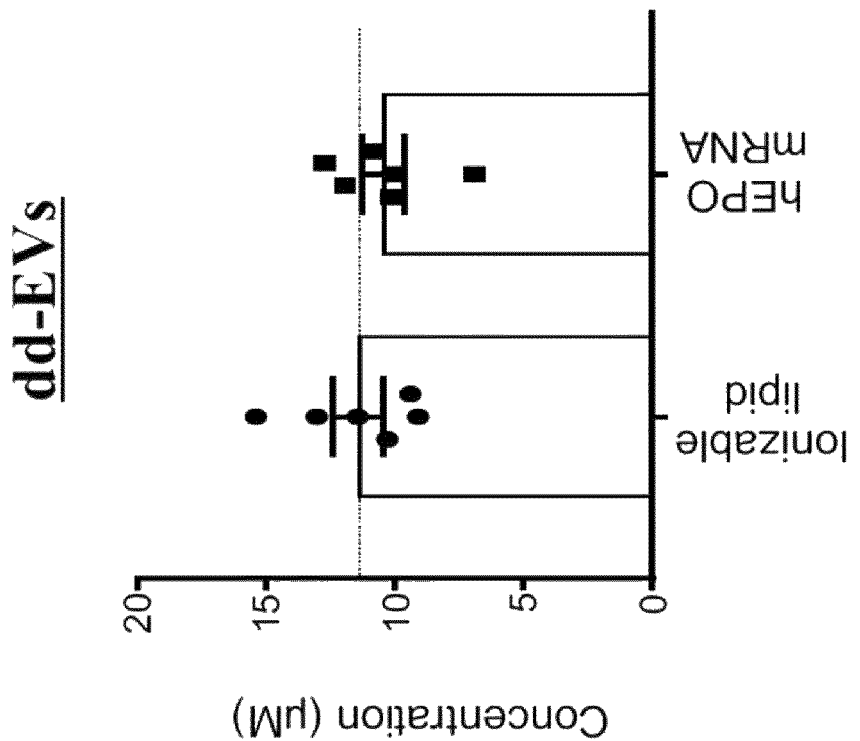
Figure 1J:
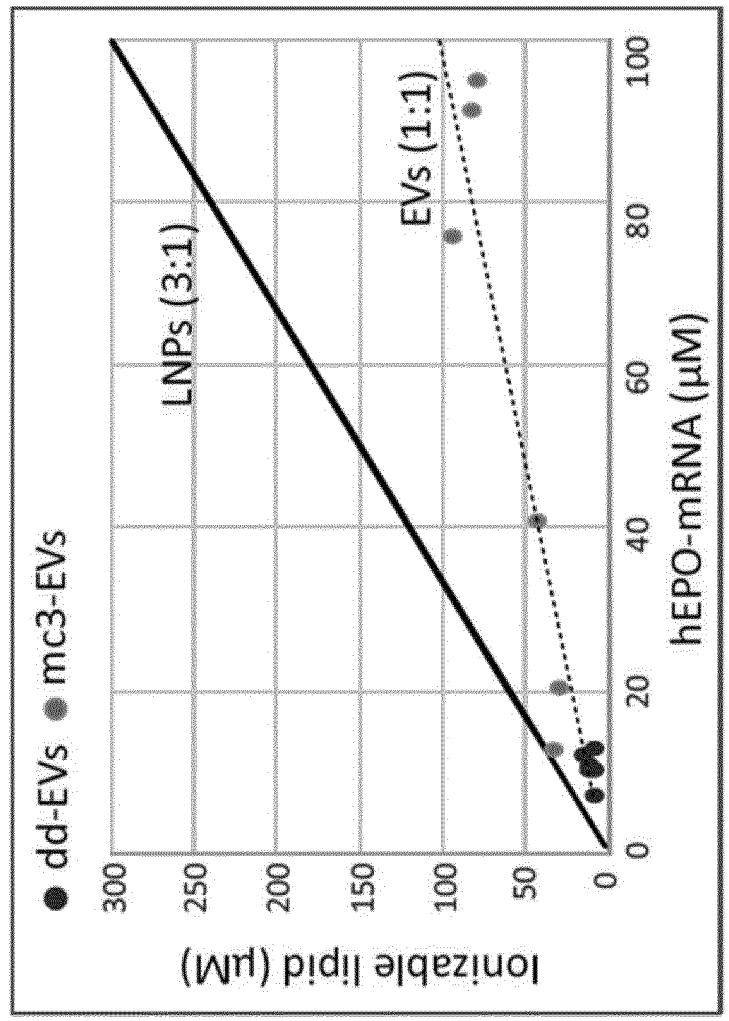
FIG. 1J shows a comparison between LNPs and EVs for molar ratios (mol/mol) of ionizable lipids per hEPO mRNA nucleotides. EVs generally contained a 1:1 molar ratio (1 mol of ionizable lipid per 1 mol of mRNA nucleotides), whereas LNPs generally contained a 3:1 molar ratio (3 mol of ionizable lipid per 1 mol of mRNA nucleotides).

Additionally, the presence of LNP ionizable lipids (DLin-MC3-DMA or DLin-DMA) was analyzed in EVs. The MC3-LNPs and DD-LNPs that were transferred to cells contained a 3:1 molar ratio (mol/mol) of ionizable lipid:hEPO mRNA nucleotides (FIG. 1G). EVs secreted from LNP-treated cells were also found to contain ionizable lipids. However, EVs contained fewer ionizable cationic lipids per hEPO mRNA molecule (FIG. 1H and FIG. 1I) as compared to LNPs. EVs contained a 1:1 molar ratio (mol/mol) of ionizable lipid:hEPO mRNA nucleotides (FIG. 1J).

Figure 18:
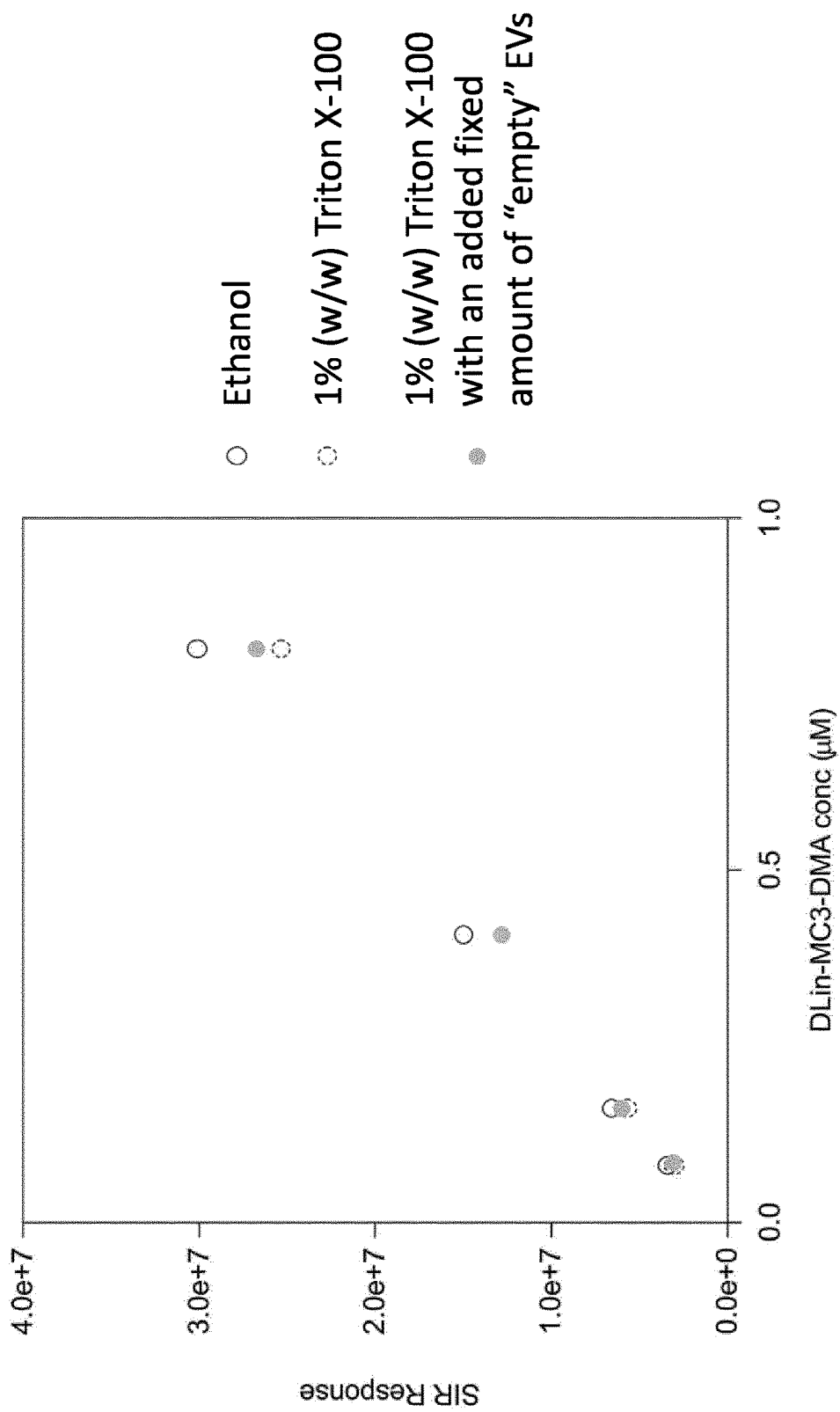
FIG. 18 shows the results of a UPLC-MS analysis of DLin-MC3-DMA samples prepared in ethanol, in 1% (w/w) Triton X-100, and in 1% (w/w) Triton X-100 with an added fixed amount of "empty" EVs.

For UPLC-MS analysis, DLin-MC3-DMA samples were dissolved in ethanol, in 1% (w/w) Triton X-100, or in 1% (w/w) Triton X-100 with an added fixed amount of "empty" EVs, and injected on a UPLC-MS system. The response for the Triton X-100 samples (with and without "empty" EVs)

was lower compared to the response for the samples dissolved in pure ethanol, but the error in quantification was estimated to be less than 10% (FIG. 18). Considering the variation in the sample preparations (for mRNA and lipid quantifications) and the qPCR (mRNA) and UPLC-MS (lipids) analyses, it remains likely that the mRNA and ionizable lipid are co-transported as a complex stochiometric salt (1:1) into the secreted EVs. Furthermore, a strong correlation was observed between the nucleotide concentration measured using qPCR and the lipid concentration determined using UPLC-MS for the different EV samples (FIG. 1J).

Since hEPO mRNA was detected in the cytoplasm and translated into hEPO protein after LNP delivery (FIG. 1A-C), and hEPO mRNA was detected in secreted EVs (FIG. 1F), experiments were performed to test whether the EVs may have gained hEPO protein from LNP-treated cells. Briefly, EVs isolated from LNP-treated cells were lysed and hEPO protein was analyzed by human erythropoietin ELISA. No hEPO protein was detected in EVs, suggesting that the hEPO protein produced may be derived from hEPO mRNA delivered via the EVs (data not shown).

Additionally, the possibility of interaction between LNPs and EVs outside of cells, as well as of direct transfer of LNP-mRNA into EVs, was evaluated. EVs were directly mixed (in the absence of cells) with LNPs containing hEPO mRNA. After a 2 hour incubation period, EVs were re-isolated and the presence of hEPO mRNA in EVs was assessed. Results showed that EVs were negative for hEPO mRNA when directly mixed with LNPs in the absence of cells (FIG. 9), suggesting that LNPs do not transfer hEPO mRNA directly to EVs outside of cells. Rather, EVs may gain mRNA via endocytosis of LNPs when cells are treated with LNPs.

Example 4: Delivery of hEPO mRNA to Epithelial and Immune Cells Via EVs

Figure 9:
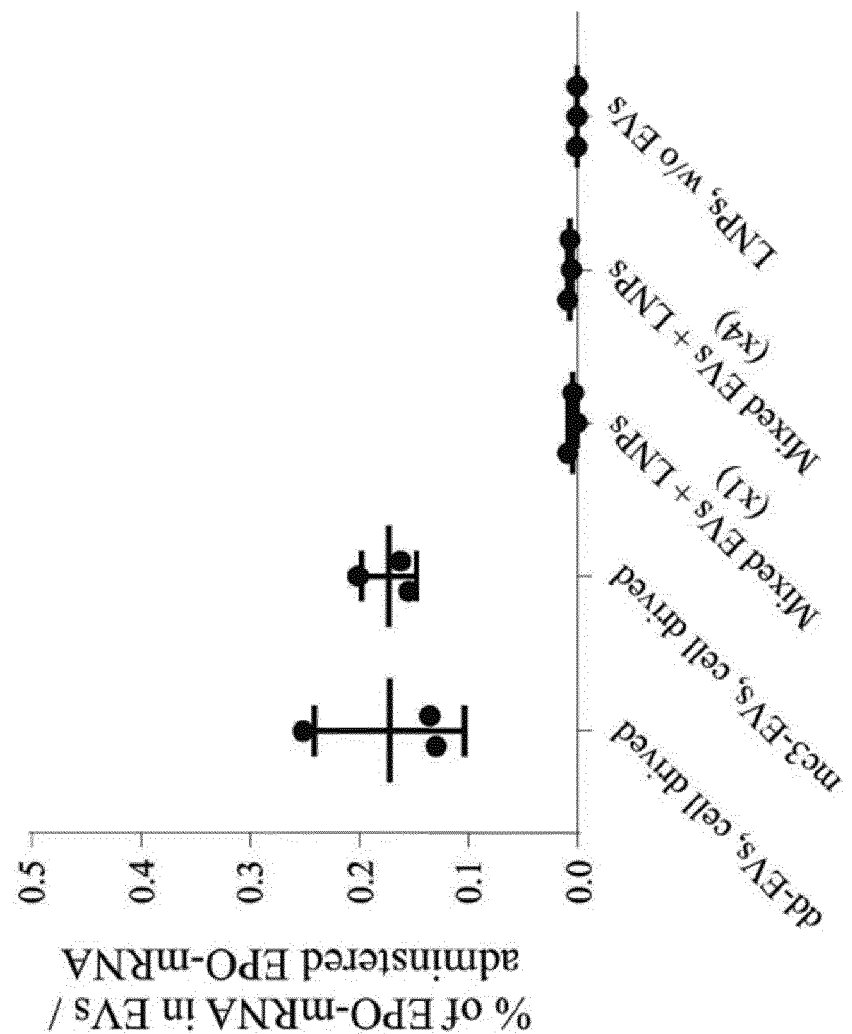
FIG. 9 shows an evaluation of direct transfer of hEPO mRNA from LNPs to EVs. MC3-LNPs and DD-LNPs containing hEPO mRNA were incubated with EVs (in the absence of cells) naïve of any prior treatment at 37° C. for 2 hours in 30 mL of PBS. Two different proportions of EVs and LNPs were incubated: 200 µg EVs+300 µL LNPs (1×), and 50 µg EVs+300 µL LNPs (4×). After 2 hours of incubation, EVs were re-isolated by ultracentrifugation. Total RNA from EVs was isolated and hEPO mRNA was quantified by qPCR to evaluate the direct transfer of hEPO mRNA from LNPs into EVs. As a positive control, equivalent volumes of DD-LNPs or MC3-LNPs were incubated in PBS in the absence of EVs and ultracentrifuged. Total RNA was isolated and hEPO mRNA was quantified by qPCR. In parallel experiments, the MC3-LNPs and DD-LNPs containing hEPO mRNA were transferred to cells and EVs were isolated from cells; total RNA from EVs was isolated and hEPO mRNA was quantified by qPCR to evaluate hEPO mRNA in EVs from LNP-treated cells. Abbreviations: dd-EVs or mc3-EVs, cell derived—EVs produced by cells treated with DD-LNPs or MC3-LNPs containing hEPO mRNA; mixed EVs+LNPs (×1)—EVs (200 µg) mixed with 300 µL of LNPs; mixed EVs+LNPs (×4)—EVs (50 µg) mixed with 300 µL of LNPs; LNPs, w/o EVs—only LNPs containing hEPO mRNA, not mixed with EVs. Experiments were performed in biological triplicate. Data are presented as percentage of hEPO mRNA detected in EVs after LNP treatment to cells or after incubation (direct mixing) of LNPs with EVs, relative to the starting amount of mRNA delivered by LNPs to cells or the mRNA amount directly mixed with EVs. Mean values with standard deviation (SD) of replicates are shown.

The experiments described above suggest that exogenous hEPO mRNA can be incorporated into endo-EVs after the endocytosis of LNPs (FIG. 1F and FIG. 9). Next, it was investigated whether (a) the EVs can then transport the exogenous hEPO mRNA to recipient cells by acting as delivery vehicles; and (b) the hEPO mRNA delivered to cells via EVs is functional, i.e., the mRNA can be translated to produce hEPO protein.

Figure 10A:
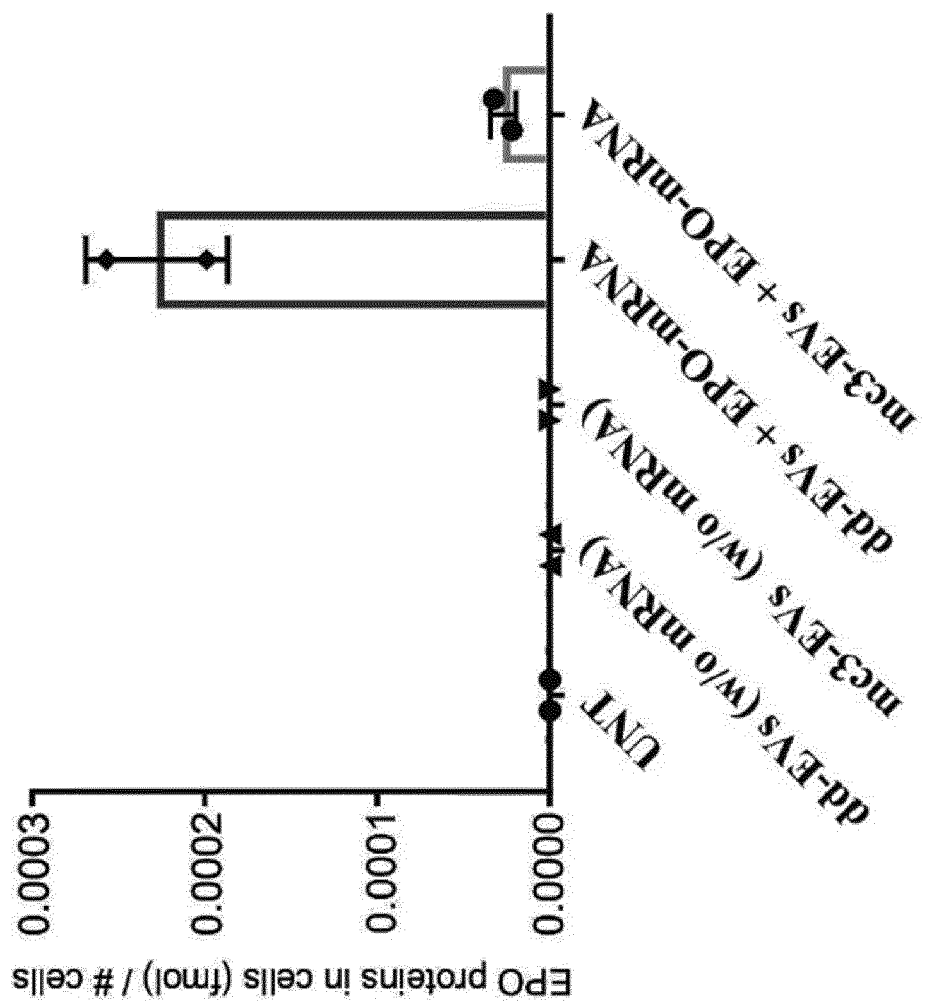
FIG. 10A shows delivery of hEPO mRNA to cells via EVs and detection of translated protein in the cytosol. MC3-EVs incorporated with hEPO mRNA (from MC3-LNP-treated cells), or DD-EVs incorporated with hEPO mRNA (from DD-LNP-treated cells) were transferred to HTB-177 recipient cells. EVs without hEPO mRNA (obtained from untreated cells), and LNPs without hEPO mRNA were delivered as controls. 96 hours after delivery hEPO mRNA, hEPO protein was quantified in cell lysates using ELISA specific for human erythropoietin. Quantity of hEPO protein in cell lysate was normalized to ΔN (defined as change in cell number, i.e., difference between the number of cells at the beginning and at the end of the LNP treatment interval). Data are presented from two (n=2) replicates at each time point. Each dot in the scattered plot represents each replicate.
Figure 10B:
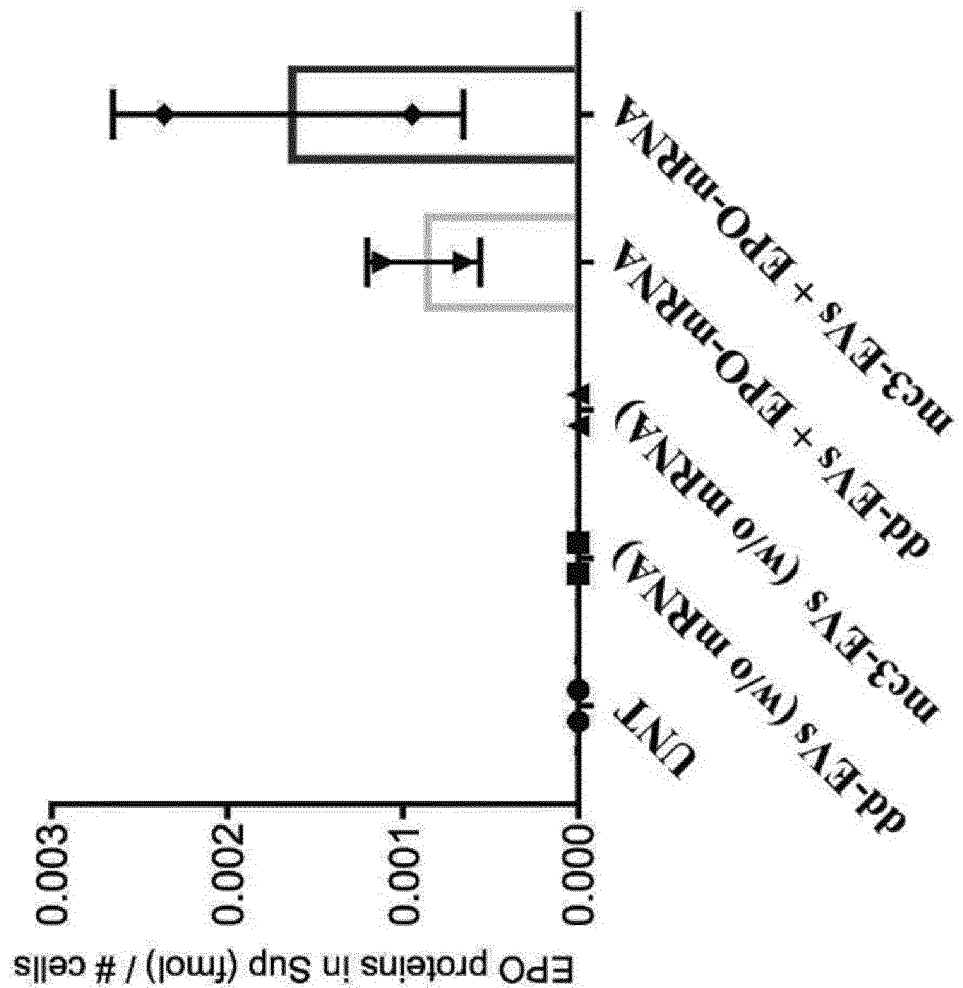
FIG. 10B shows delivery of hEPO mRNA to cells via EVs and detection of secreted protein. After 96 hours of hEPO mRNA delivery, the levels of secreted hEPO protein were quantified in the supernatants of cultured conditioned media using ELISA specific for human erythropoietin. Quantity of hEPO protein in supernatants was normalized to ΔN. Data are presented from two (n=2) replicates at each time point. Each dot in the scattered plot represents each replicate.
Figure 10C:
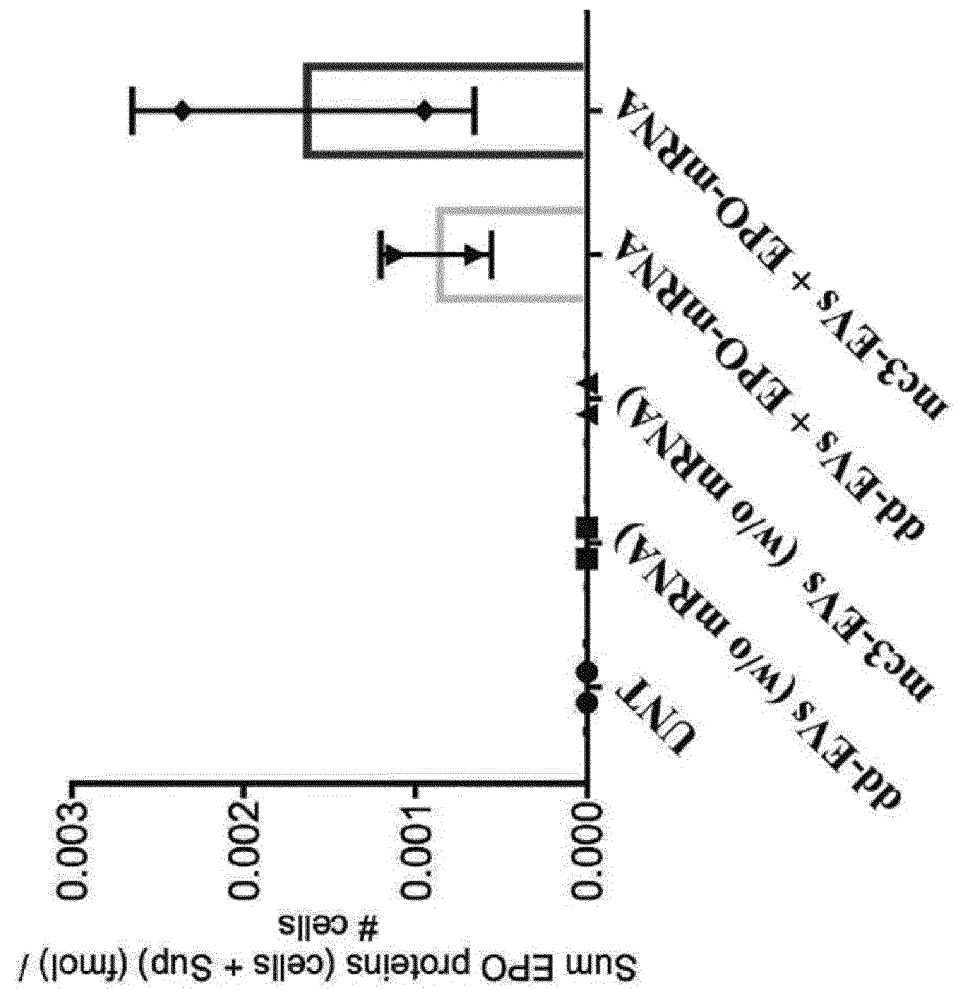
FIG. 10C shows the sum of hEPO protein quantified in cells and supernatants, normalized to ΔN. Data are presented from two (n=2) replicates at each time point. Each dot in the scattered plot represents each replicate.

MC3-EVs isolated from MC3-LNP-treated cells and DD-EVs isolated from DD-LNP-treated cells were transferred to recipient HTB-177 epithelial cells. After 96 hours of hEPO mRNA delivery, cells and their cultured supernatants were collected, and hEPO protein was evaluated by human erythropoietin ELISA. hEPO protein was detectable in cell lysates as well as in the cultured supernatants of recipient cells (i.e., cells which lack hEPO protein and do not express hEPO protein on their own) (FIG. 10A-C). Consistent with the cellular delivery of MC3-LNPs (FIG. 1B and FIG. 1C), MC3-EV-mediated hEPO mRNA delivery showed a higher level of hEPO protein production relative to DD-EV-mediated hEPO delivery (FIG. 10C).

Figure 10D:
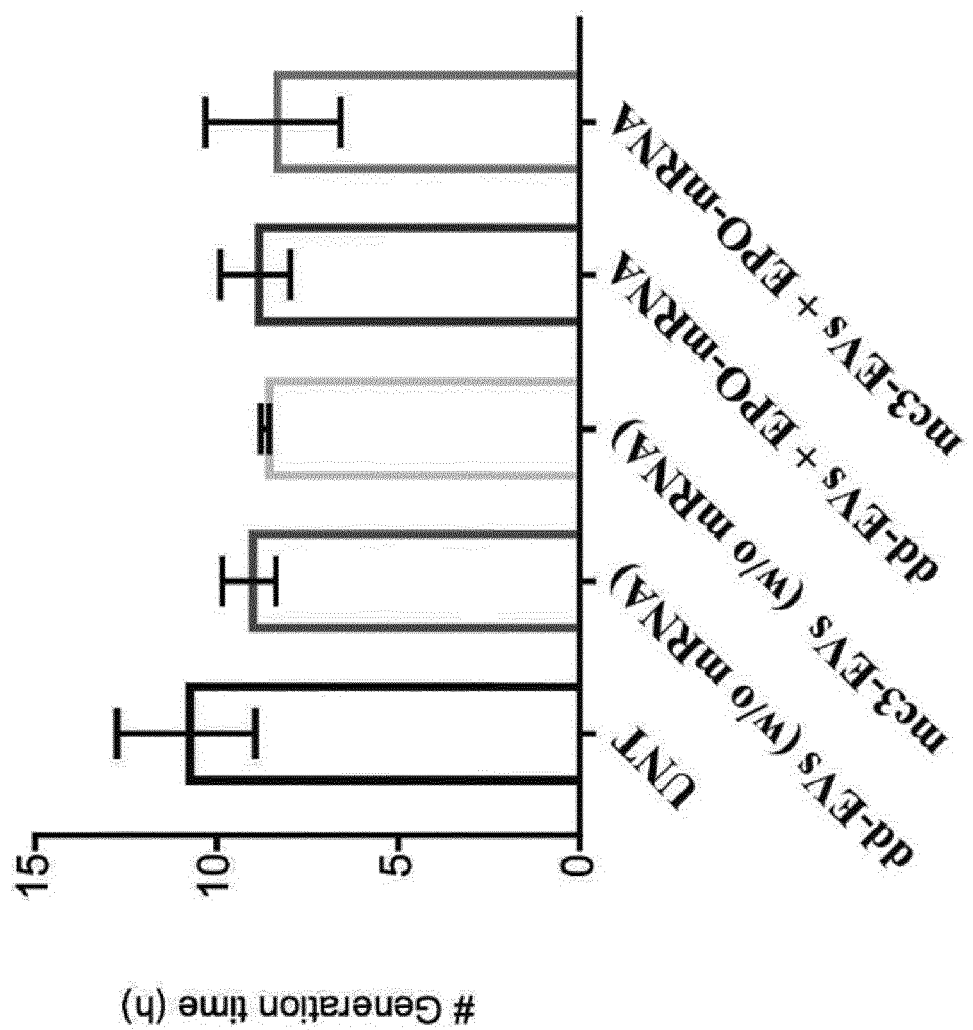
FIG. 10D shows the generation time of recipient cells after a culturing period of 96 hours with EV treatment. Data are presented from two (n=2) replicates at each time point. Each dot in the scattered plot represents each replicate.
Figure 10E:
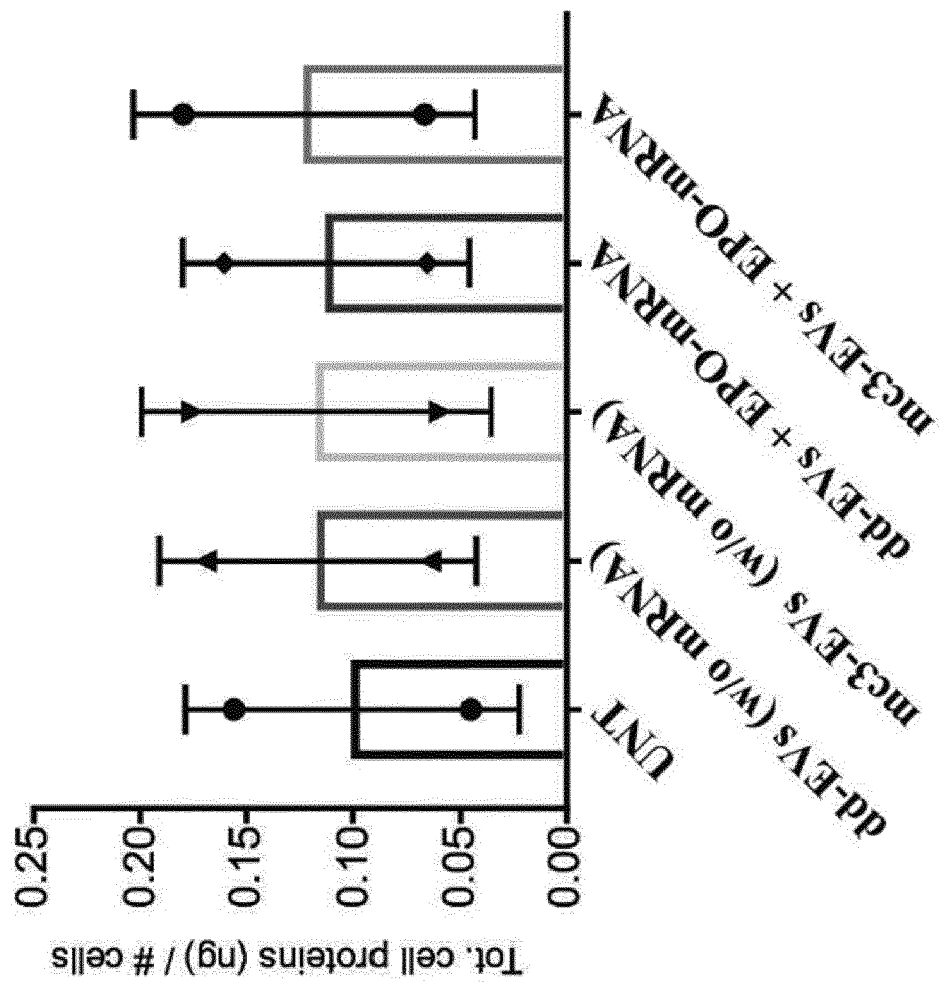
FIG. 10E shows total cellular proteins normalized to ΔN. Data are presented from two (n=2) replicates at each time point. Each dot in the scattered plot represents each replicate.
Figure 10F:
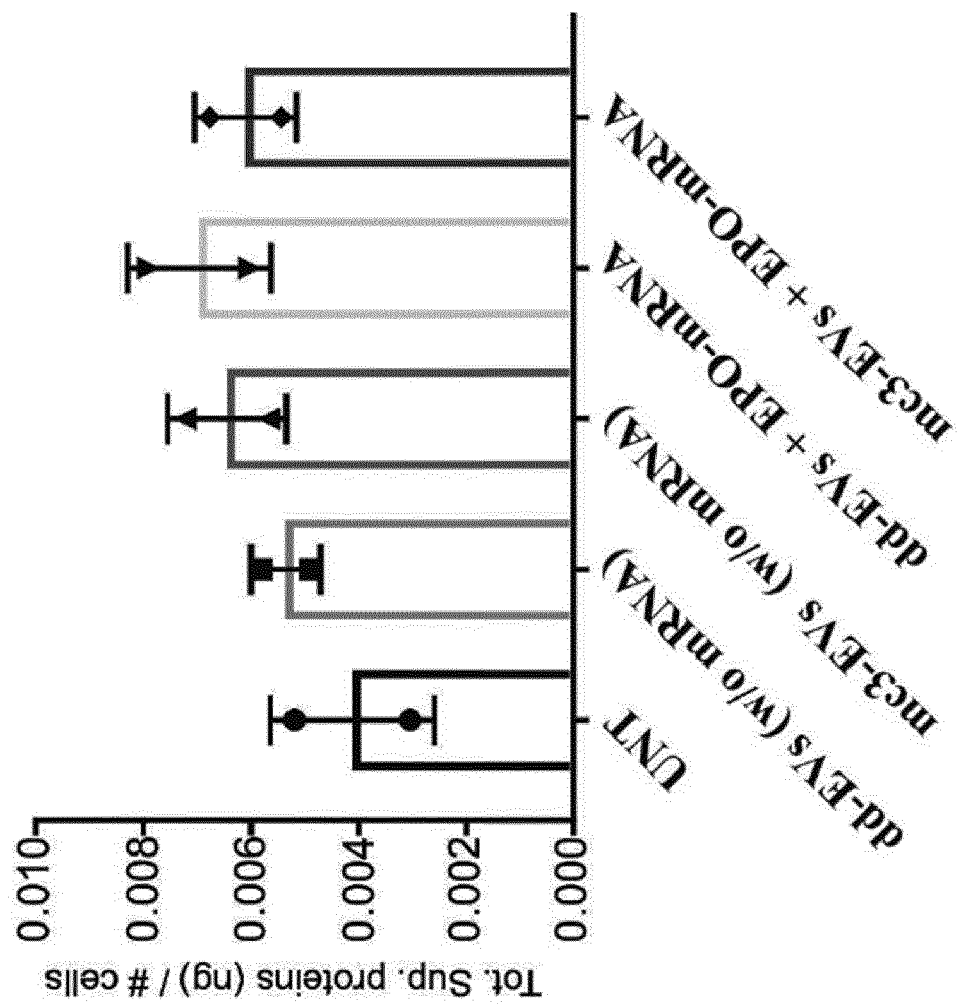
FIG. 10F shows total proteins in supernatants normalized to ΔN. Data are presented from two (n=2) replicates at each time point. Each dot in the scattered plot represents each replicate.
Figure 11:
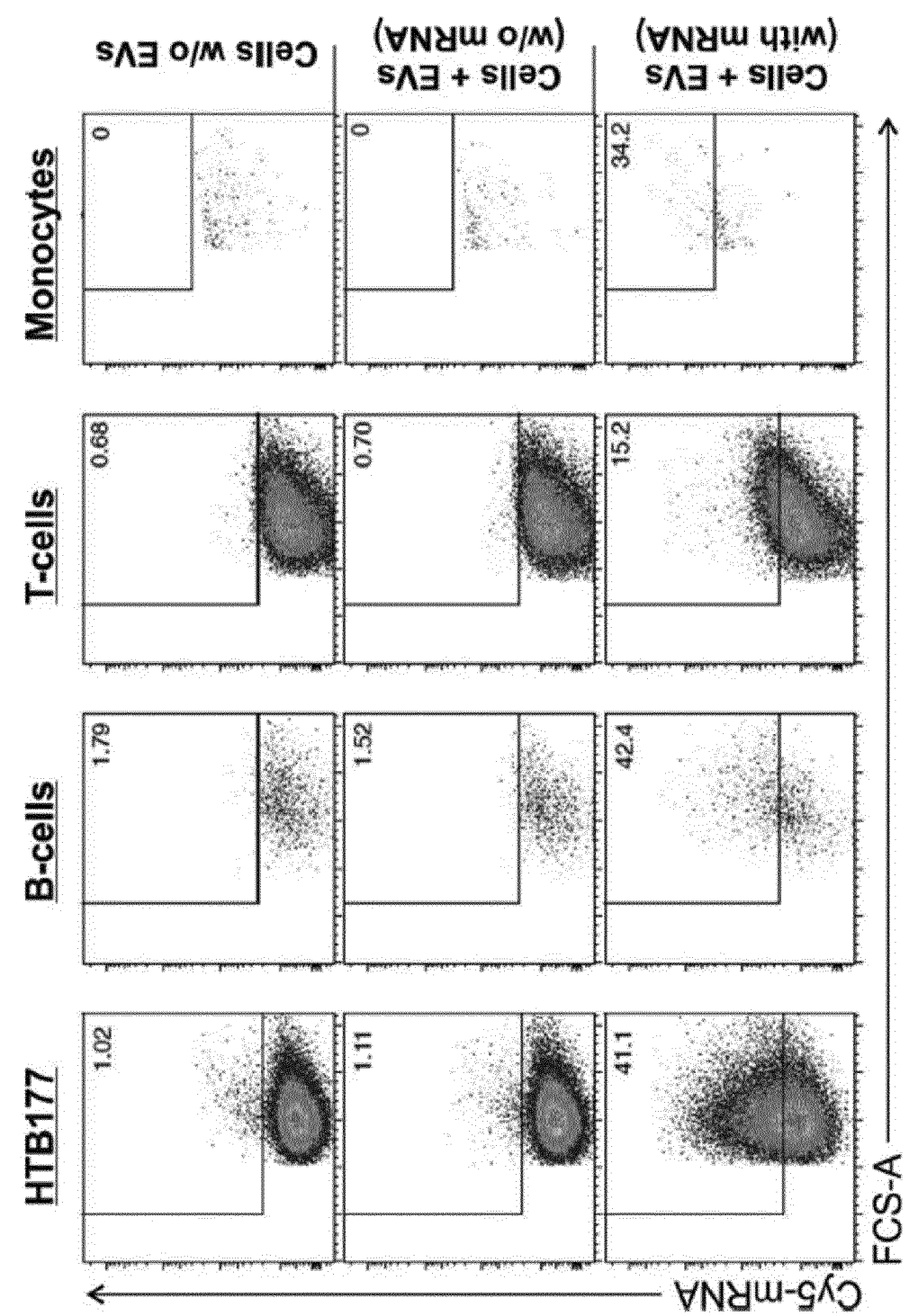
FIG. 11 shows FACS analysis of delivery of Cy5-EGFP-mRNA to epithelial cells and to primary immune cells via EVs. Epithelial cells (column 1): DD-LNPs containing 76 μg of Cy5-EGFP-mRNA were administered to human epithelial (HTB-177) cells and EVs from these cells (DD-EVs incorporated with mRNA) were isolated after 96 hours of LNP treatment. 78 μg of DD-EVs containing Cy5-EGFP-mRNA were transferred to HTB-177 cells (cultured $2 \times 10^5$ cells per well). Cells were harvested at different intervals (2 hours, 24 hours, 48 hours) after EV transfer and the presence of Cy5-EGFP-mRNA in cells was analyzed by FACS. Primary immune cells (columns 2-4): Peripheral blood mononuclear cells (PBMCs) isolated from healthy human buffy coats were cultured ($2 \times 10^5$ cells per well) and 78 μg of DD-EVs containing Cy5-EGFP-mRNA were transferred to PBMCs. Cells were harvested at different intervals (2 hours, 24 hours, 48 hours) after EV transfer, and stained with monoclonal antibodies (mAbs) for surface markers against CD19 (B cells), CD3 (T cells), and CD14 (monocytes). FACS analysis was performed to detect Cy5-EGFP-mRNA in recipient cells and the presence of Cy5-EGFP-mRNA in each cell type was estimated based on Cy5-fluorescence and antibody-fluorescence specific to each cell type. The FACS dot plots represent Cy5-EGFP-mRNA (y-axis) vs. FCS-A (x-axis) at each time point. Cells positive for Cy5-EGFP-mRNA are reported in the upper right quadrant. Abbreviations: cells w/o EVs—untreated cells; cells+EVs (w/o mRNA)—cells treated with EVs not containing mRNA; cells+EVs (with mRNA)—cells treated with EVs containing mRNA.

LNP-based delivery resulted in certain unfavorable effects on cellular behaviors (FIG. 8C-E). In contrast, EV-based delivery did not affect cell generation time or cell protein content, using either EVs with hEPO mRNA or EVs lacking hEPO mRNA (FIG. 10D-F). This suggests that cells which were stressed against LNP-based delivery may be more tolerant against EV-based delivery.

Next, it was examined whether EVs could deliver exogenous mRNA (i.e., hEPO mRNA) to immune cells, cells which are generally difficult to transfect using other delivery vehicles. Peripheral blood mononuclear cells (PBMCs) were isolated from buffy coats of healthy human and were seeded. After overnight incubation in the presence of appropriate immune cell stimuli, DD-EVs (derived from DD-LNP-treated cells) containing Cy5-EGFP-mRNA were delivered to recipient cells in single doses for 5 hours, 24 hours, and 48 hours, separately.

Figure 2A:
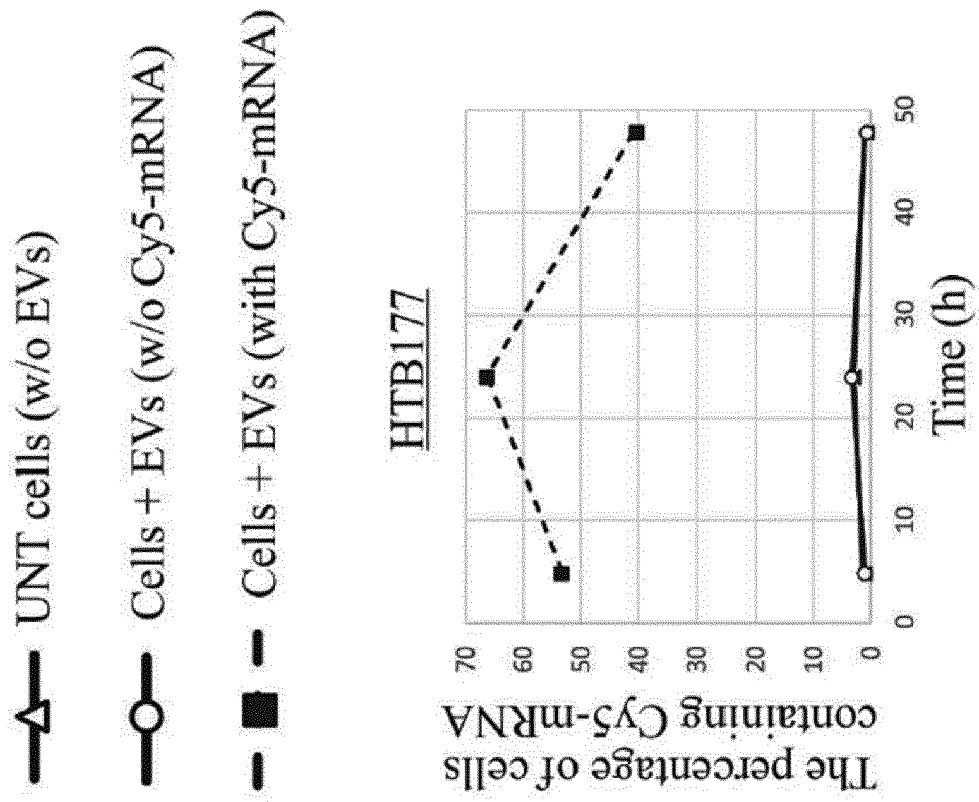
FIG. 2A shows delivery of Cy5-EGFP-mRNA to human epithelial (HTB-177) cells via EVs. DD-LNPs containing 76 μg of fluorescent Cyanine 5 (Cy5) EGFP-mRNA were administered to HTB-177 cells. After 96 hours of LNP treatment, EVs from DD-LNP treated cells (DD-EVs) were isolated. 78 μg of DD-EVs containing Cy5-EGFP-mRNA were transferred to autologous HTB-177 cells. After 5 hours, 24 hours, and 48 hours of EV delivery, Cy5-EGFP-mRNA delivery was assessed by FACS based on fluorescence in cells. Data are presented as percentage of HTB-177 cells containing EGFP-mRNA after EV transfer at each time point. Data are presented as mean values with standard deviation (SD) of at least three biological replicates. MC3-LNPs and DD-LNPs groups were compared using a parametric unpaired two-tailed t test. P values: P<0.01, **P<0.0001, and ns=not significant. Abbreviations: UNT (w/o EVs)—untreated cells; cells+EVs (w/o Cy5-mRNA)—DD-LNPs or MC3-LNPs transferred without mRNA; cells+EVs (with Cy5-mRNA)—DD-LNPs or MC3-LNPs transferred with mRNA.
Figure 2B:
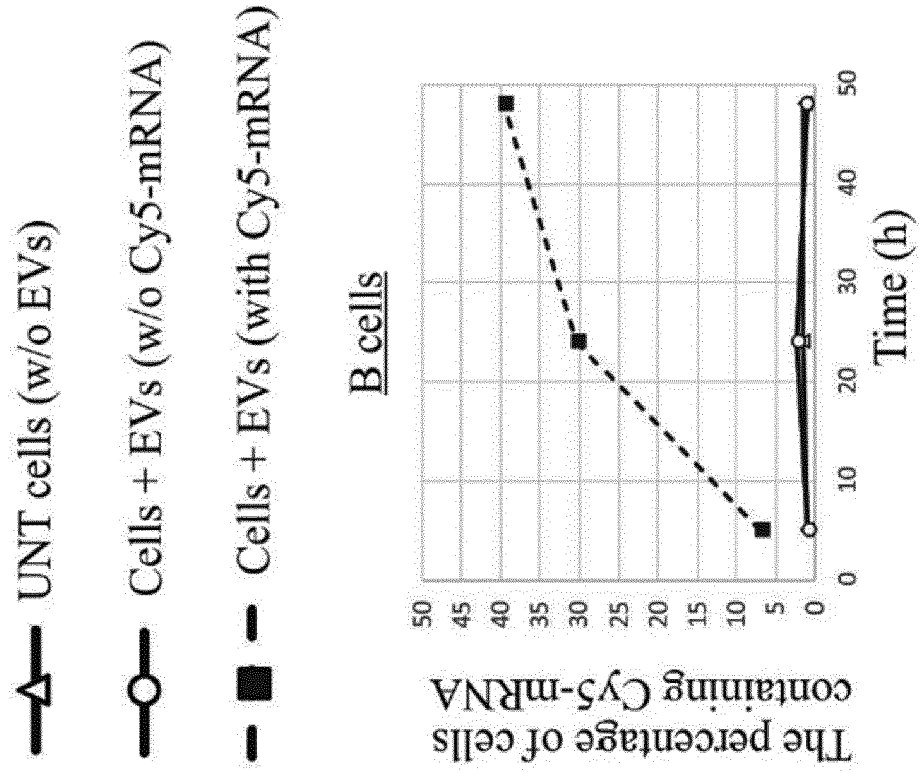
FIG. 2B, FIG. 2C, and FIG. 2D show delivery of Cy5-EGFP-mRNA to human peripheral blood mononuclear cells (PBMCs) via EVs. Peripheral blood mononuclear cells (PBMCs) were isolated from healthy human buffy coats and stained with specific surface markers against CD19 (B cells), CD3 (T cells), and CD14 (monocytes). 78 μg of DD-EVs containing Cy5-EGFP-mRNA were transferred to recipient cells. After 5 hours, 24 hours, and 48 hours of EV delivery, FACS analysis was performed to detect Cy5-EGFP-mRNA in recipient immune cells. The delivery of Cy5-EGFP-mRNA was estimated based on Cy5-fluorescence and antibody-fluorescence in B cells (FIG. 2B), T cells (FIG. 2C), and monocytes (FIG. 2D). Data are presented as percentage of cells containing Cy5-EGFP-mRNA after EV transfer at each time point. Data are presented as mean values with standard deviation (SD) of at least three biological replicates. MC3-LNPs and DD-LNPs groups were compared using a parametric unpaired two-tailed t test. P values: P<0.01, **P<0.0001, and ns=not significant. Abbreviations: UNT (w/o EVs)—untreated cells; cells+EVs (w/o Cy5-mRNA)—DD-LNPs or MC3-LNPs transferred without mRNA; cells+EVs (with Cy5-mRNA)—DD-LNPs or MC3-LNPs transferred with mRNA.
Figure 2C:
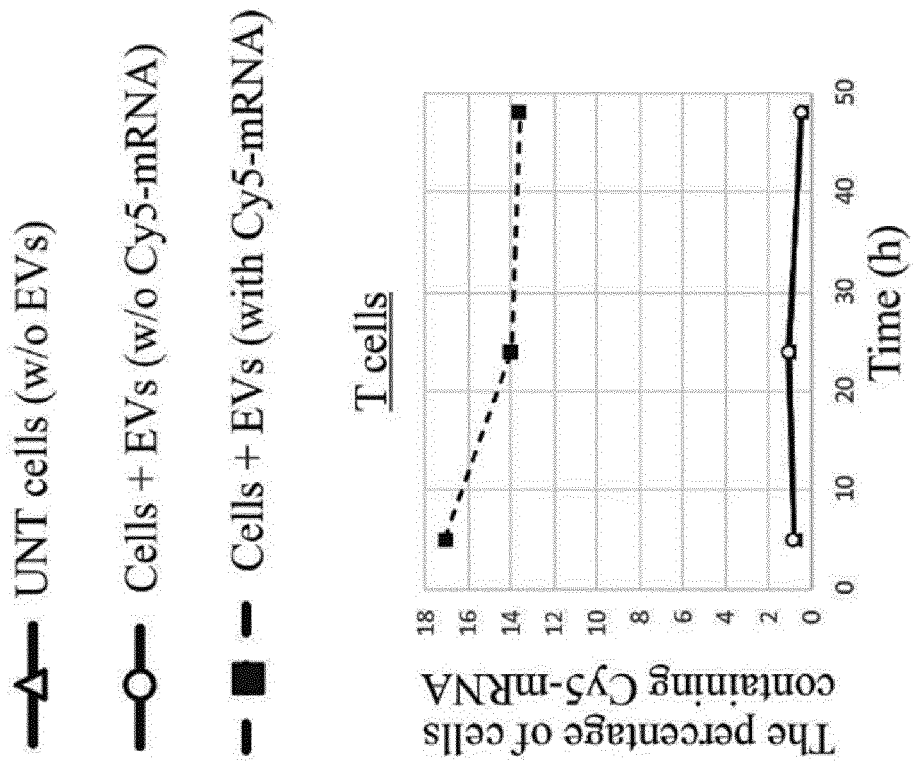
Figure 2D:
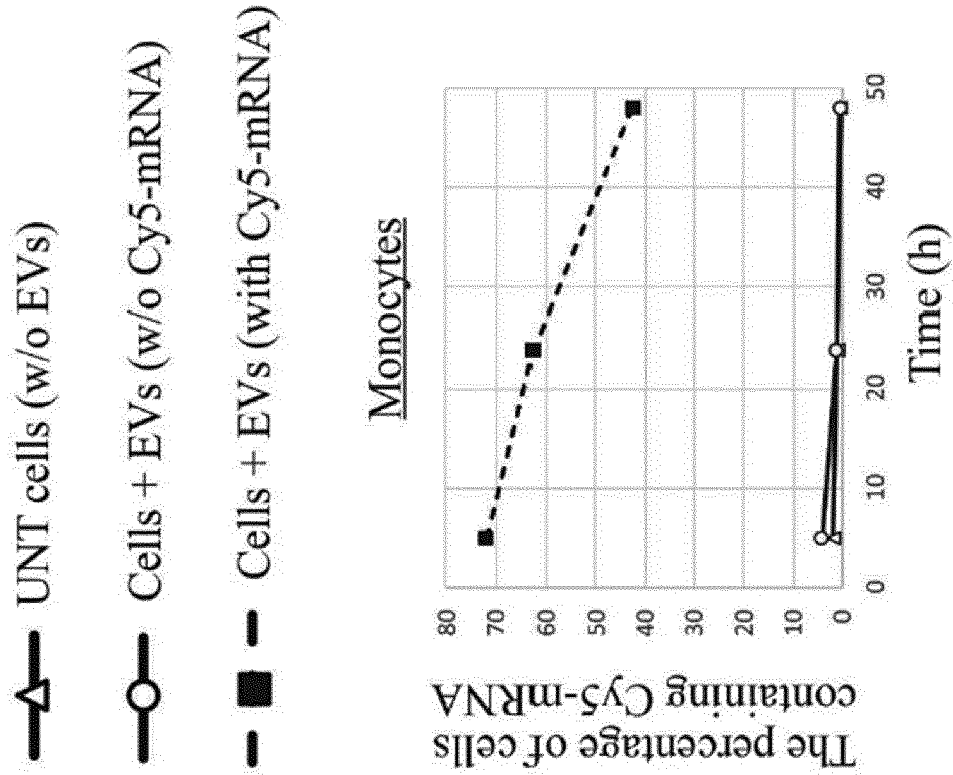

Cells were harvested after different intervals (5 hours, 24 hours, and 48 hours) of Cy5-EGFP-mRNA transfer via EVs, and stained with monoclonal antibodies (mAbs) for surface markers against CD19 (B cells), CD3 (T cells) and CD14 (monocytes) (Becton-Dickinson Biosciences). FACS analysis was performed to detect Cy5-EGFP-mRNA in recipient cells and the percentage of each cell type containing Cy5-EGFP-mRNA was estimated based on antibody-fluorescence and Cy5-fluorescence. Cy5-EGFP-mRNA was detectable in recipient immune cells after 5 hours of EV-mediated mRNA delivery, indicating that EVs can deliver mRNA to immune cells (FIG. 2B-D and FIG. 11). Nearly 70% of HTB-177 cells presented the uptake of Cy5-EGFP-mRNA after 24 hours of EVs delivery (FIG. 2A). 6%, 30%, and 40% of B-cells contained Cy5-EGFP-mRNA after 5 hours, 24 hours, and 48 hours of EVs delivery, respectively (FIG. 2B). 17% of T cells and 71% of monocytes contained Cy5-EGFP-mRNA 5 hours of EVs delivery (FIG. 2C and FIG. 2D).

Example 5: Delivery of Human EPO mRNA to Mice Via EVs

Figure 12:
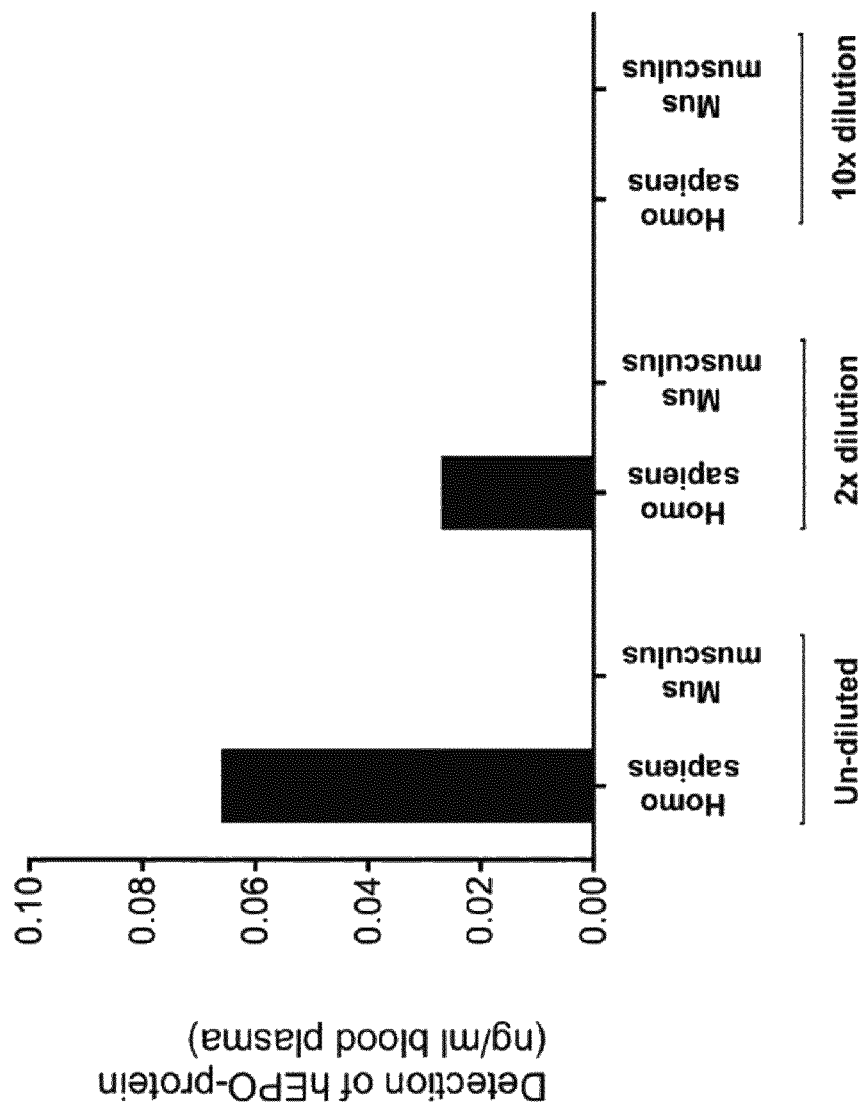
FIG. 12 shows testing of a human erythropoietin ELISA Kit (STEMCELL Technologies) to confirm specificity for human erythropoietin (hEPO) and to examine its cross-reactivity with mouse plasma EPO protein. Plasma from untreated mouse and fresh plasma from normal human, both undiluted and diluted (2×—two times; 10×—ten times), was tested. No signals were detected for hEPO in mouse plasma.

After determining that endo-EVs can deliver hEPO mRNA in vitro, it was investigated whether these EVs are also capable of delivering exogenous mRNA (i.e., hEPO mRNA) in vivo. Prior to administration of hEPO mRNA in vivo, blood was acquired from untreated healthy C57BL6/NCrl mice and hEPO protein was examined by human erythropoietin ELISA to confirm that the recipient mice lack and do not express the human form of EPO protein (hEPO). As expected, the plasma of the untreated mice was negative for hEPO protein (FIG. 12).

Figure 3:
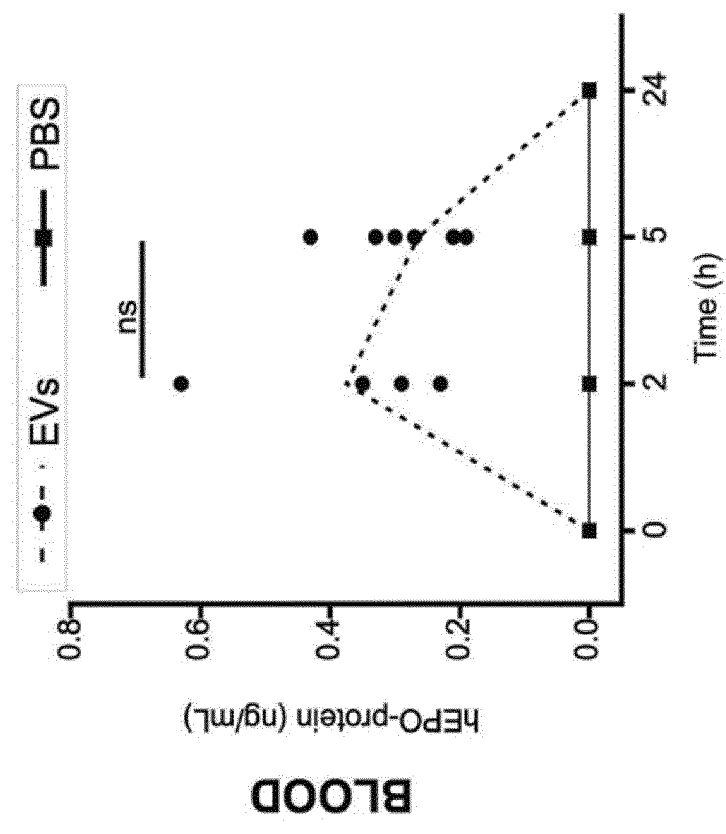
FIG. 3 shows detection of hEPO protein in mouse blood after hEPO mRNA delivery via EVs. Mice were intravenously injected with 100 μL of MC3-EVs containing 1.5 μg of hEPO mRNA (per mouse). The concentrations of hEPO protein in mouse plasma were determined by human erythropoietin ELISA at 0 hours (untreated), 2 hours, 5 hours, and 24 hours after EV injection. hEPO protein was detectable in mouse blood 2 hours after EV injection. Control mice were injected with an equivalent volume of PBS and the mouse plasma was examined for hEPO protein by ELISA. Data are presented from eight replicates (n=8) at each time point, except for 2 hours (n=4). Each dot in the scattered plot represents each replicate (mouse). The plasma hEPO protein after MC3-EVs delivery was compared between 2 hours and 5 hours using a parametric unpaired two-tailed t test (ns: not significant).
Figure 4A:
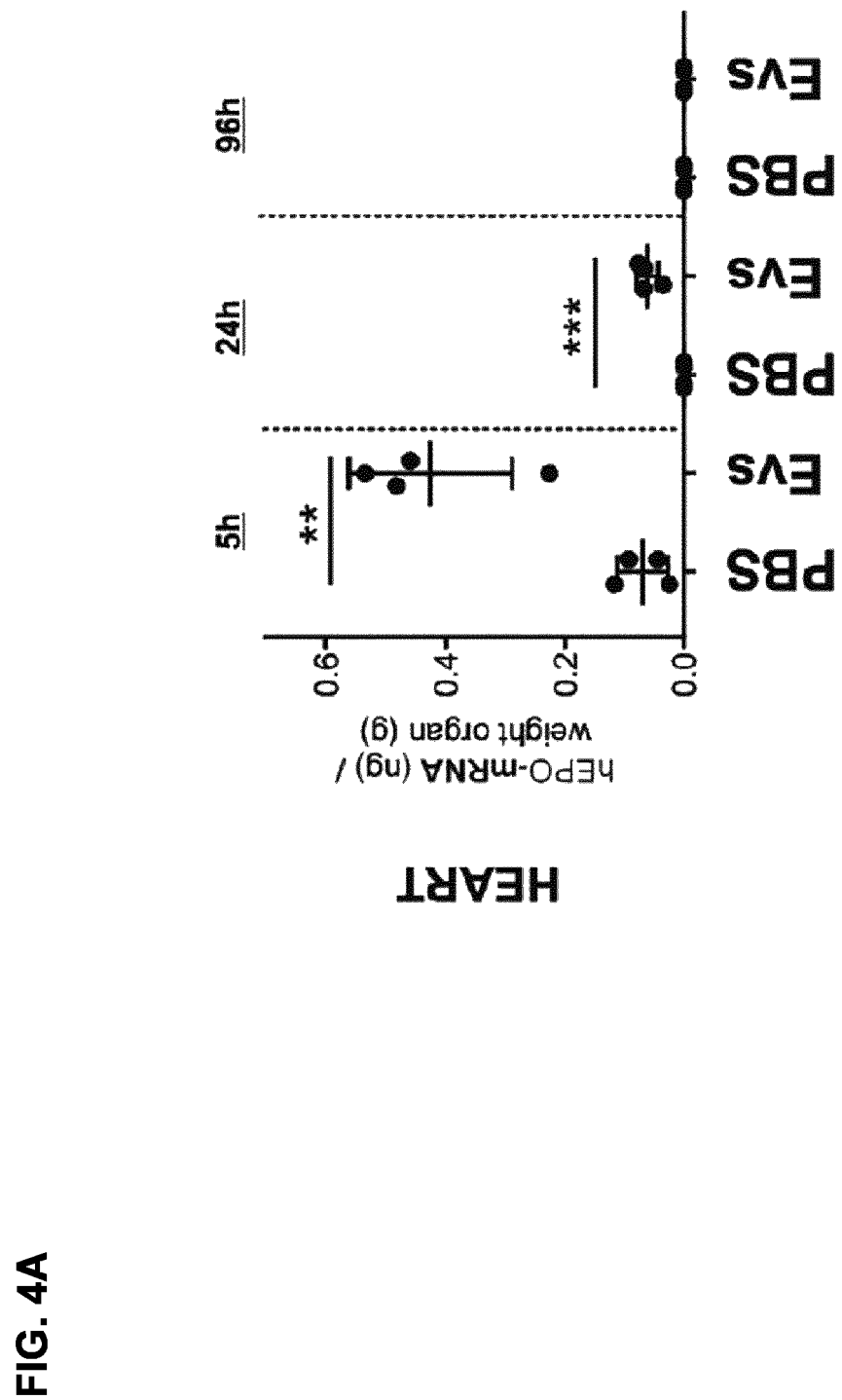
FIG. 4A and FIG. 4B show quantification of hEPO mRNA (FIG. 4A) and hEPO protein (FIG. 4B) in mouse heart following in vivo delivery of hEPO mRNA via EVs. Mice were intravenously injected with 100 μL of MC3-EVs containing 1.5 μg of hEPO mRNA (per mouse). 5 hours, 24 hours, and 96 hours after EV injection, levels of hEPO mRNA and hEPO protein were quantified by RT-qPCR and ELISA, respectively. Mice injected with PBS were used as controls. Data are presented as mean values with standard deviation (SD) of four replicates (n=4) at each time point as a scattered plot. EV treated and untreated groups were compared at each time point using a parametric unpaired two-tailed t test. Significant values are shown as P-values: *P<0.05, P<0.01, *P<0.001.
Figure 4B:
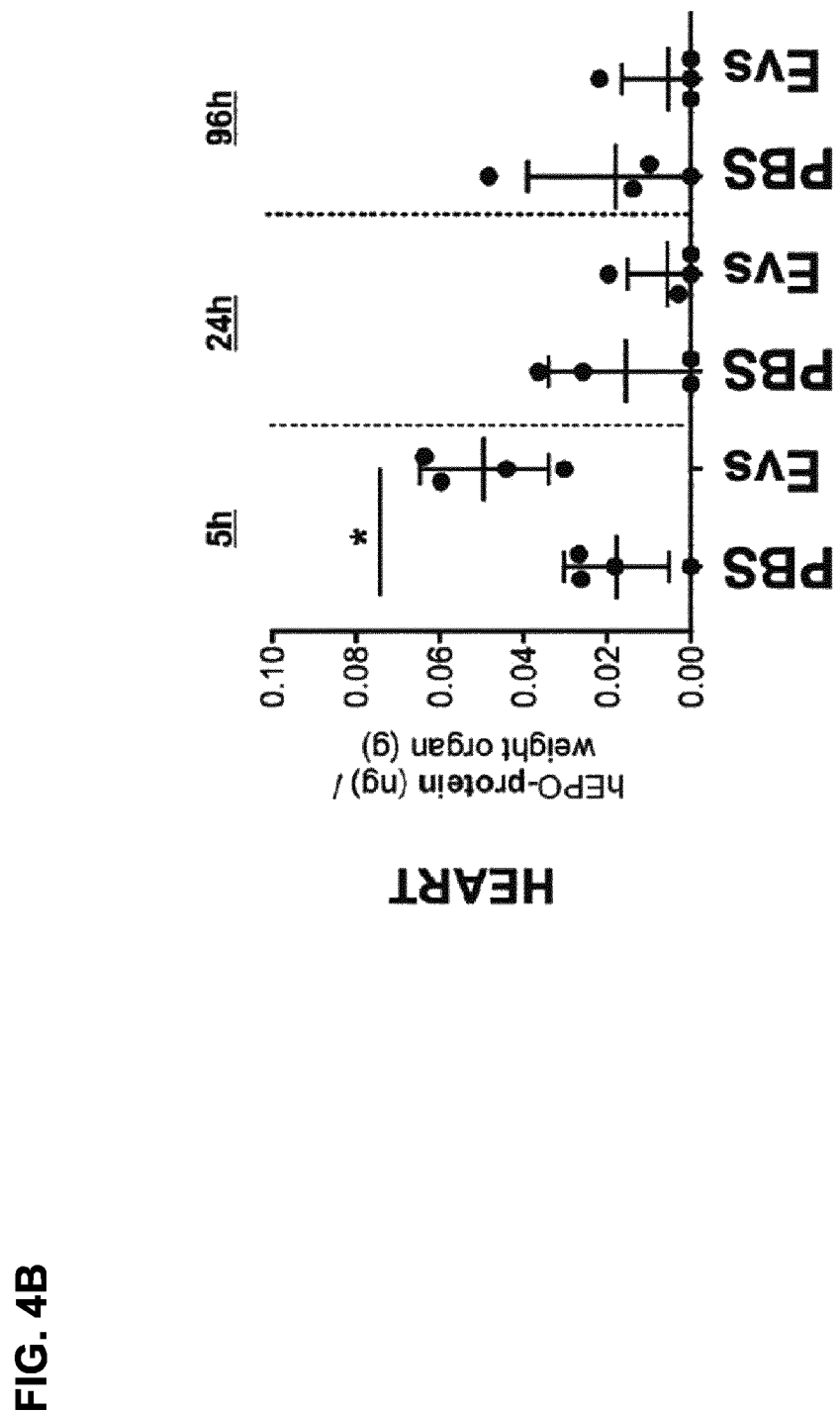
Figure 4C:
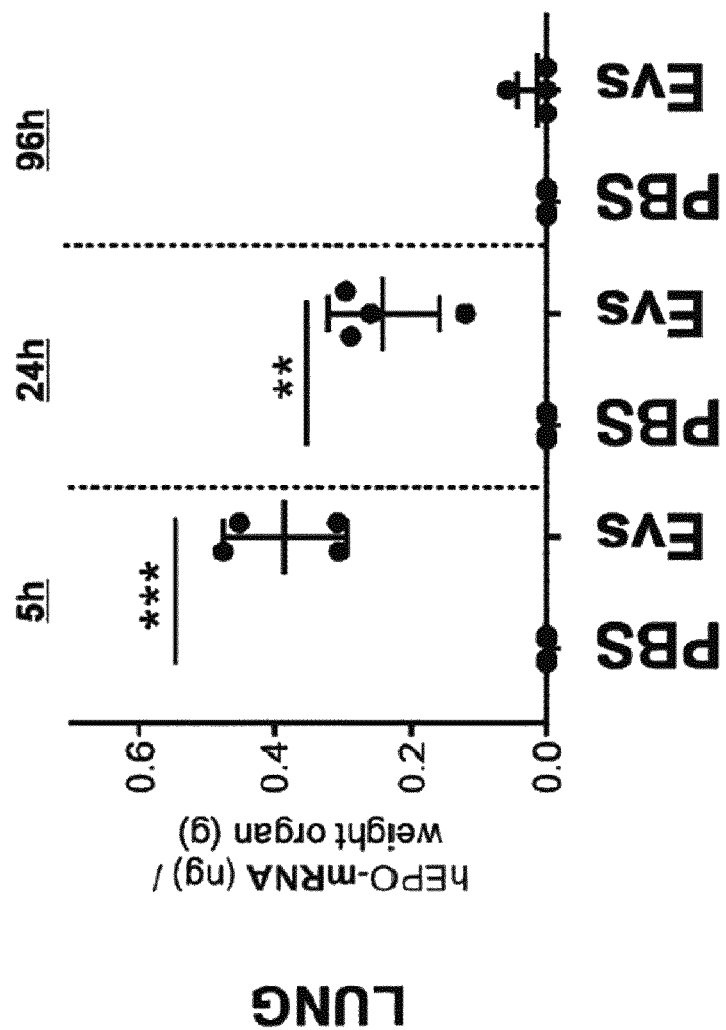
FIG. 4C and FIG. 4D show quantification of hEPO mRNA (FIG. 4C) and hEPO protein (FIG. 4D) in mouse lung. 5 hours, 24 hours, and 96 hours after EV injection (1.5 μg of hEPO mRNA per mouse), levels of hEPO mRNA in lung were quantified by RT-qPCR and levels of hEPO protein were quantified by ELISA. Data are presented as mean values with standard deviation (SD) of four replicates (n=4) at each time point as a scattered plot. EV treated and untreated groups were compared at each time point using a parametric unpaired two-tailed t test. Significant values are shown as P-values: *P<0.05, P<0.01, *P<0.001.
Figure 4D:
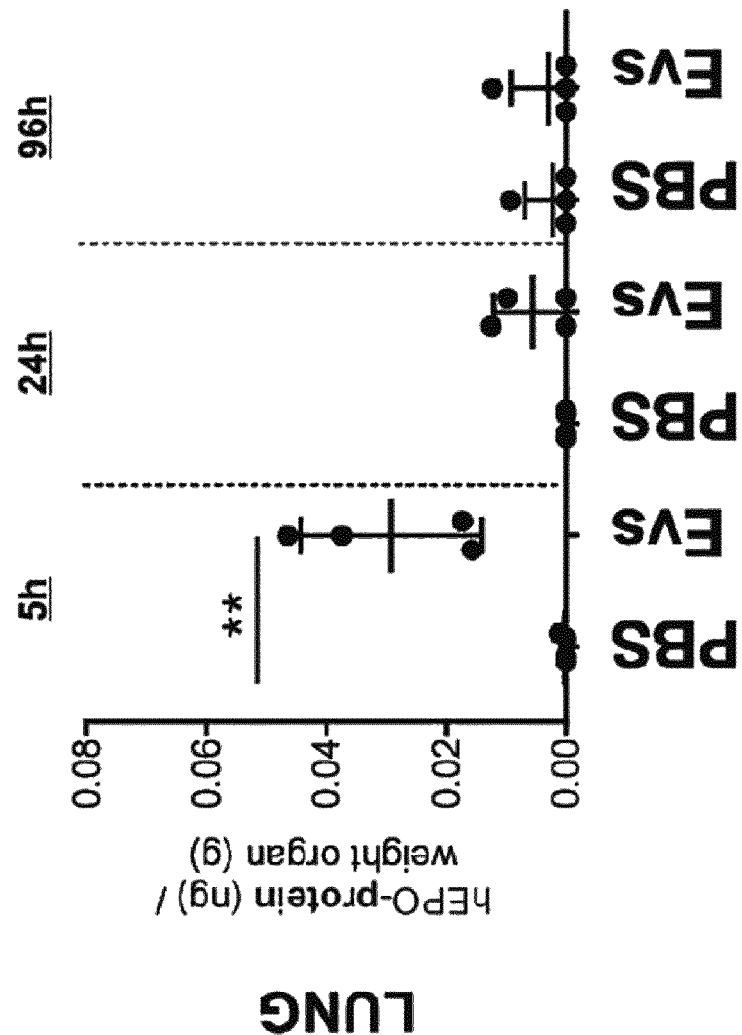
Figure 4E:
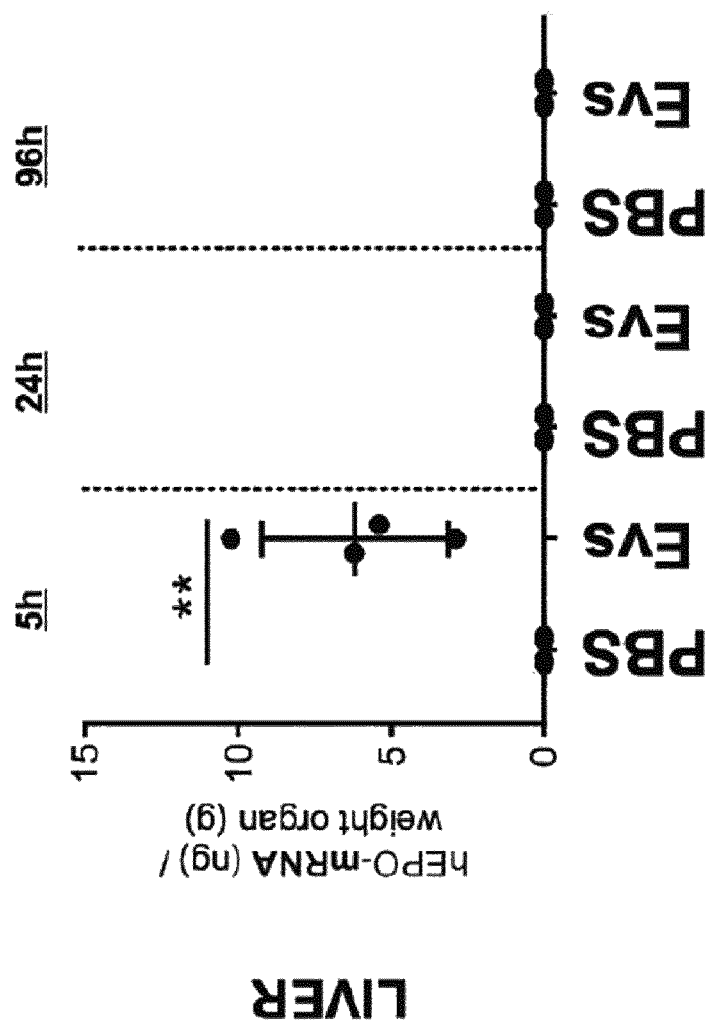
FIG. 4E and FIG. 4F show quantification of hEPO mRNA (FIG. 4E) and hEPO protein (FIG. 4F) in mouse liver. 5 hours, 24 hours, and 96 hours after EV injection (1.5 μg of hEPO mRNA per mouse), levels of hEPO mRNA in liver were quantified by RT-qPCR and levels of hEPO protein were quantified by ELISA. The highest amount of hEPO protein was detected in the liver, as compared to all other organs evaluated. Data are presented as mean values with standard deviation (SD) of four replicates (n=4) at each time point as a scattered plot. EV treated and untreated groups were compared at each time point using a parametric unpaired two-tailed t test. Significant values are shown as P-values: *P<0.05, P<0.01, *P<0.001.
Figure 4F:
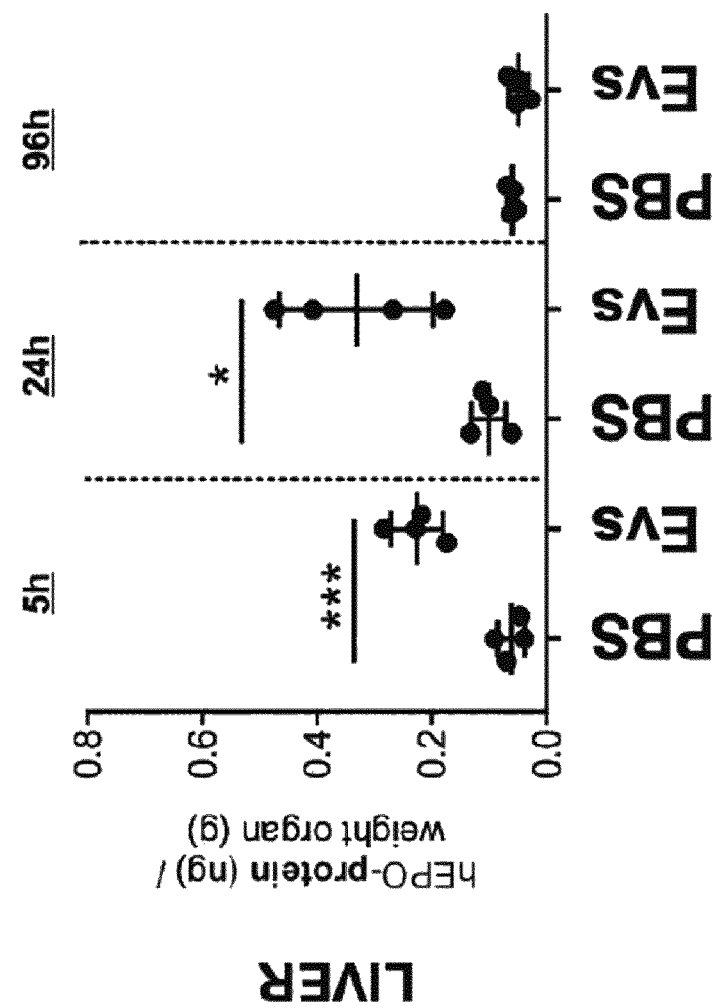
Figure 4G:
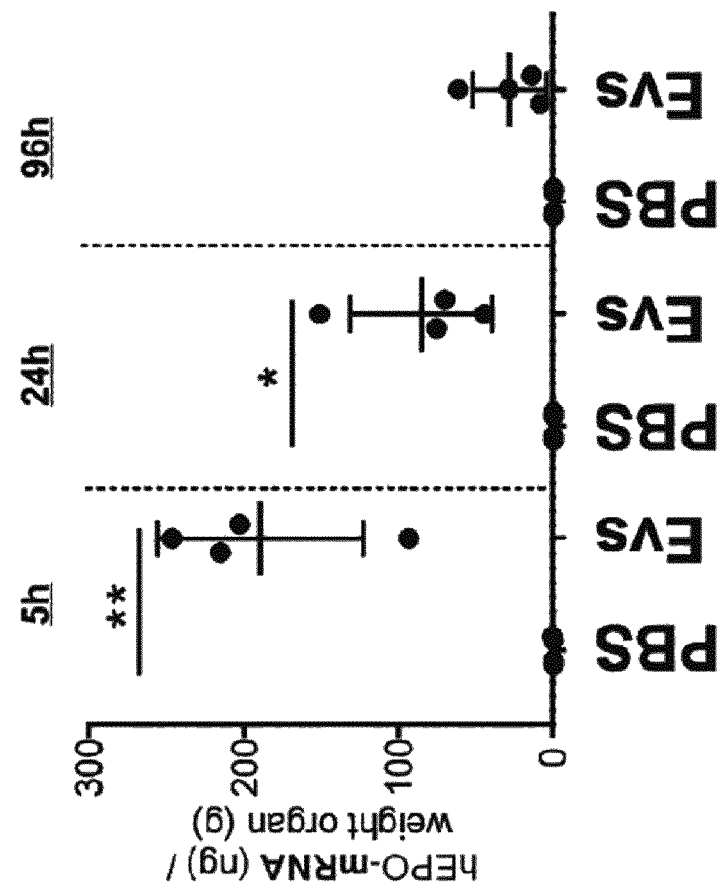
FIG. 4G and FIG. 4H show quantification of hEPO mRNA (FIG. 4G) and hEPO protein (FIG. 4H) in mouse spleen. 5 hours, 24 hours, and 96 hours after EV injection (1.5 µg of hEPO mRNA per mouse), levels of hEPO mRNA in spleen were quantified by RT-qPCR and levels of hEPO protein were quantified by ELISA. The highest amount of hEPO mRNA was detected in the spleen, as compared to all other organs evaluated. Data are presented as mean values with standard deviation (SD) of four replicates (n=4) at each time point as a scattered plot. EV treated and untreated groups were compared at each time point using a parametric unpaired two-tailed t test. Significant values are shown as P-values: *$P<0.05$, $P<0.01$, *$P<0.001$.
Figure 4H:
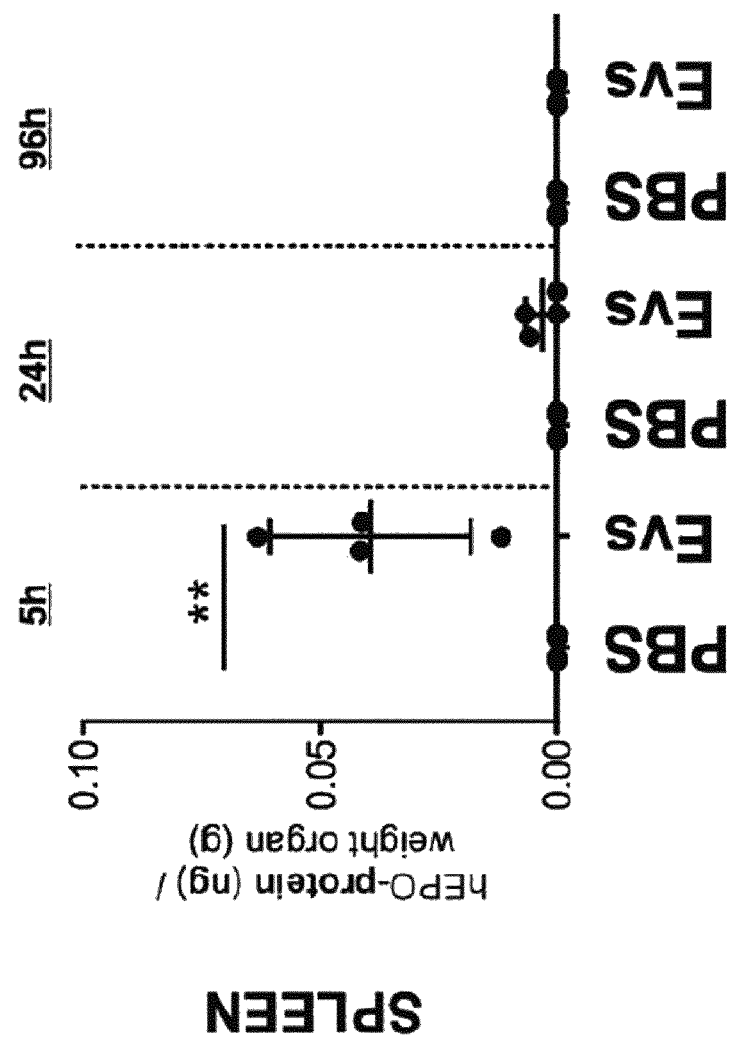
Figure 4I:
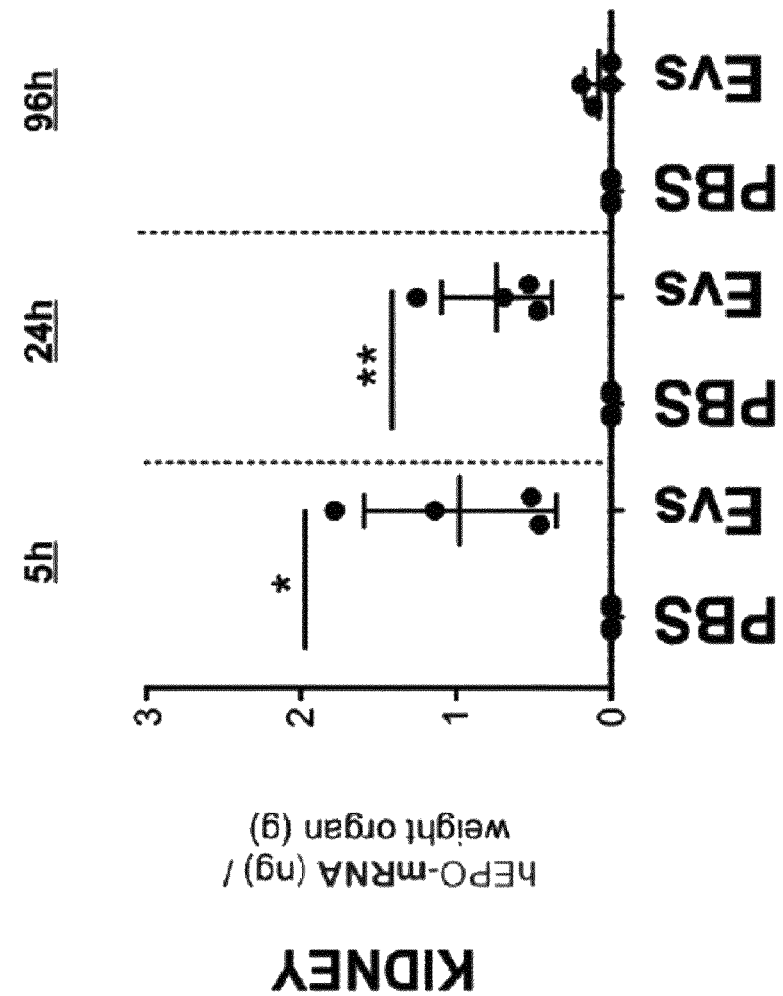
FIG. 4I and FIG. 4J show quantification of hEPO mRNA (FIG. 4I) and hEPO protein (FIG. 4J) in mouse kidney. 5 hours, 24 hours, and 96 hours after EV injection (1.5 µg of hEPO mRNA per mouse), levels of hEPO mRNA in kidney were quantified by RT-qPCR and levels of hEPO protein was quantified by ELISA. Data are presented as mean values with standard deviation (SD) of four replicates (n=4) at each time point as a scattered plot. EV treated and untreated groups were compared at each time point using a parametric unpaired two-tailed t test. Significant values are shown as P-values: *$P<0.05$, $P<0.01$, *$P<0.001$.
Figure 4J:
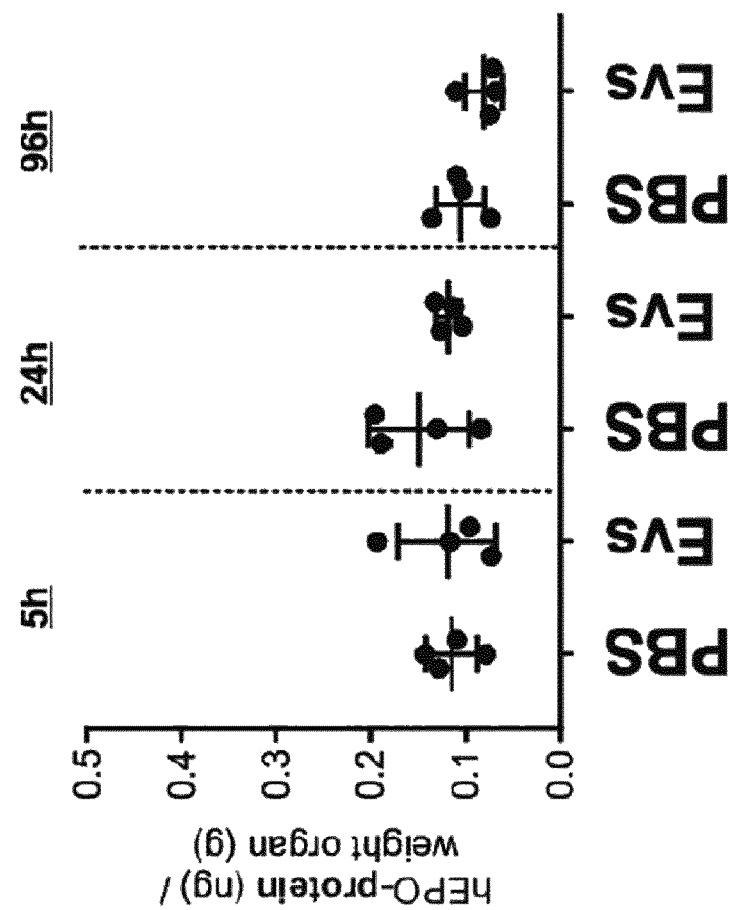
Figure 4K:
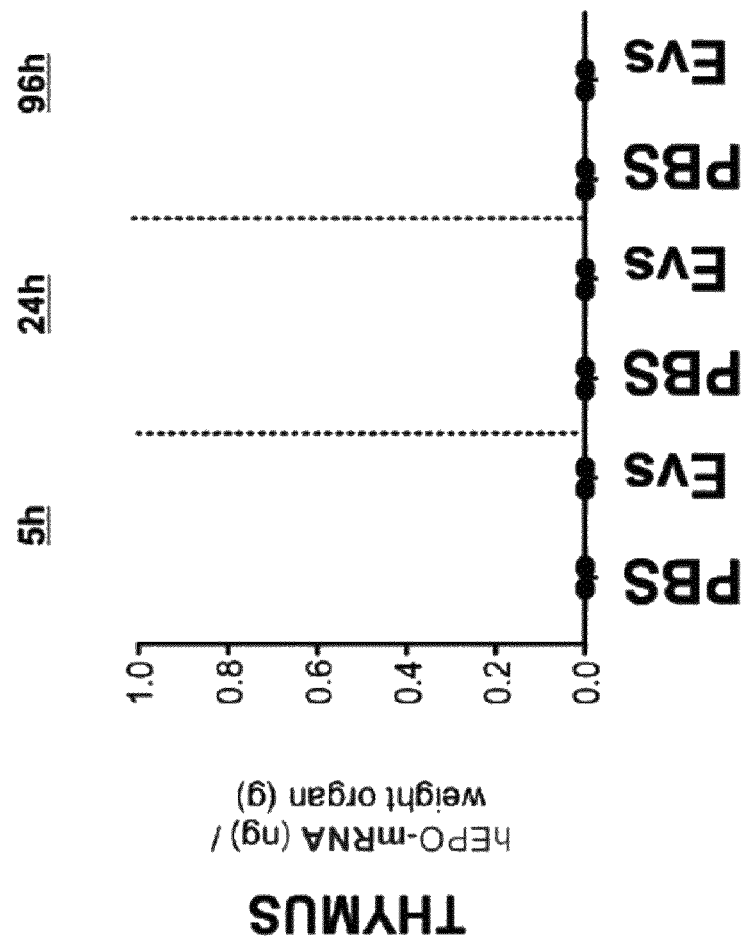
FIG. 4K and FIG. 4L show quantification of hEPO mRNA (FIG. 4K) and hEPO protein (FIG. 4L) in mouse thymus. 5 hours, 24 hours, and 96 hours after EV injection (1.5 µg of hEPO mRNA per mouse), levels of hEPO mRNA in thymus were quantified by RT-qPCR and levels of hEPO protein was quantified by ELISA. Data are presented as mean values with standard deviation (SD) of four replicates (n=4) at each time point as a scattered plot. EV treated and untreated groups were compared at each time point using a parametric unpaired two-tailed t test. Significant values are shown as P-values: *$P<0.05$, $P<0.01$, *$P<0.001$.
Figure 4L:
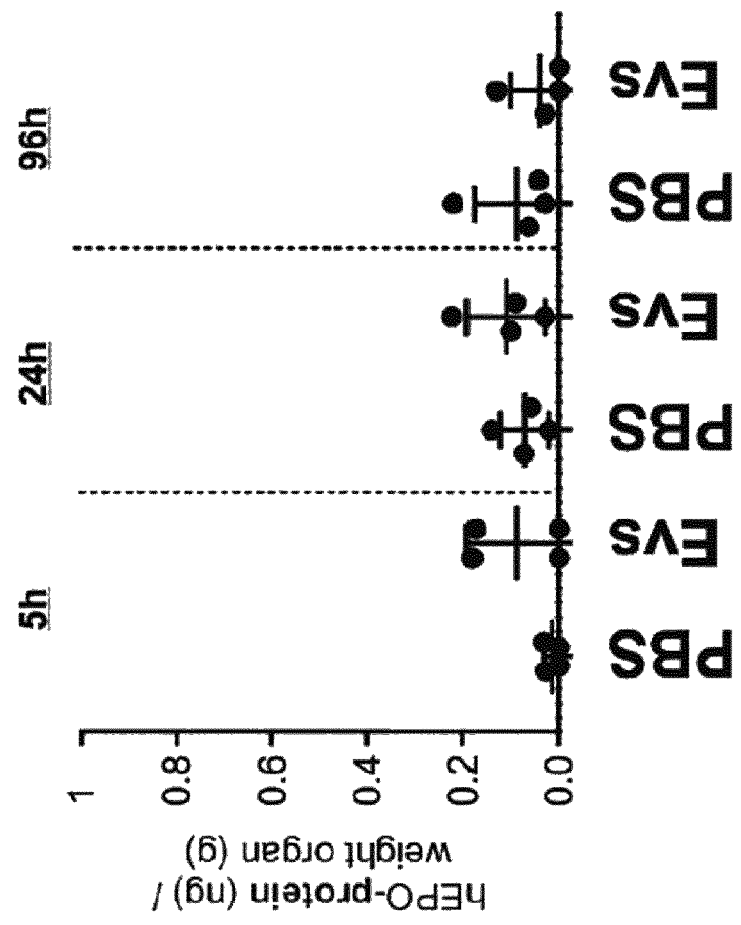
Figure 4M:
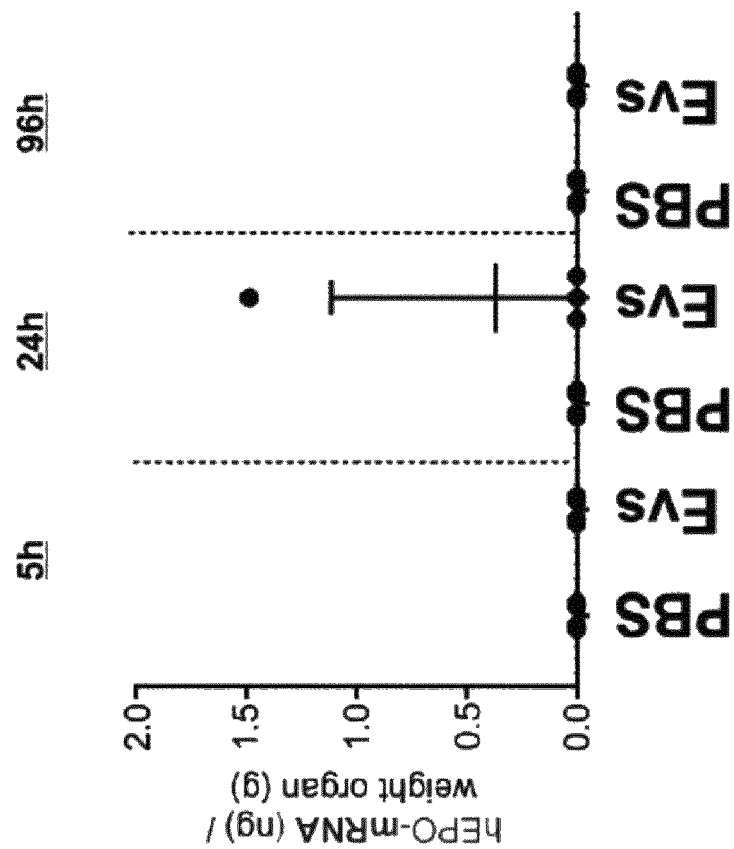
FIG. 4M and FIG. 4N show quantification of hEPO mRNA (FIG. 4M) and hEPO protein (FIG. 4N) in mouse pancreas. 5 hours, 24 hours, and 96 hours after EV injection (1.5 µg of hEPO mRNA per mouse), levels of hEPO mRNA in pancreas were quantified by RT-qPCR and levels of hEPO protein was quantified by ELISA. Data are presented as mean values with standard deviation (SD) of four replicates (n=4) at each time point as a scattered plot. EV treated and untreated groups were compared at each time point using a parametric unpaired two-tailed t test. Significant values are shown as P-values: *$P<0.05$, $P<0.01$, *$P<0.001$.
Figure 4N:
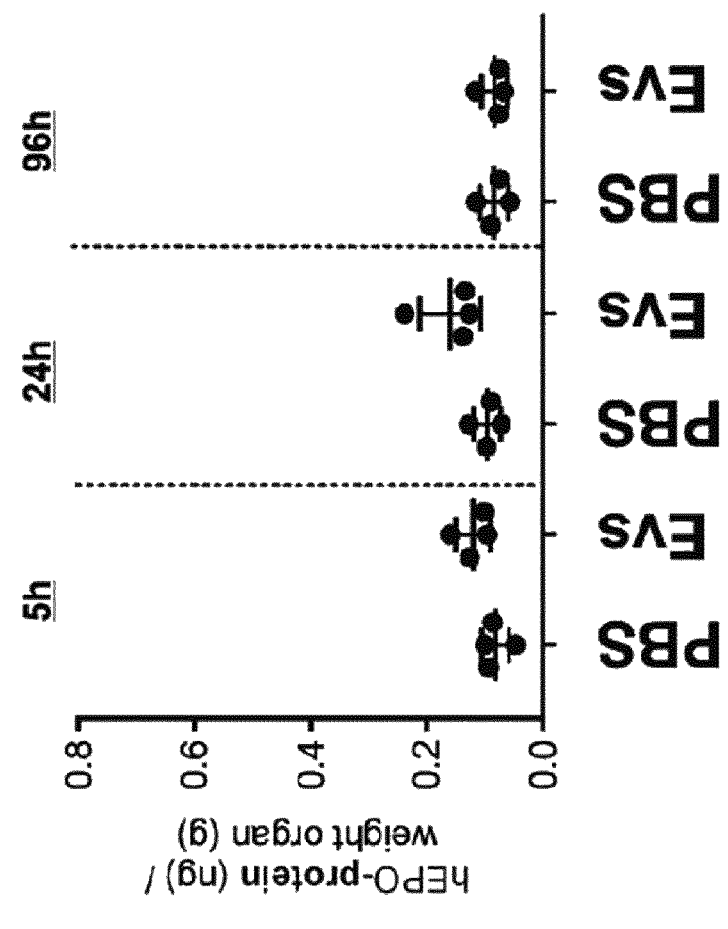
Figure 40:
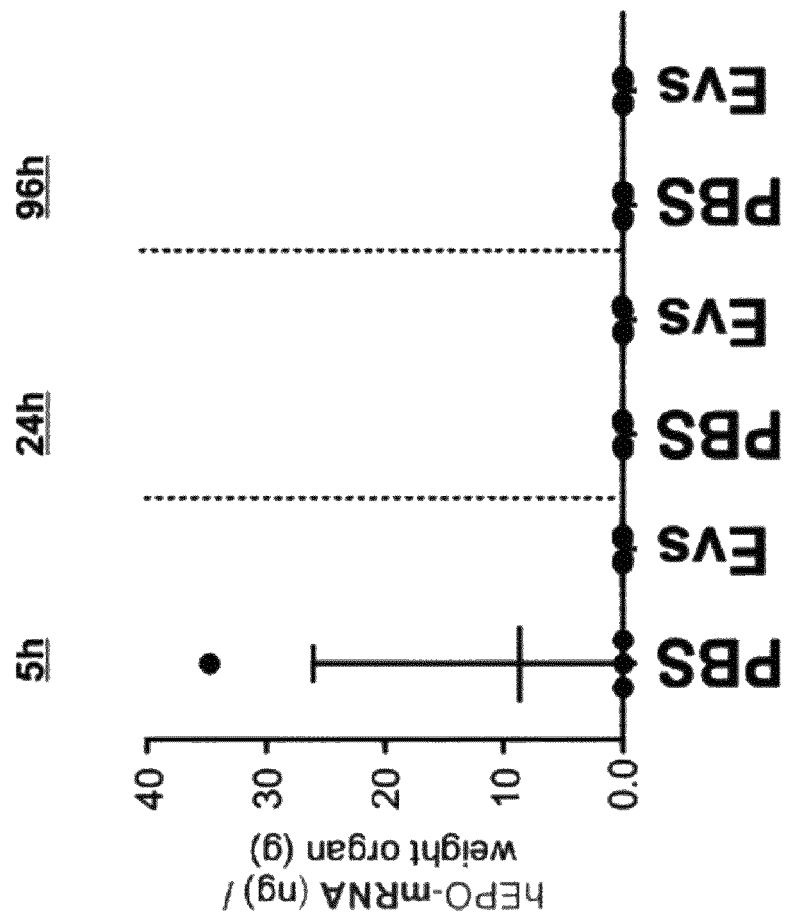
Figure 4P:
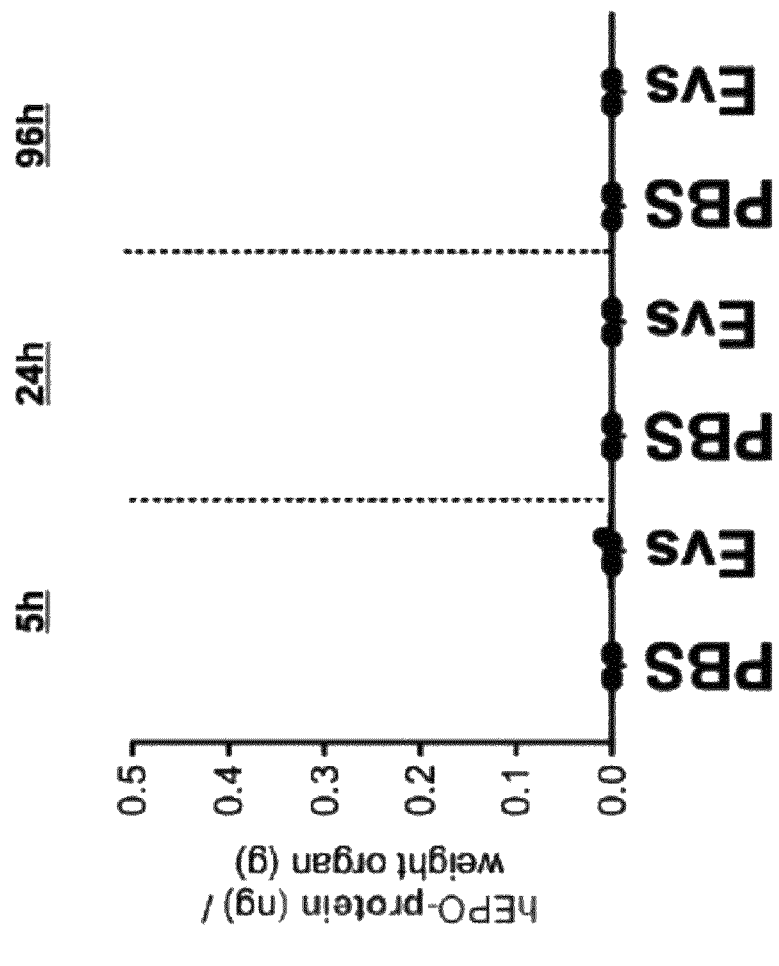

Next, C57BL6/NCrl mice were injected with single intravenous dose of MC3-EVs (1.5 µg hEPO mRNA per mouse), and the production of hEPO protein was examined in both plasma and organs. hEPO protein was detected in mouse plasma after 2 hours of EV-mediated hEPO mRNA delivery and persisted for 24 hours, showing that EVs can deliver exogenous mRNA to mice and cause the production of a protein of interest (FIG. 3). Additionally, the presence of hEPO mRNA and hEPO protein was examined in eight organs of the mice sacrificed at different time points (5 hours, 24 hours, and 96 hours). Results suggested that EVs not only can deliver hEPO mRNA to different organs, but also allow the production of hEPO protein, indicating that EVs can deliver a functional mRNA to organs (FIG. 4A-P). In heart, lung, liver and spleen, hEPO mRNA and hEPO protein were detectable (FIG. 4A-H). In heart and lung, hEPO mRNA as well as the translated hEPO protein were detectable after 5 hours of EV-mediated mRNA delivery, and mRNA persisted for 24 hours (FIG. 4A-D). In liver, hEPO mRNA was detectable only after 5 hours of EV delivery, but translated hEPO protein was detectable after 5 hours and persisted for 24 hours (FIG. 4E and FIG. 4F). However, in the spleen, the pattern was opposite. In spleen, hEPO mRNA was detectable after 5 hours and persisted for 24 hours, but translated hEPO protein was detectable only after 5 hours (FIG. 4G and FIG. 4H).

Notably, among all four organs positive for hEPO mRNA, liver was the organ with the highest amount of hEPO protein (FIG. 4F), whereas spleen was the organ with the highest amount of hEPO mRNA (FIG. 4G). The amount of hEPO protein detected in the spleen at 5 hours was comparable to the amount detected in other organs. Kidney showed a relatively small amount of hEPO mRNA, but no protein was detectable (FIG. 4I and FIG. 4J). In three of the eight organs analyzed (thymus, pancreas, and brain), hEPO mRNA and hEPO protein were not detectable (FIG. 4K-P).

Figure 13:
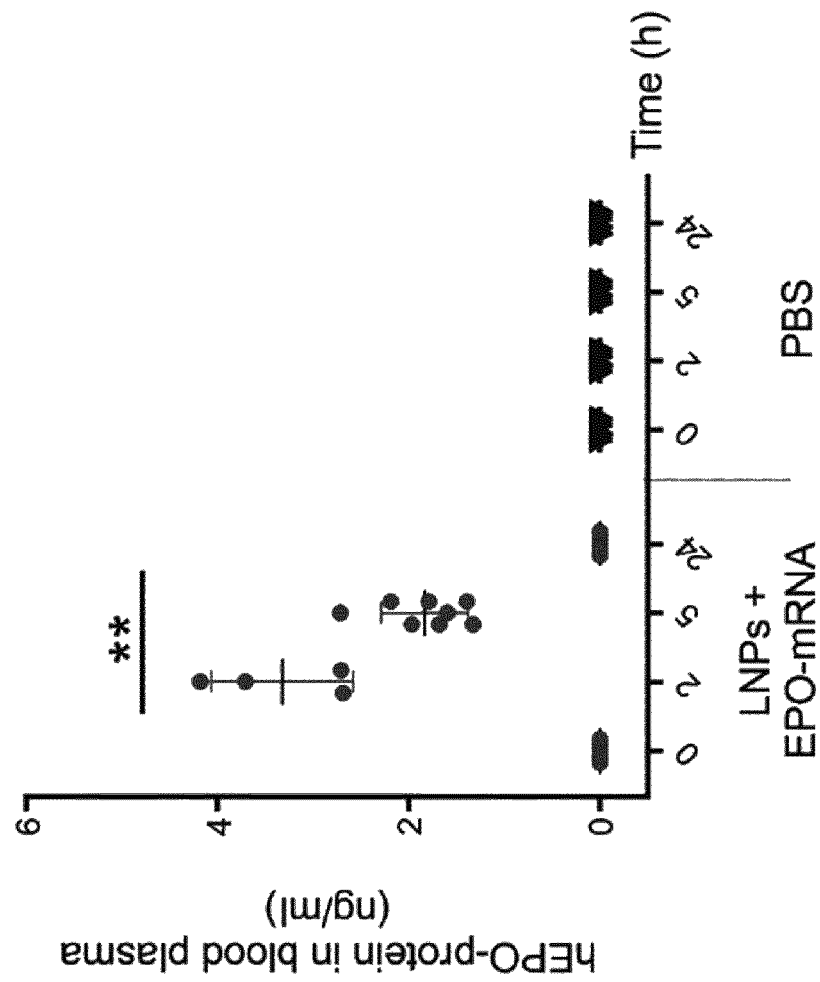
FIG. 13 shows detection of hEPO protein in mouse blood following delivery of hEPO mRNA via MC3-LNPs. Mice were intravenously injected with 100 μL of MC3-LNPs, containing 1.5 μg of hEPO mRNA (per mouse), or with the equivalent volume of PBS as a control. The concentrations of hEPO protein in mouse plasma were determined by ELISA at 0 hours, 2 hours, 5 hours, and 24 hours after injection. Data are presented from 8 mice (n=8), except for the 2 hour time point (n=4). Each dot in the scattered plot represents each replicate (mouse). The number of untreated mice (PBS) was n=8. The plasma hEPO protein from MC3-LNP delivery was compared between 2 hours and 5 hours using a parametric unpaired two-tailed t test (*P<0.05, P<0.01, *P<0.001, ****P<0.0001, and ns=not significant).
Figure 14A:
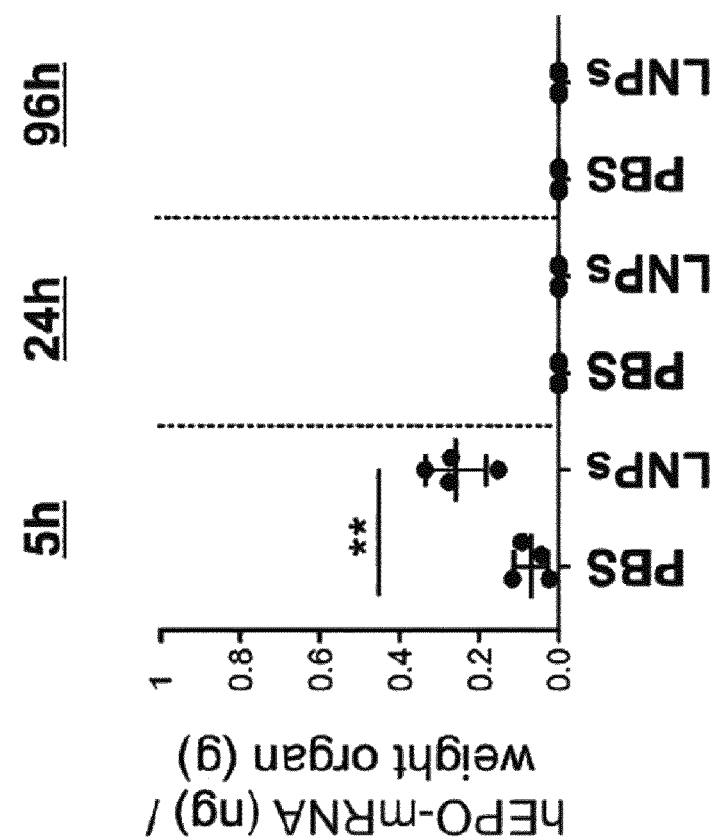
FIG. 14A and FIG. 14B show quantification of hEPO mRNA (FIG. 14A) and hEPO protein (FIG. 14B) in mouse heart. Mice were intravenously injected with 100 μL of MC3-LNPs, containing 1.5 μg of hEPO mRNA (per mouse), or with the equivalent volume of PBS as a control. Levels of hEPO mRNA and hEPO protein were quantified 5 hours, 24 hours, and 96 hours after injection by RT-qPCR and ELISA, respectively. Data are presented as total amount of hEPO mRNA or protein detected in the entire organ normalized to organ weight. For each time point, and each kind of treatment (LNPs or PBS), four mice (n=4) were used. Data are presented as mean values with standard deviation (SD) of four replicates (n=4), at each time point. Each dot in the scattered plot represents each replicate. For each time point, the MC3-LNPs and PBS groups were compared using a parametric unpaired two-tailed t test. Only significant P-values are shown: *P<0.05, P<0.01, *P<0.001, ****P<0.0001.
Figure 14B:
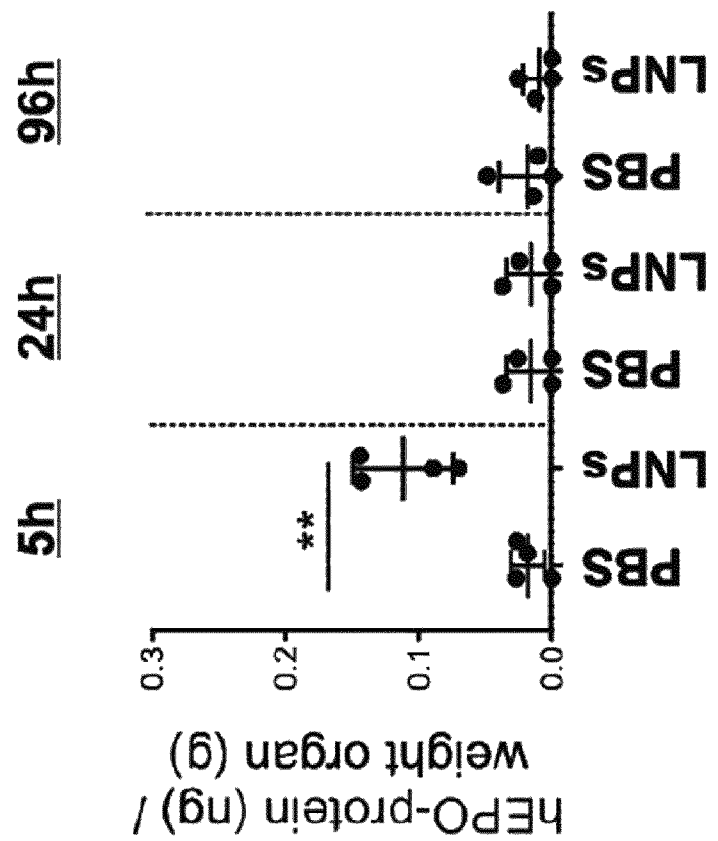
Figure 14C:
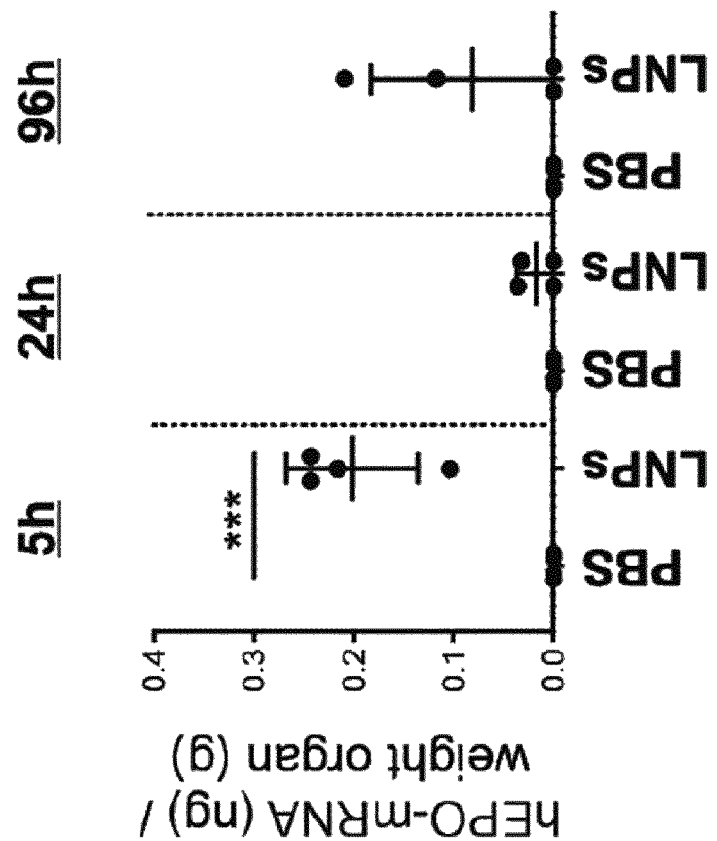
FIG. 14C and FIG. 14D show quantification of hEPO mRNA (FIG. 14C) and hEPO protein (FIG. 14D) in mouse lung. Mice were intravenously injected with 100 μL of MC3-LNPs, containing 1.5 μg of hEPO mRNA (per mouse), or with the equivalent volume of PBS as a control. Levels of hEPO mRNA and hEPO protein were quantified 5 hours, 24 hours, and 96 hours after injection by RT-qPCR and ELISA, respectively. Data are presented as total amount of hEPO mRNA or protein detected in the entire organ normalized to organ weight. For each time point, and each kind of treatment (LNPs or PBS), four mice (n=4) were used. Data are presented as mean values with standard deviation (SD) of four replicates (n=4), at each time point. Each dot in the scattered plot represents each replicate. For each time point, the MC3-LNPs and PBS groups were compared using a parametric unpaired two-tailed t test. Only significant P-values are shown: *P<0.05, P<0.01, *P<0.001, ****P<0.0001.
Figure 14D:
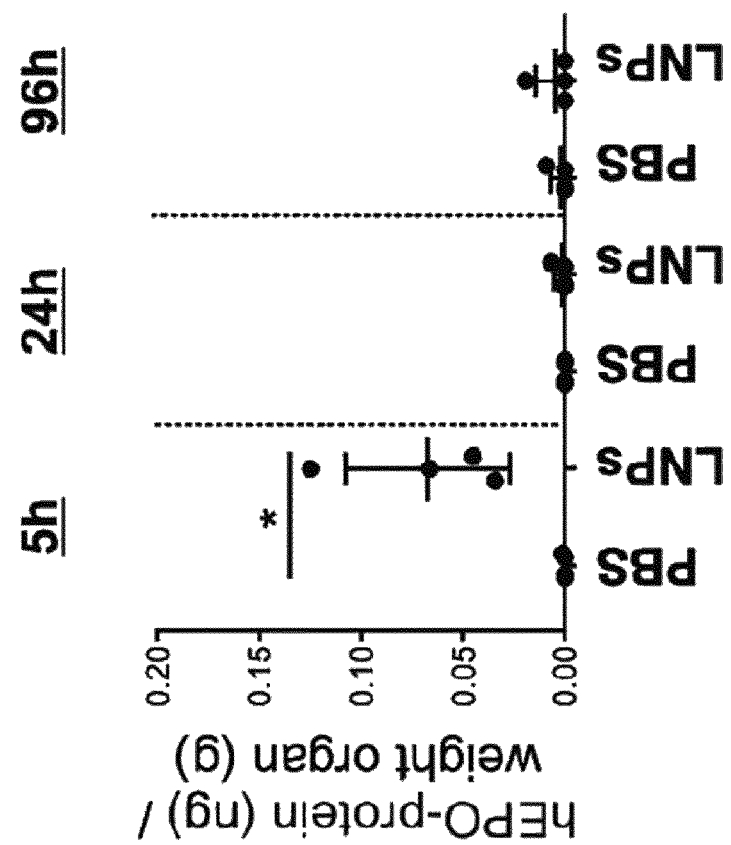
Figure 14E:
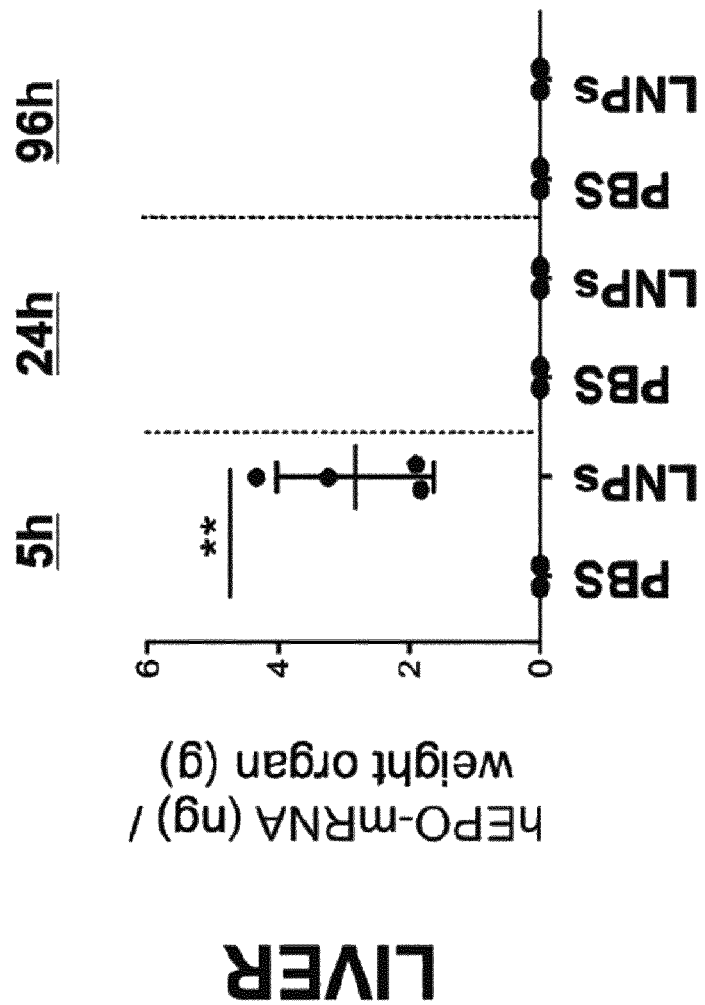
FIG. 14E and FIG. 14F show quantification of hEPO mRNA (FIG. 14E) and hEPO protein (FIG. 14F) in mouse liver. Mice were intravenously injected with 100 μL of MC3-LNPs, containing 1.5 μg of hEPO mRNA (per mouse), or with the equivalent volume of PBS as a control. Levels of hEPO mRNA and hEPO protein were quantified 5 hours, 24 hours, and 96 hours after injection by RT-qPCR and ELISA, respectively. Data are presented as total amount of hEPO mRNA or protein detected in the entire organ normalized to organ weight. For each time point, and each kind of treatment (LNPs or PBS), four mice (n=4) were used. Data are presented as mean values with standard deviation (SD) of four replicates (n=4), at each time point. Each dot in the scattered plot represents each replicate. For each time point, the MC3-LNPs and PBS groups were compared using a parametric unpaired two-tailed t test. Only significant P-values are shown: *P<0.05, P<0.01, *P<0.001, ****P<0.0001.
Figure 14F:
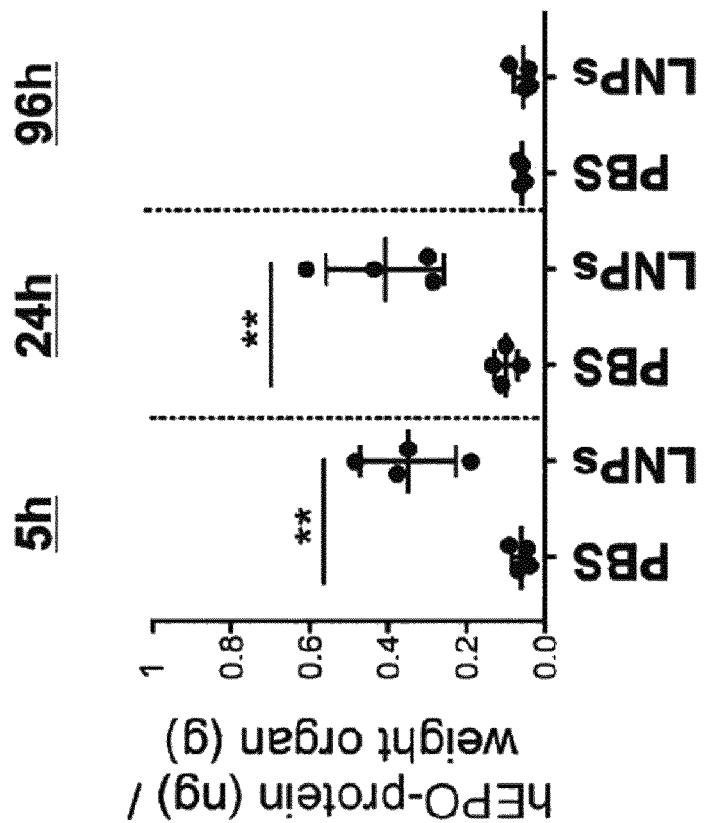
Figure 14G:
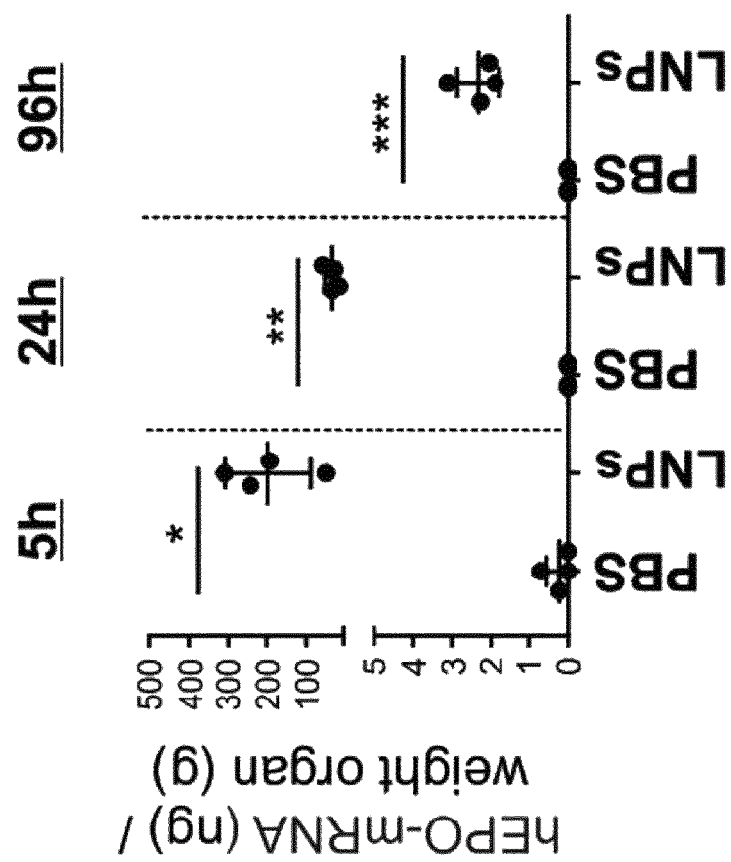
FIG. 14G and FIG. 14H show quantification of hEPO mRNA (FIG. 14G) and hEPO protein (FIG. 14H) in mouse spleen. Mice were intravenously injected with 100 μL of MC3-LNPs, containing 1.5 μg of hEPO mRNA (per mouse), or with the equivalent volume of PBS as a control. Levels of hEPO mRNA and hEPO protein were quantified 5 hours, 24 hours, and 96 hours after injection by RT-qPCR and ELISA, respectively. Data are presented as total amount of hEPO mRNA or protein detected in the entire organ normalized to organ weight. For each time point, and each kind of treatment (LNPs or PBS), four mice (n=4) were used. Data are presented as mean values with standard deviation (SD) of four replicates (n=4), at each time point. Each dot in the scattered plot represents each replicate. For each time point, the MC3-LNPs and PBS groups were compared using a parametric unpaired two-tailed t test. Only significant P-values are shown: *P<0.05, P<0.01, *P<0.001, ****P<0.0001.
Figure 14H:
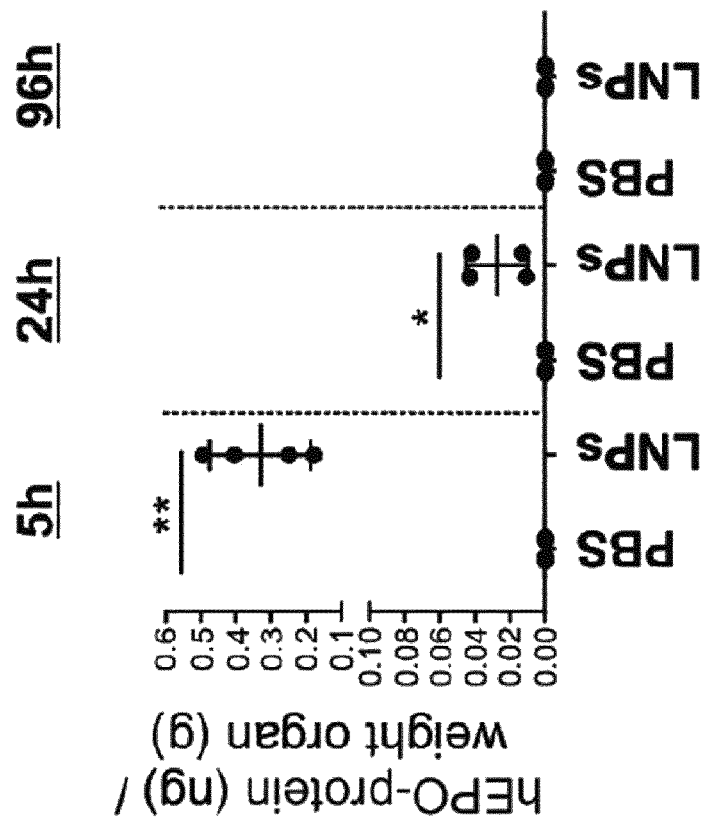
Figure 14I:
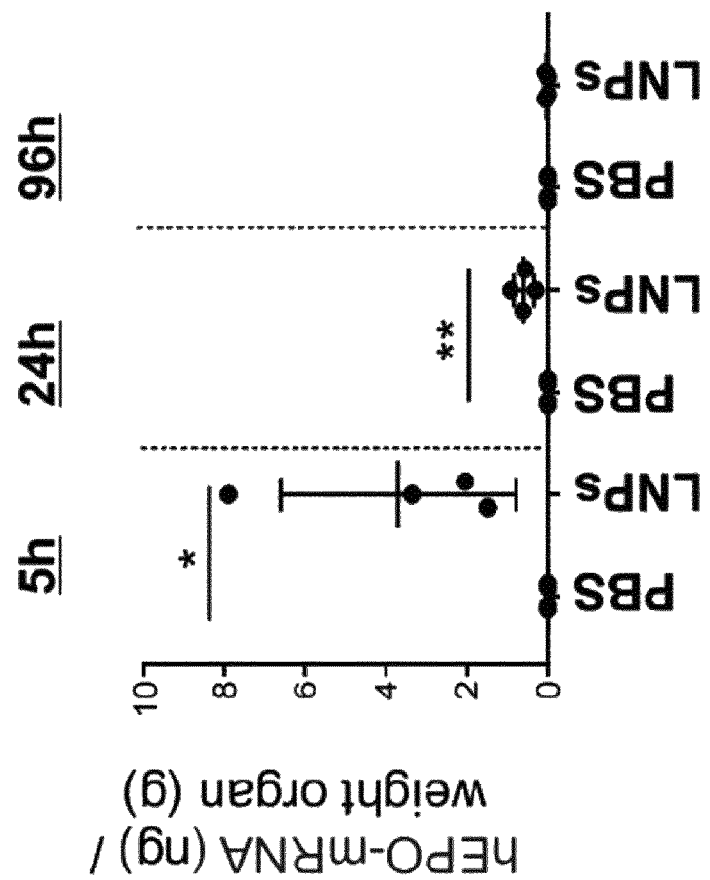
FIG. 14I and FIG. 14J show quantification of hEPO mRNA (FIG. 14I) and hEPO protein (FIG. 14J) in mouse kidney. Mice were intravenously injected with 100 μL of MC3-LNPs, containing 1.5 μg of hEPO mRNA (per mouse), or with the equivalent volume of PBS as a control. Levels of hEPO mRNA and hEPO protein were quantified 5 hours, 24 hours, and 96 hours after injection by RT-qPCR and ELISA, respectively. Data are presented as total amount of hEPO mRNA or protein detected in the entire organ normalized to organ weight. For each time point, and each kind of treatment (LNPs or PBS), four mice (n=4) were used. Data are presented as mean values with standard deviation (SD) of four replicates (n=4), at each time point. Each dot in the scattered plot represents each replicate. For each time point, the MC3-LNPs and PBS groups were compared using a parametric unpaired two-tailed t test. Only significant P-values are shown: *P<0.05, P<0.01, *P<0.001, ****P<0.0001.
Figure 14J:
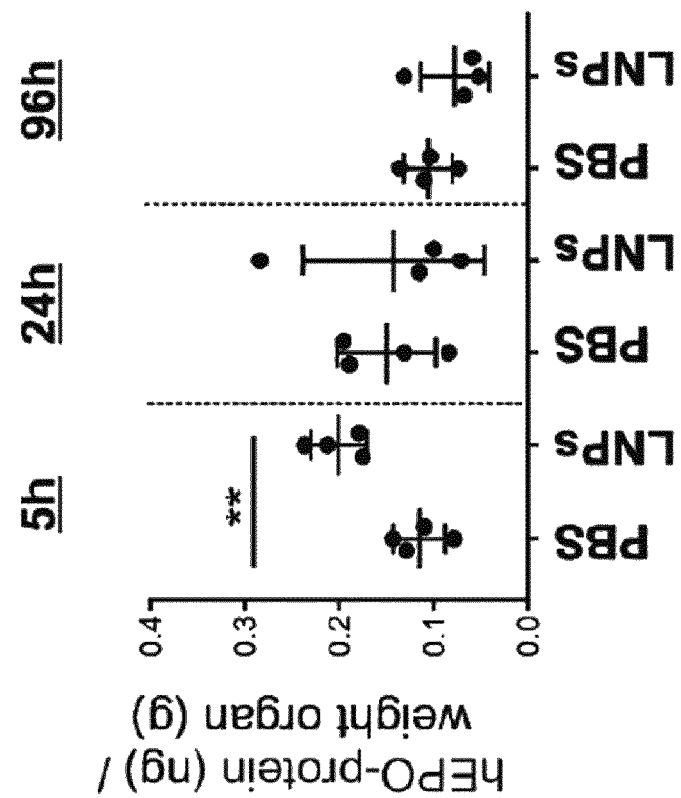
Figure 14K:
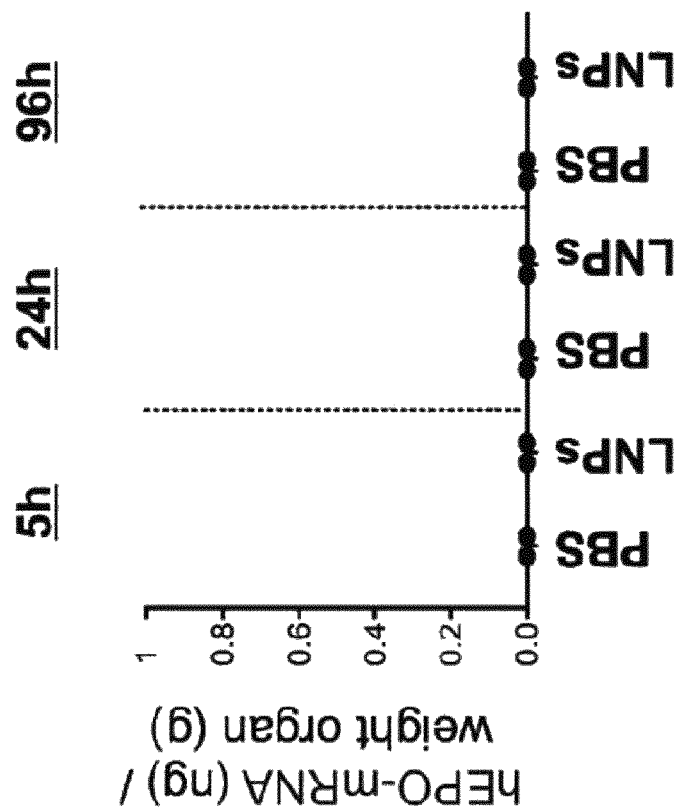
FIG. 14K and FIG. 14L show quantification of hEPO mRNA (FIG. 14K) and hEPO protein (FIG. 14L) in mouse thymus. Mice were intravenously injected with 100 μL of MC3-LNPs, containing 1.5 μg of hEPO mRNA (per mouse), or with the equivalent volume of PBS as a control. Levels of hEPO mRNA and hEPO protein were quantified 5 hours, 24 hours, and 96 hours after injection by RT-qPCR and ELISA, respectively. Data are presented as total amount of hEPO mRNA or protein detected in the entire organ normalized to organ weight. For each time point, and each kind of treatment (LNPs or PBS), four mice (n=4) were used. Data are presented as mean values with standard deviation (SD) of four replicates (n=4), at each time point. Each dot in the scattered plot represents each replicate. For each time point, the MC3-LNPs and PBS groups were compared using a parametric unpaired two-tailed t test. Only significant P-values are shown: *P<0.05, P<0.01, *P<0.001, ****P<0.0001.
Figure 14L:
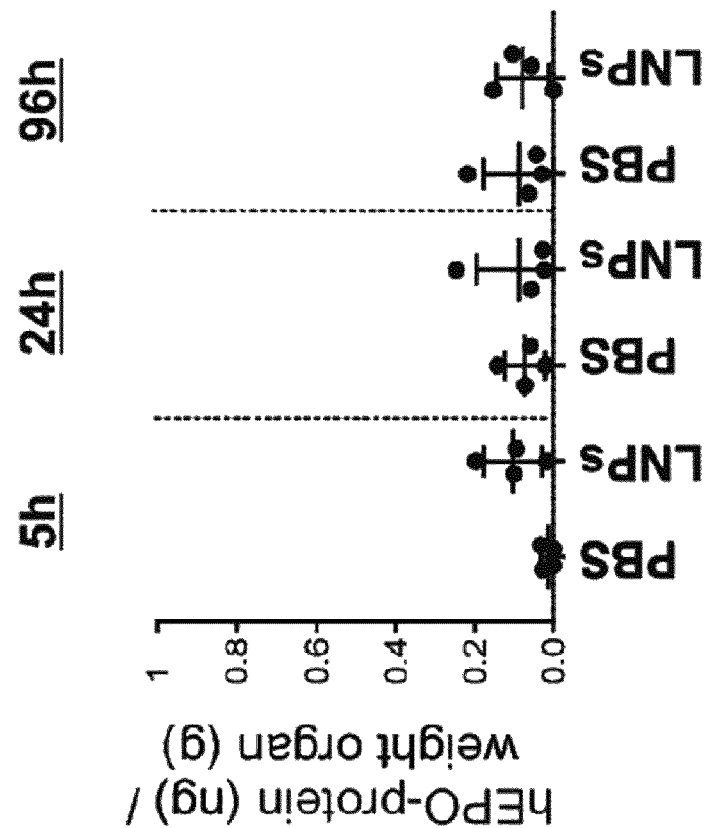
Figure 14M:
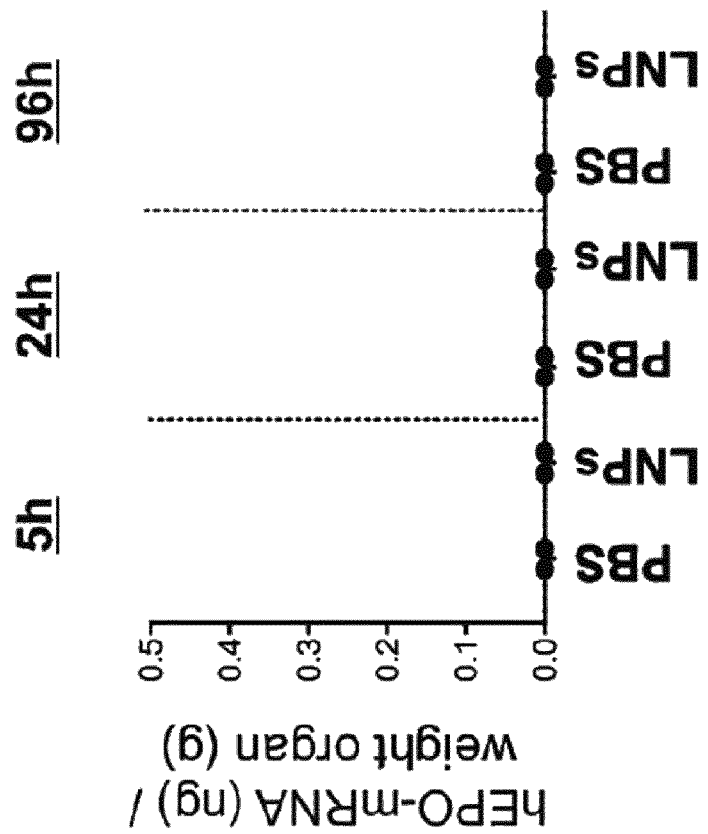
FIG. 14M and FIG. 14N show quantification of hEPO mRNA (FIG. 14M) and hEPO protein (FIG. 14N) in mouse pancreas. Mice were intravenously injected with 100 μL of MC3-LNPs, containing 1.5 μg of hEPO mRNA (per mouse), or with the equivalent volume of PBS as a control. Levels of hEPO mRNA and hEPO protein were quantified 5 hours, 24 hours, and 96 hours after injection by RT-qPCR and ELISA, respectively. Data are presented as total amount of hEPO mRNA or protein detected in the entire organ normalized to organ weight. For each time point, and each kind of treatment (LNPs or PBS), four mice (n=4) were used. Data are presented as mean values with standard deviation (SD) of four replicates (n=4), at each time point. Each dot in the scattered plot represents each replicate. For each time point, the MC3-LNPs and PBS groups were compared using a parametric unpaired two-tailed t test. Only significant P-values are shown: *P<0.05, P<0.01, *P<0.001, ****P<0.0001.
Figure 14N:
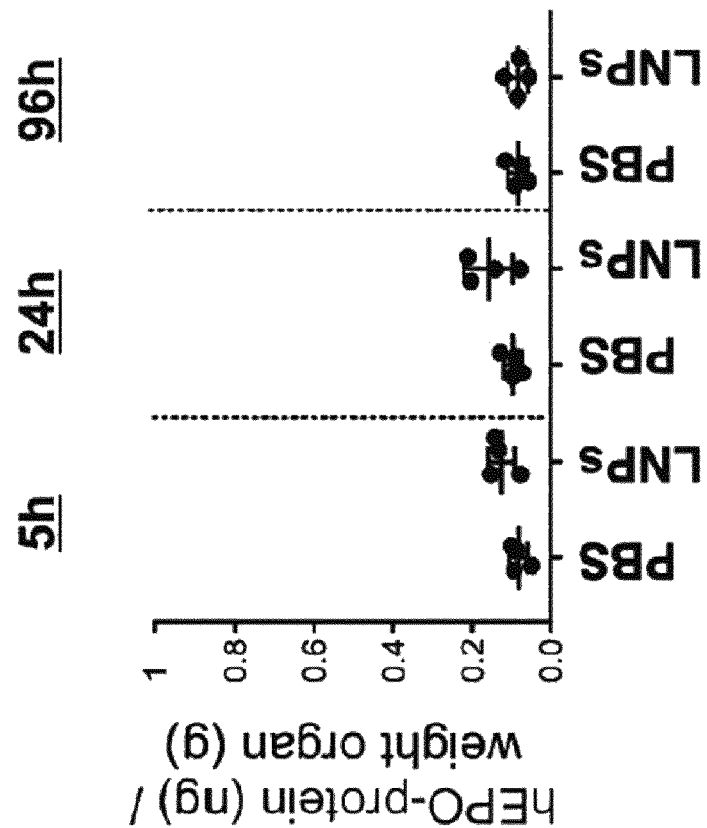
Figure 140:
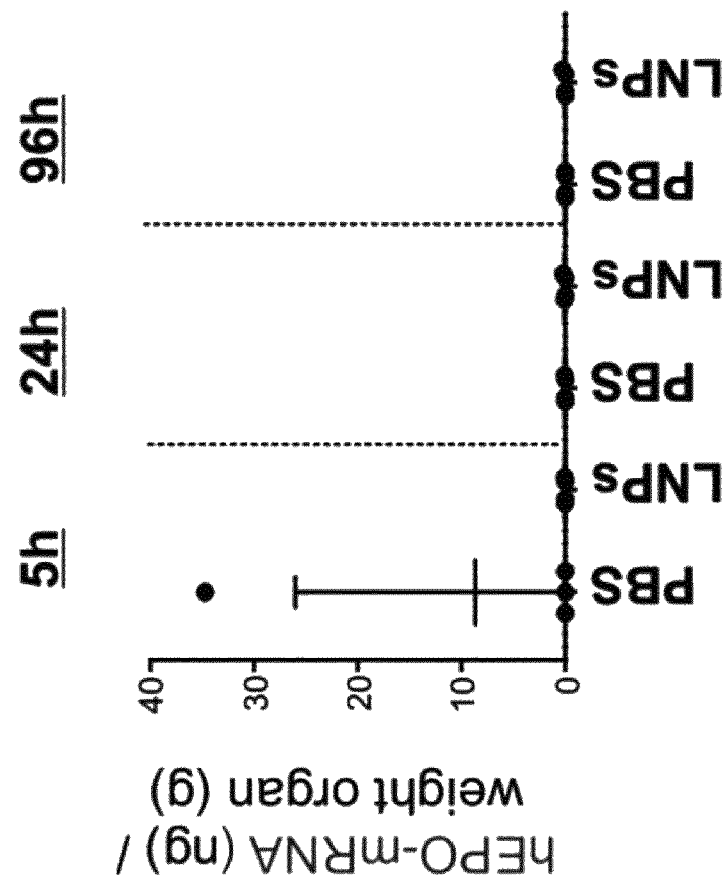
Figure 14P:
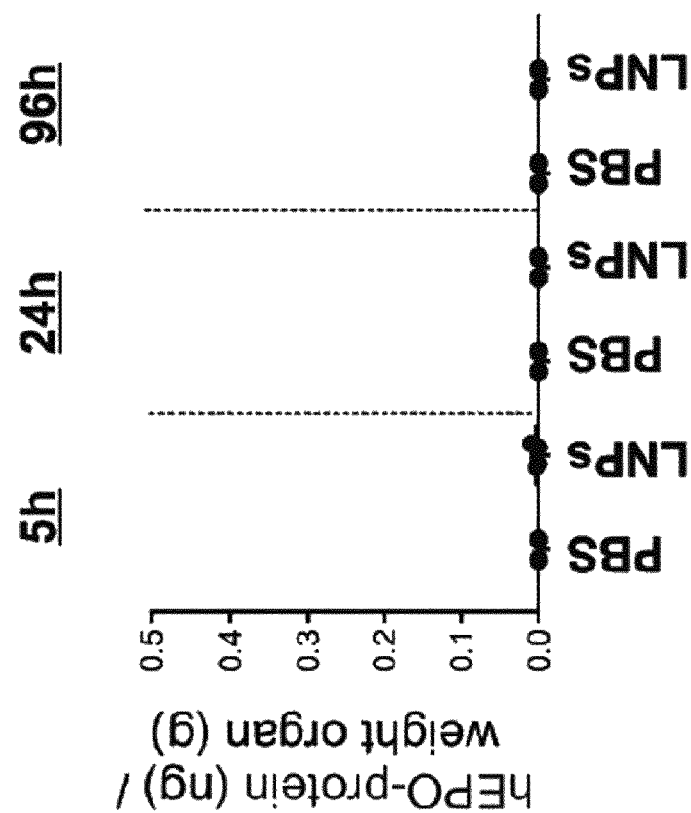
Figure 15A:
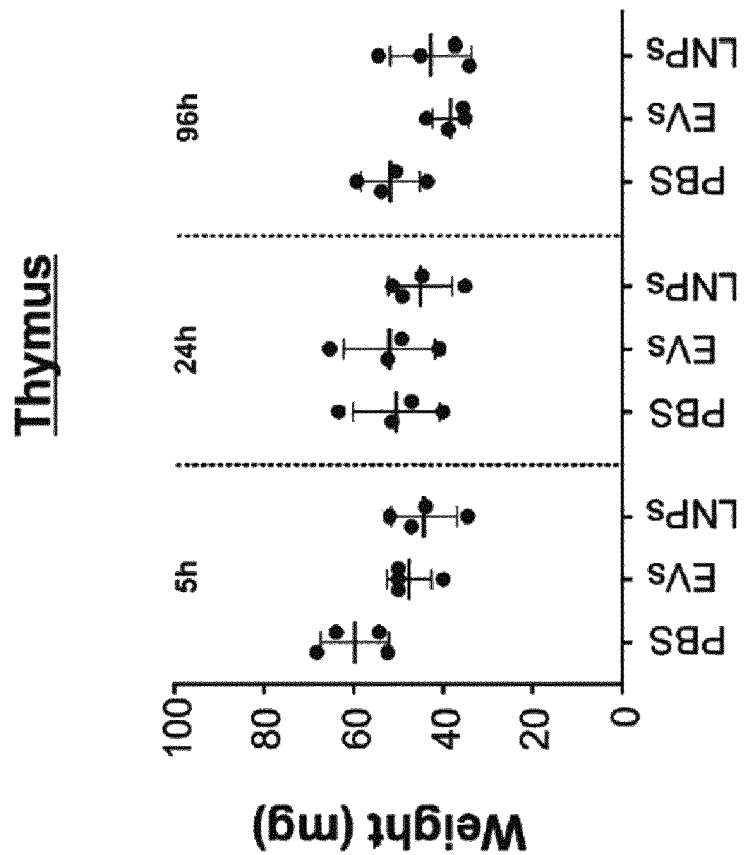
FIG. 15A-H show organ weight following in vivo delivery of human EPO mRNA via MC3-EVs or MC3-LNPs. Mice were intravenously injected with 100 μL of MC3-EVs or MC3-LNPs, containing 1.5 μg of hEPO mRNA (per mouse), or with the equivalent volume of PBS as a control. The weight of each mouse organ was determined 5 hours, 24 hours, and 96 hours after injection: thymus (FIG. 15A), kidney (FIG. 15B), heart (FIG. 15C), liver (FIG. 15D), pancreas (FIG. 15E), brain (FIG. 15F), spleen (FIG. 15G), and lung (FIG. 15H). No appreciable differences were observed between different injections (PBS, EVs, LNPs). For treated (MC3-EVs, MC3-LNPs) and untreated (PBS) groups, four mice (n=4) were used. Abbreviations: PBS—untreated mice; EVs—MC3-EVs containing hEPO mRNA; LNPs—MC3-LNPs containing hEPO mRNA. Data are shown as means with standard deviations (SD). Each dot in the scattered plot represents each replicate (mouse).
Figure 15B:
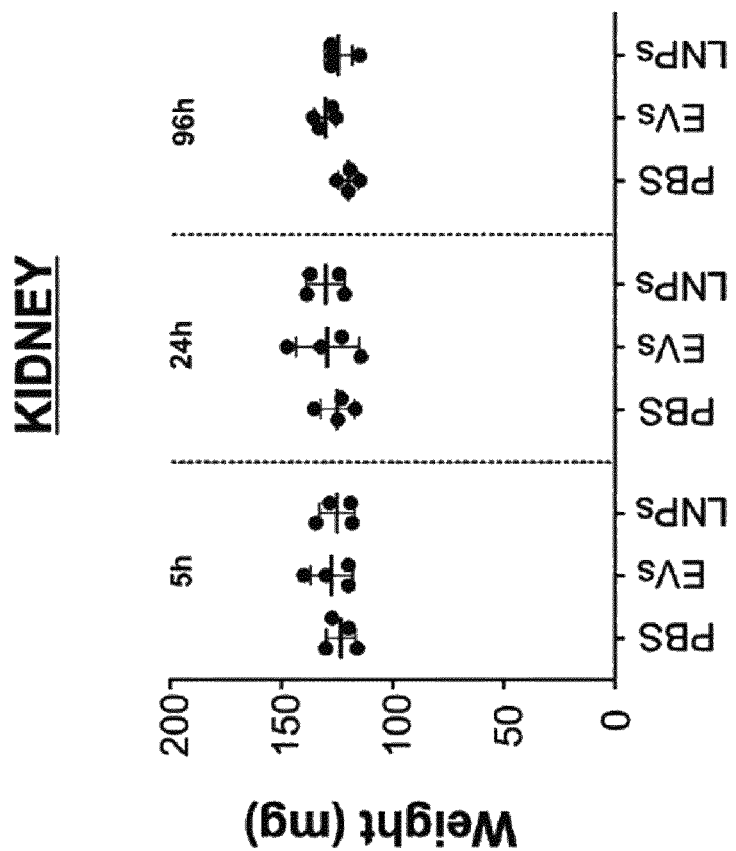
Figure 15C:
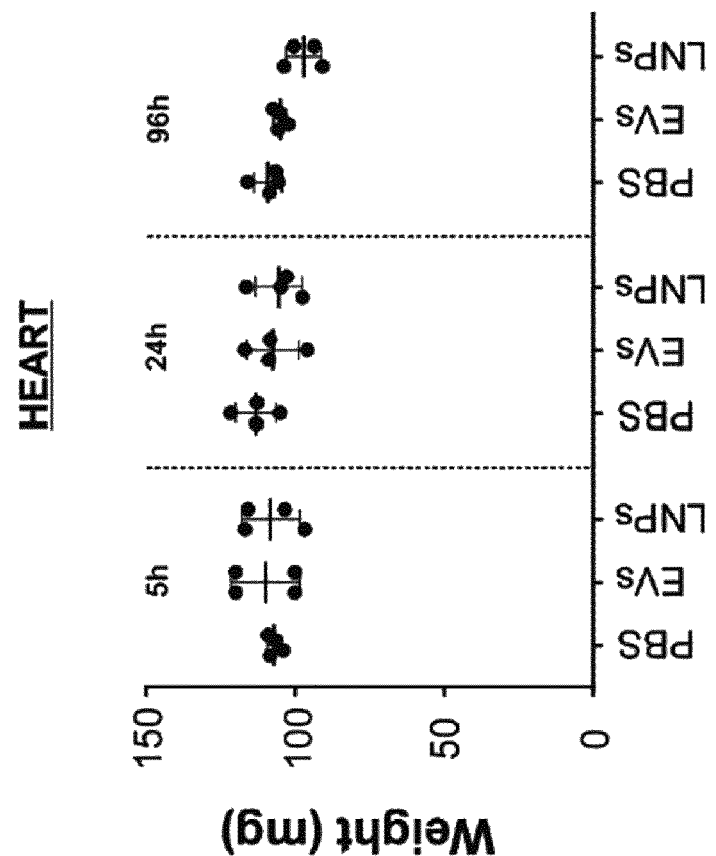
Figure 15D:
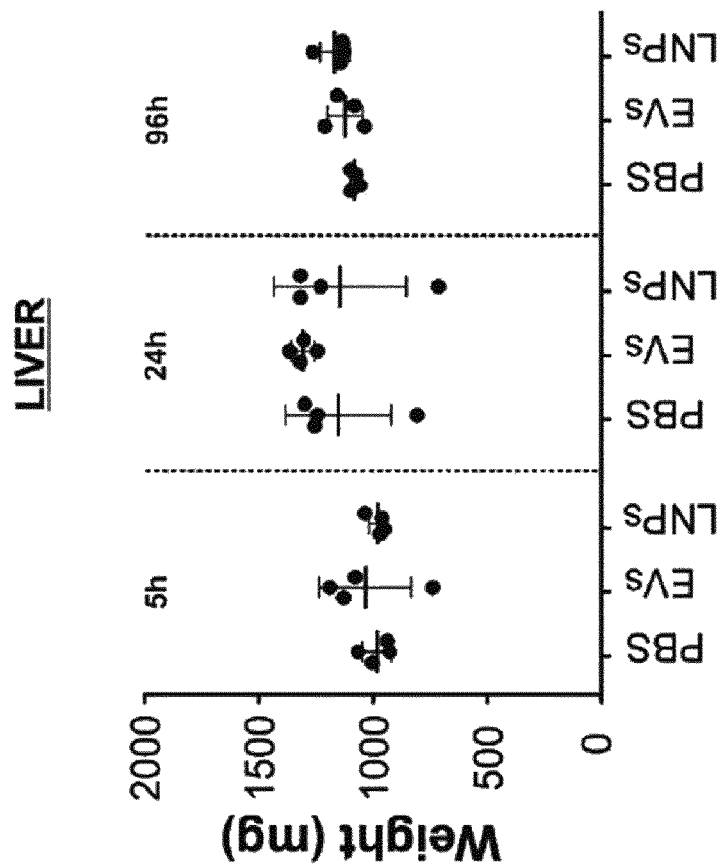
Figure 15E:
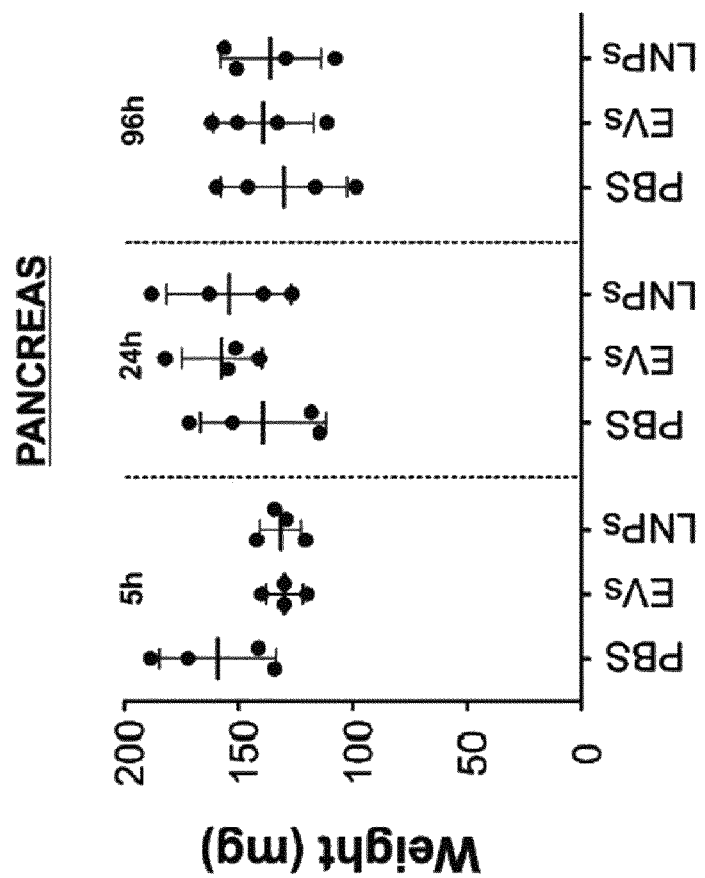
Figure 15F:
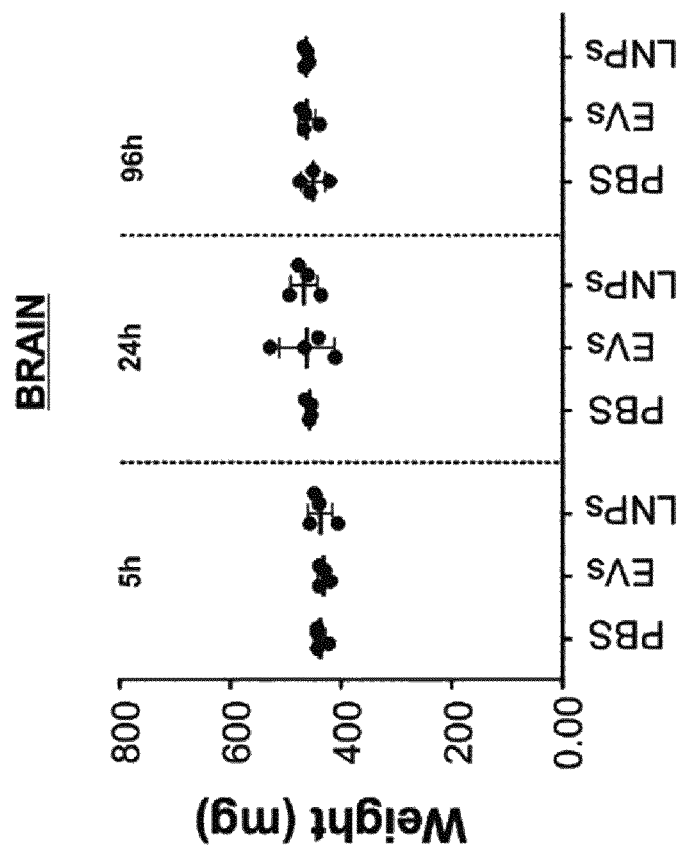
Figure 15G:
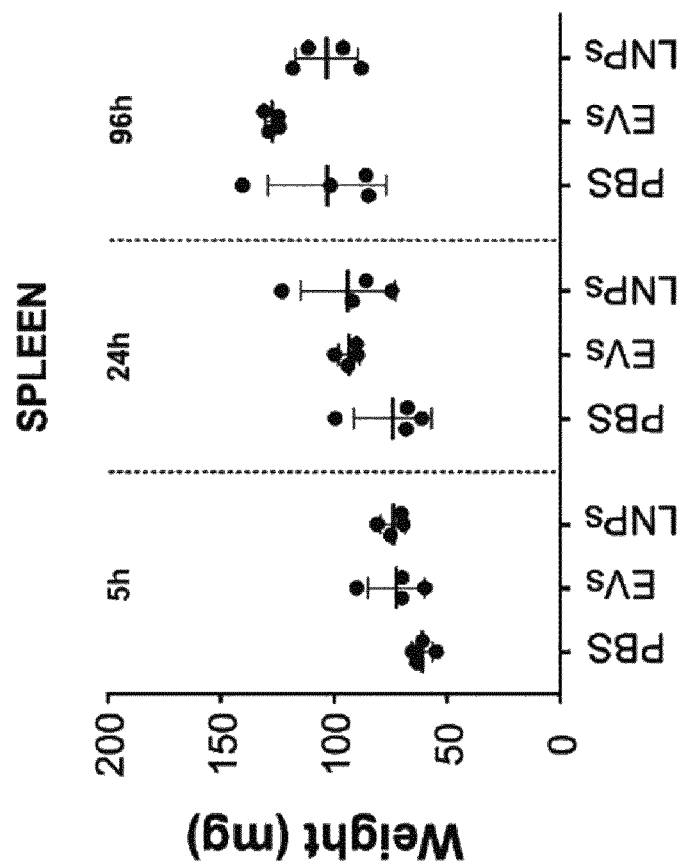
Figure 15H:
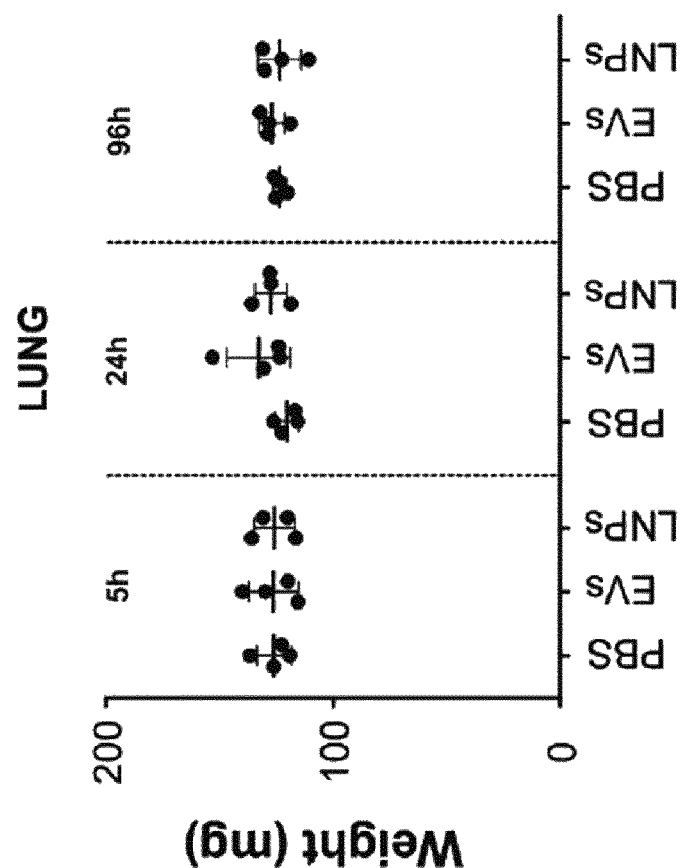

A parallel experiment was also performed with MC3-LNPs to examine LNP-mediated hEPO mRNA delivery. C57BL6/NCrl mice were injected intravenously with a single dose of MC3-LNPs (1.5 µg hEPO mRNA per mouse) and the production of hEPO protein was examined in plasma and the organs. The data show that hEPO protein was detectable in plasma after 2 hours of LNP-mediated hEPO mRNA delivery and persisted for 5 hours (FIG. 13). Additionally, the presence of hEPO mRNA and hEPO protein was analyzed in eight organs of the mice sacrificed after 5 hours, 24 hours, and 96 hours of LNPs delivery. hEPO mRNA and hEPO protein were detectable in five organs, notably heart, lung, liver, spleen, and kidney (FIG. 14A-J). Among all organs positive for hEPO mRNA and hEPO protein, the most hEPO mRNA was detected in the kidney (which persisted for 24 hours), followed by the spleen (which persisted for 96 hours). The most hEPO protein was detected in the liver. However, in the heart and lung, both hEPO mRNA and hEPO protein were detected 5 hours after injection. Thymus, pancreas, and brain were negative both for hEPO mRNA and hEPO protein (FIG. 14K-P).

Taken together, these data suggest that EVs may be used as delivery vehicles to express any protein of interest from exogenously present mRNA.

Example 6: Delivery of Human EPO mRNA to Mice Via EVs or LNPs

Figure 5:
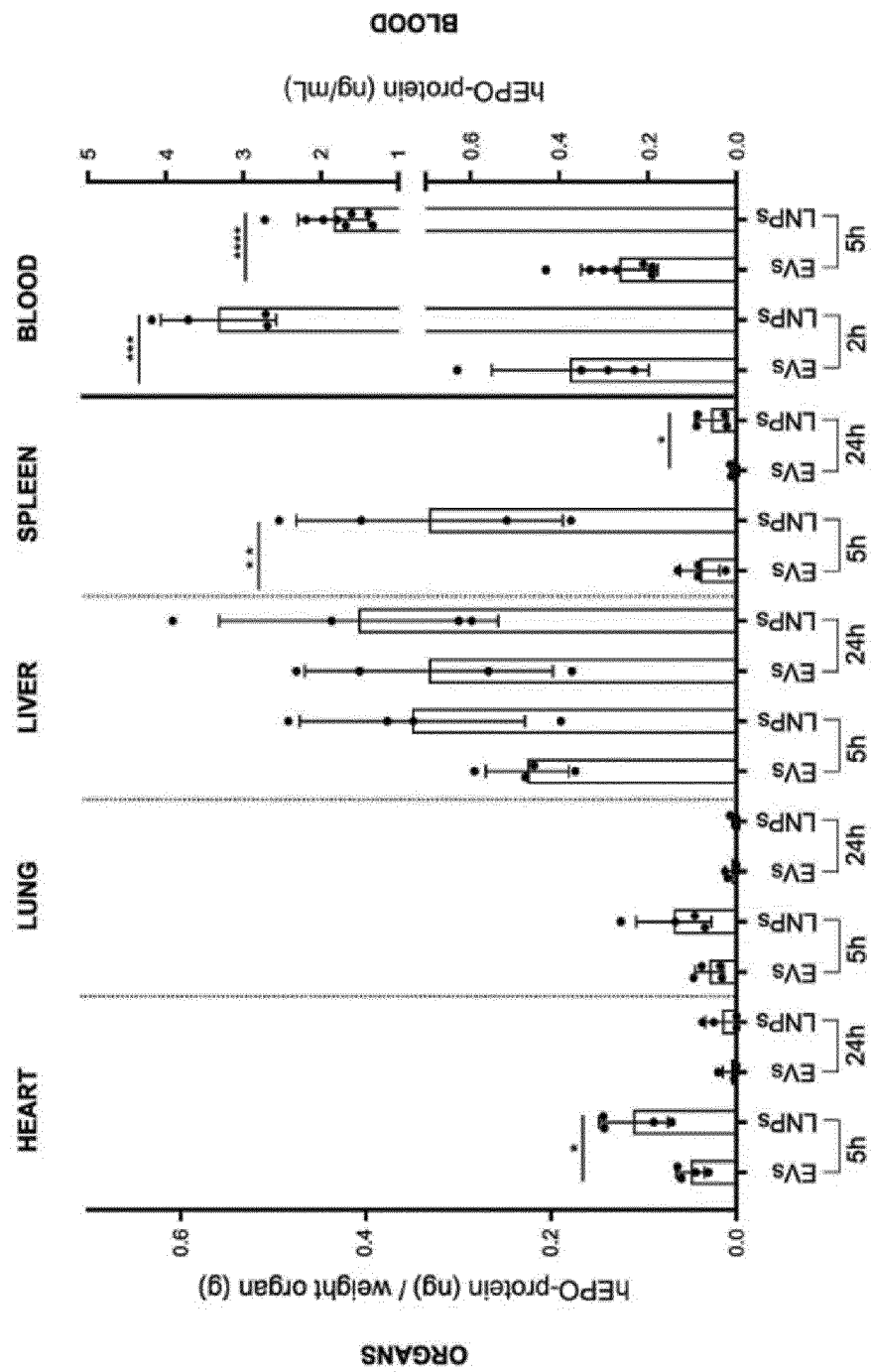
FIG. 5 shows hEPO protein levels in mouse blood and organs after MC3-EVs and MC3-LNPs delivery. MC3-EVs and MC3-LNPs were compared for the production of hEPO protein after delivering an equal dose of hEPO mRNA (1.5 µg per mouse) to mice. In organs, the amount of hEPO protein from LNPs was generally comparable to EVs except for the spleen, which showed a significant difference in protein production, followed by the heart (which showed a less significant difference in protein production). The most significant difference was observed in plasma levels of hEPO protein, which were higher following MC3-LNPs delivery as compared to MC3-EVs delivery. Data are presented as mean values with standard deviation (SD) of replicates (dots in the scattered plot represent each replicate) at each time point. EV-treated and LNP-treated groups were compared for each organ or blood plasma at each time point using a parametric unpaired two-tailed t test. Significant values are shown as P-values: *$P<0.05$, $P<0.01$, *$P<0.001$, ****$P<0.0001$.
Figure 6A:
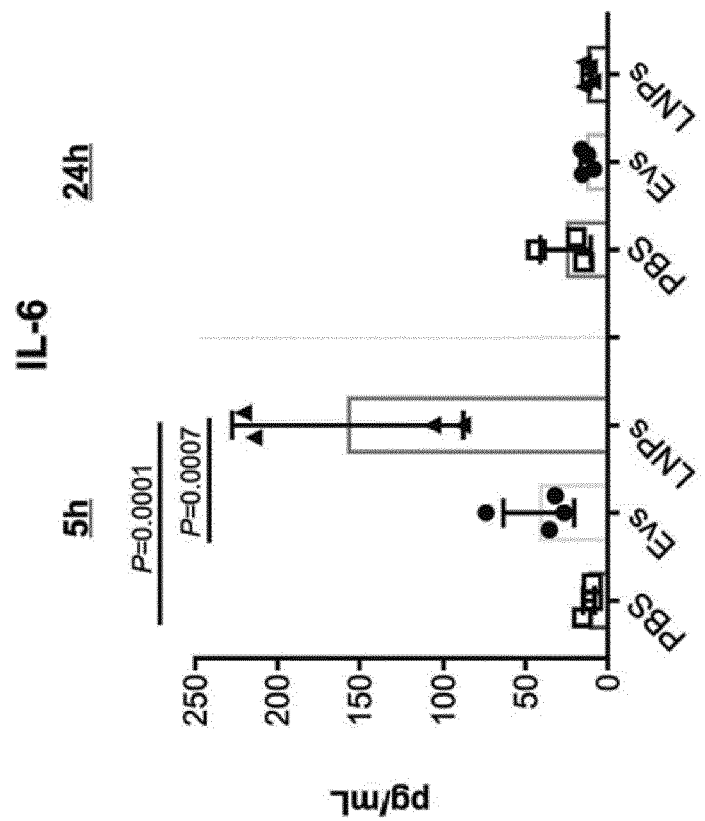
FIG. 6A shows cytokine IL-6 levels in mouse plasma after MC3-EVs and MC3-LNPs delivery. Mice were intravenously injected with 100 µL of MC3-EVs or MC3-LNPs, containing 1.5 µg of hEPO mRNA (per mouse). The concentration of IL-6 was determined in mouse plasma by MILLIPLEX® MAP Mouse Cytokine magnetic bead kit, 5 hours and 24 hours after injection of MC3-EVs, MC3-LNPs, or PBS. Data are presented from 4 mice (n=4) at each time point. Each dot in the scattered plot represents each replicate (mouse). A one-way ANOVA test was performed, followed by a Sidak's multiple comparisons test. Significant values are shown as P-values.
Figure 6B:
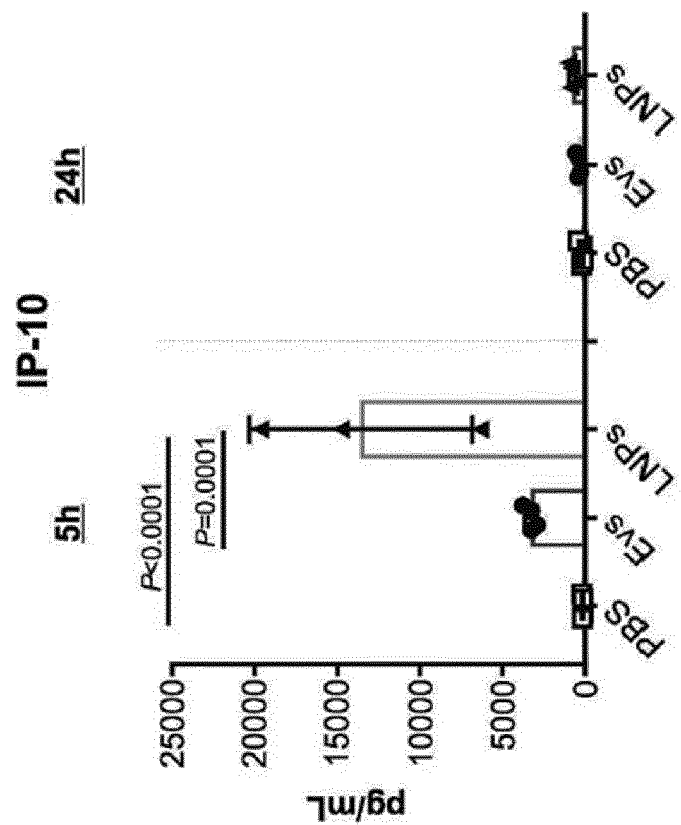
FIG. 6B shows cytokine IP-10 levels in mouse plasma after MC3-EVs and MC3-LNPs delivery. Mice were intravenously injected with 100 µL of MC3-EVs or MC3-LNPs, containing 1.5 µg of hEPO mRNA (per mouse). The concentration of IP-10 was determined in mouse plasma 5 hours and 24 hours after injection of MC3-EVs, MC3-LNPs, or PBS. Data are presented from 4 mice (n=4) at each time point. Each dot in the scattered plot represents each replicate (mouse). A one-way ANOVA test was performed, followed by a Sidak's multiple comparisons test. Significant values are shown as P-values.
Figure 6C:
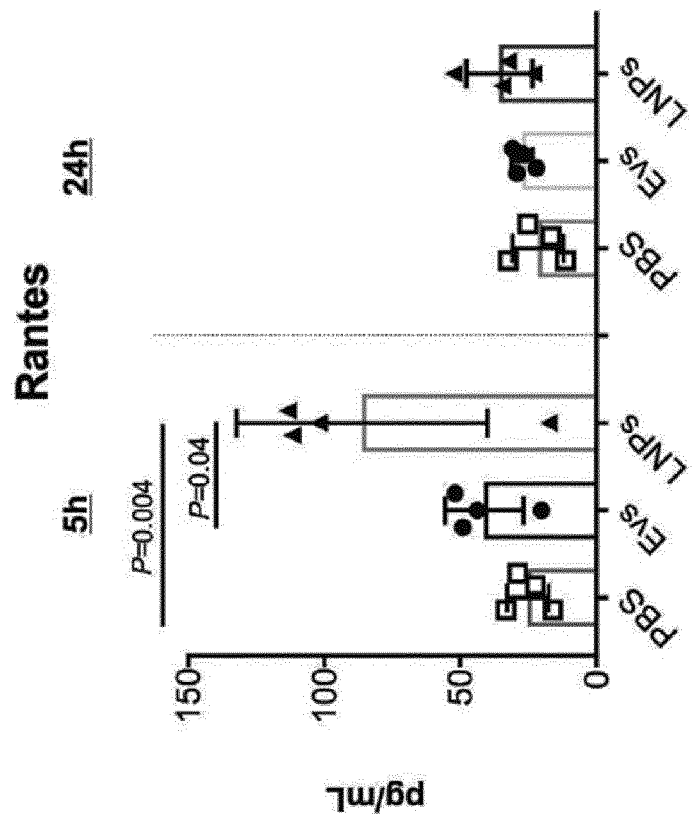
FIG. 6C shows cytokine RANTES levels in mouse plasma after MC3-EVs and MC3-LNPs delivery. Mice were intravenously injected with 100 µL of MC3-EVs or MC3-LNPs, containing 1.5 µg of hEPO mRNA (per mouse). The concentration of RANTES was determined in mouse plasma 5 hours and 24 hours after injection of MC3-EVs, MC3-LNPs, or PBS. Data are presented from 4 mice (n=4) at each time point. Each dot in the scattered plot represents each replicate (mouse). A one-way ANOVA test was performed, followed by a Sidak's multiple comparisons test. Significant values are shown as P-values.
Figure 6D:
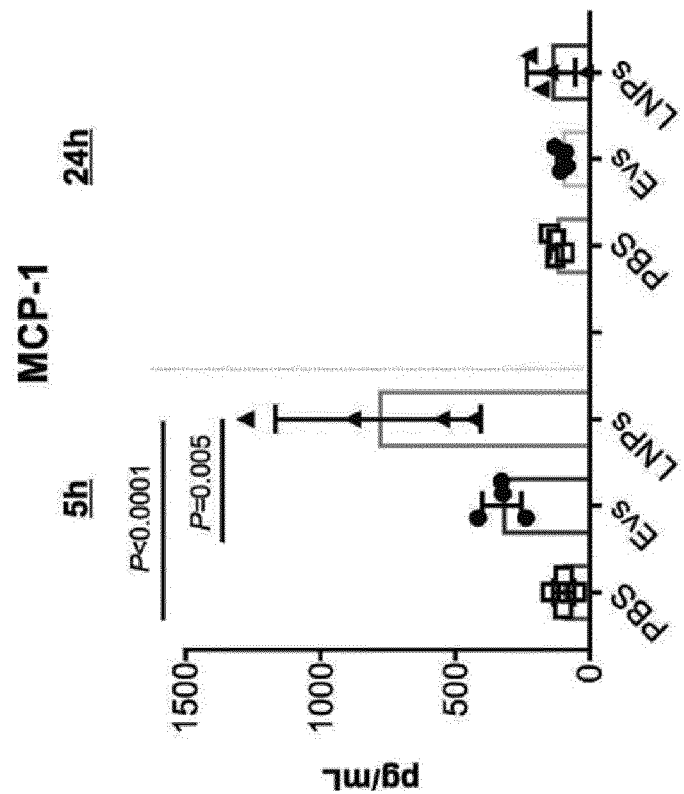
FIG. 6D shows cytokine MCP-1 levels in mouse plasma after MC3-EVs and MC3-LNPs delivery. Mice were intravenously injected with 100 µL of MC3-EVs or MC3-LNPs, containing 1.5 µg of hEPO mRNA (per mouse). The concentration of MCP-1 was determined in mouse plasma 5 hours and 24 hours after injection of MC3-EVs, MC3-LNPs, or PBS. Data are presented from 4 mice (n=4) at each time point. Each dot in the scattered plot represents each replicate (mouse). A one-way ANOVA test was performed, followed by a Sidak's multiple comparisons test. Significant values are shown as P-values.
Figure 6E:
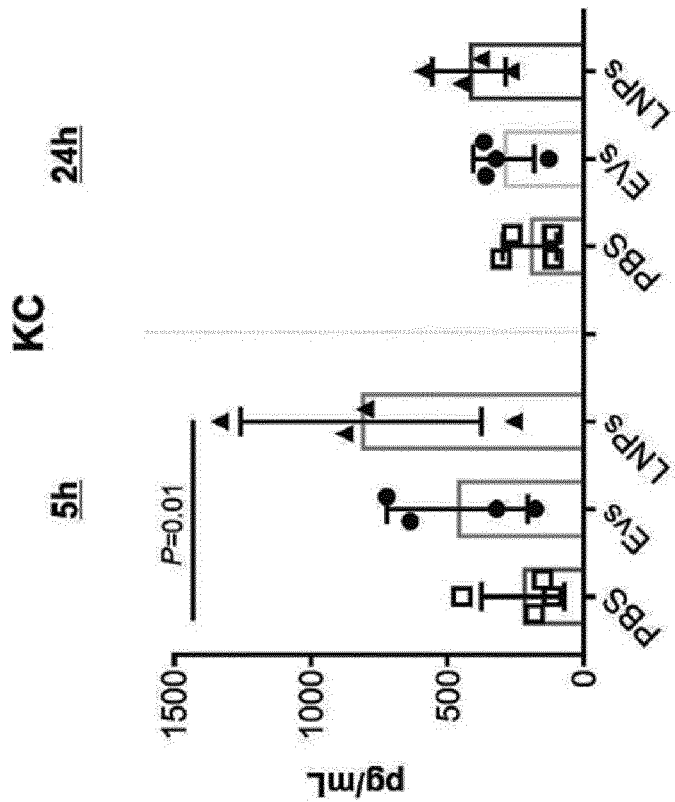
FIG. 6E shows cytokine KC levels in mouse plasma after MC3-EVs and MC3-LNPs delivery. Mice were intravenously injected with 100 µL of MC3-EVs or MC3-LNPs, containing 1.5 µg of hEPO mRNA (per mouse). The concentration of KC was determined in mouse plasma 5 hours and 24 hours after injection of MC3-EVs, MC3-LNPs, or PBS. Data are presented from 4 mice (n=4) at each time point. Each dot in the scattered plot represents each replicate (mouse). A one-way ANOVA test was performed, followed by a Sidak's multiple comparisons test. Significant values are shown as P-values.
Figure 6F:
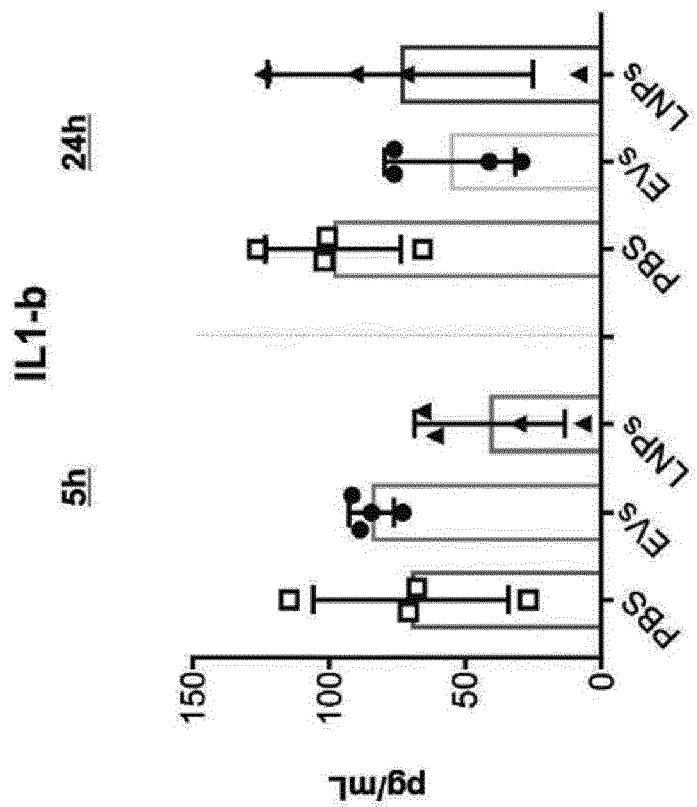
FIG. 6F shows cytokine IL1-β levels in mouse plasma after MC3-EVs and MC3-LNPs delivery. Mice were intravenously injected with 100 µL of MC3-EVs or MC3-LNPs, containing 1.5 µg of hEPO mRNA (per mouse). The concentration of IL1-β was determined in mouse plasma 5 hours and 24 hours after injection of MC3-EVs, MC3-LNPs, or PBS. Data are presented from 4 mice (n=4) at each time point. Each dot in the scattered plot represents each replicate (mouse). A one-way ANOVA test was performed, followed by a Sidak's multiple comparisons test. Significant values are shown as P-values.
Figure 6G:
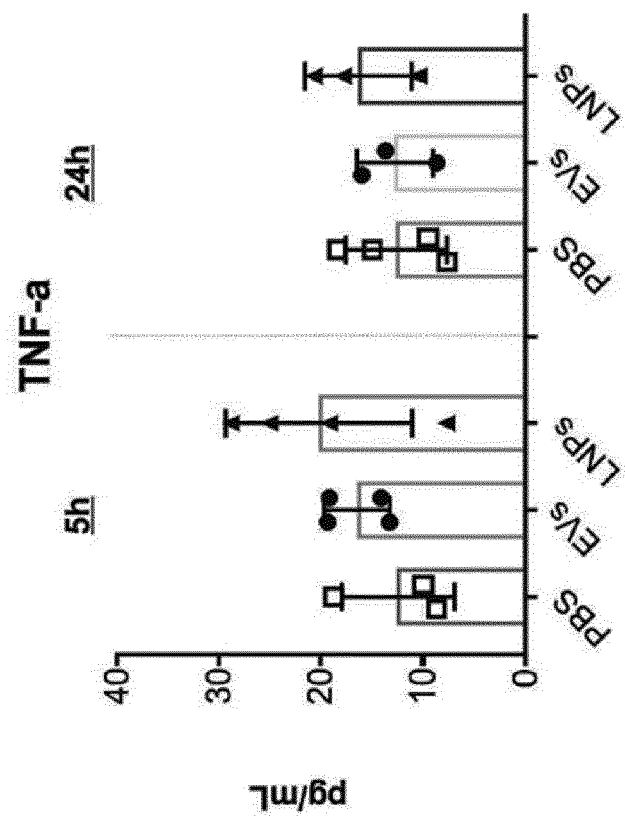
FIG. 6G shows cytokine TNF-α levels in mouse plasma after MC3-EVs and MC3-LNPs delivery. Mice were intravenously injected with 100 µL of MC3-EVs or MC3-LNPs, containing 1.5 µg of hEPO mRNA (per mouse). The concentration of TNF-α was determined in mouse plasma 5 hours and 24 hours after injection of MC3-EVs, MC3-LNPs, or PBS. Data are presented from 4 mice (n=4) at each time point. Each dot in the scattered plot represents each replicate (mouse). A one-way ANOVA test was performed, followed by a Sidak's multiple comparisons test. Significant values are shown as P-values.
Figure 6H:
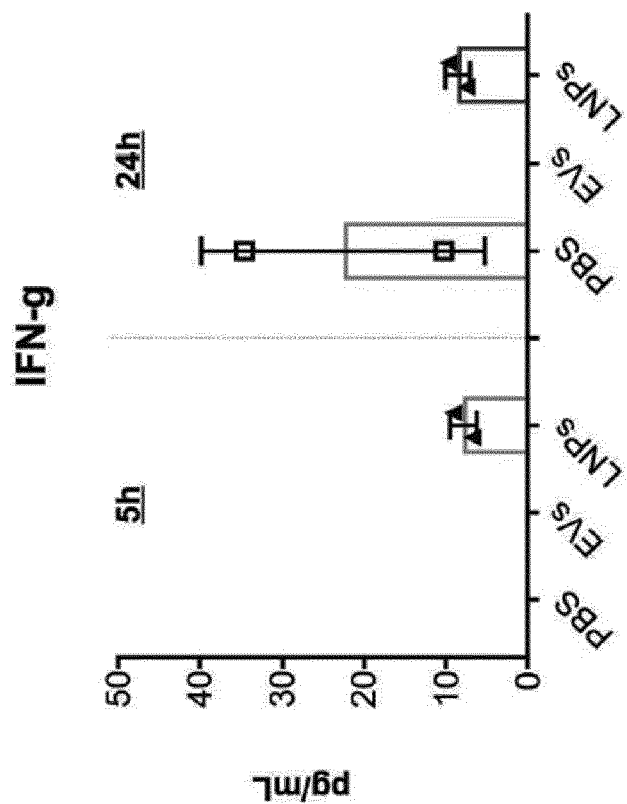
FIG. 6H shows cytokine IFN-γ levels in mouse plasma after MC3-EVs and MC3-LNPs delivery. Mice were intravenously injected with 100 µL of MC3-EVs or MC3-LNPs, containing 1.5 µg of hEPO mRNA (per mouse). The concentration of IFN-γ was determined in mouse plasma 5 hours and 24 hours after injection of MC3-EVs, MC3-LNPs, or PBS. Data are presented from 4 mice (n=4) at each time point. Each dot in the scattered plot represents each replicate (mouse). A one-way ANOVA test was performed, followed by a Sidak's multiple comparisons test. Significant values are shown as P-values.
Figure 7A:
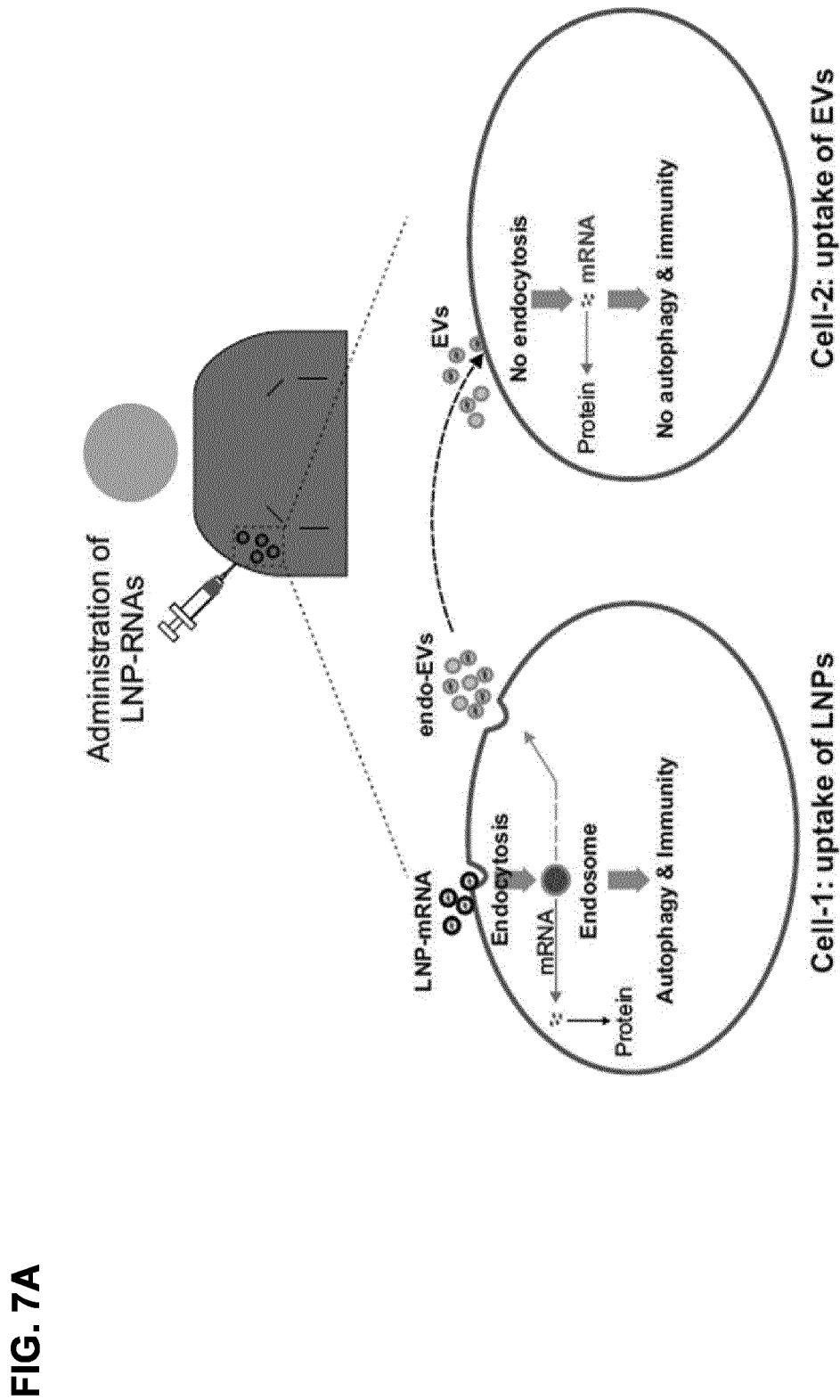
FIG. 7A shows an exemplary schematic of the hypothetical fate of LNPs in humans.
Figure 7B:
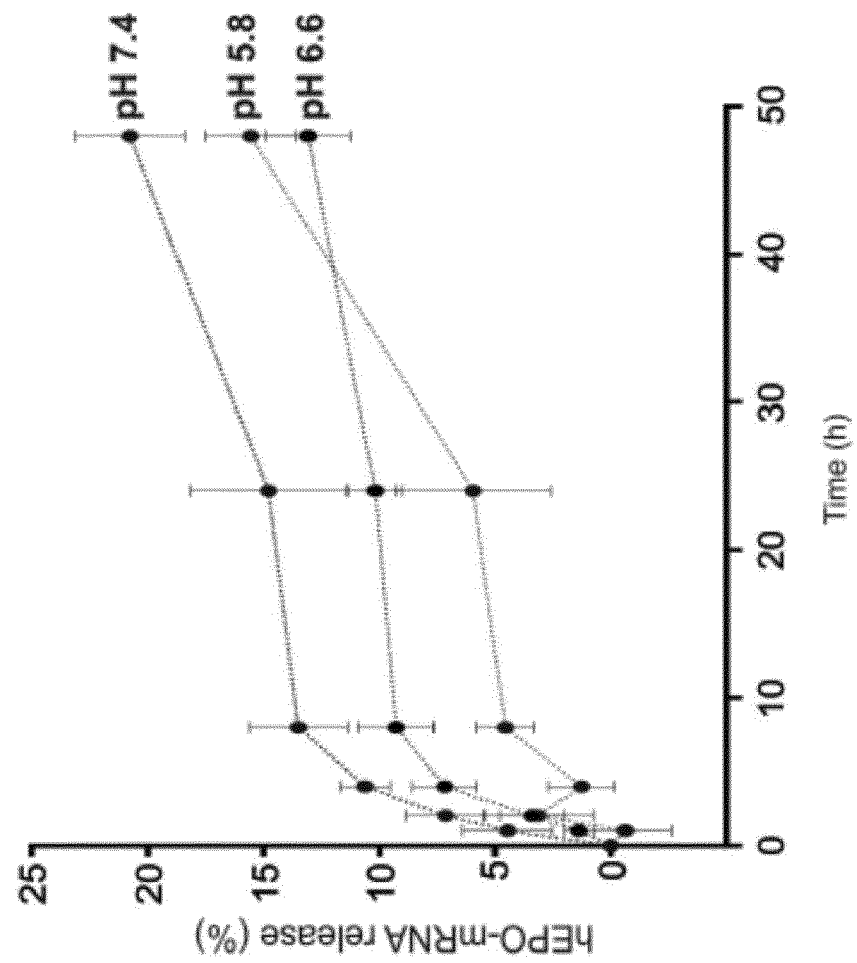
FIG. 7B shows hEPO mRNA is not released from LNPs in an acidic environment (pH 5.8 or 6.6). In contrast, at physiological pH (7.4), the hEPO mRNA and lipid components of LNPs dissociate.
Figure 7C:
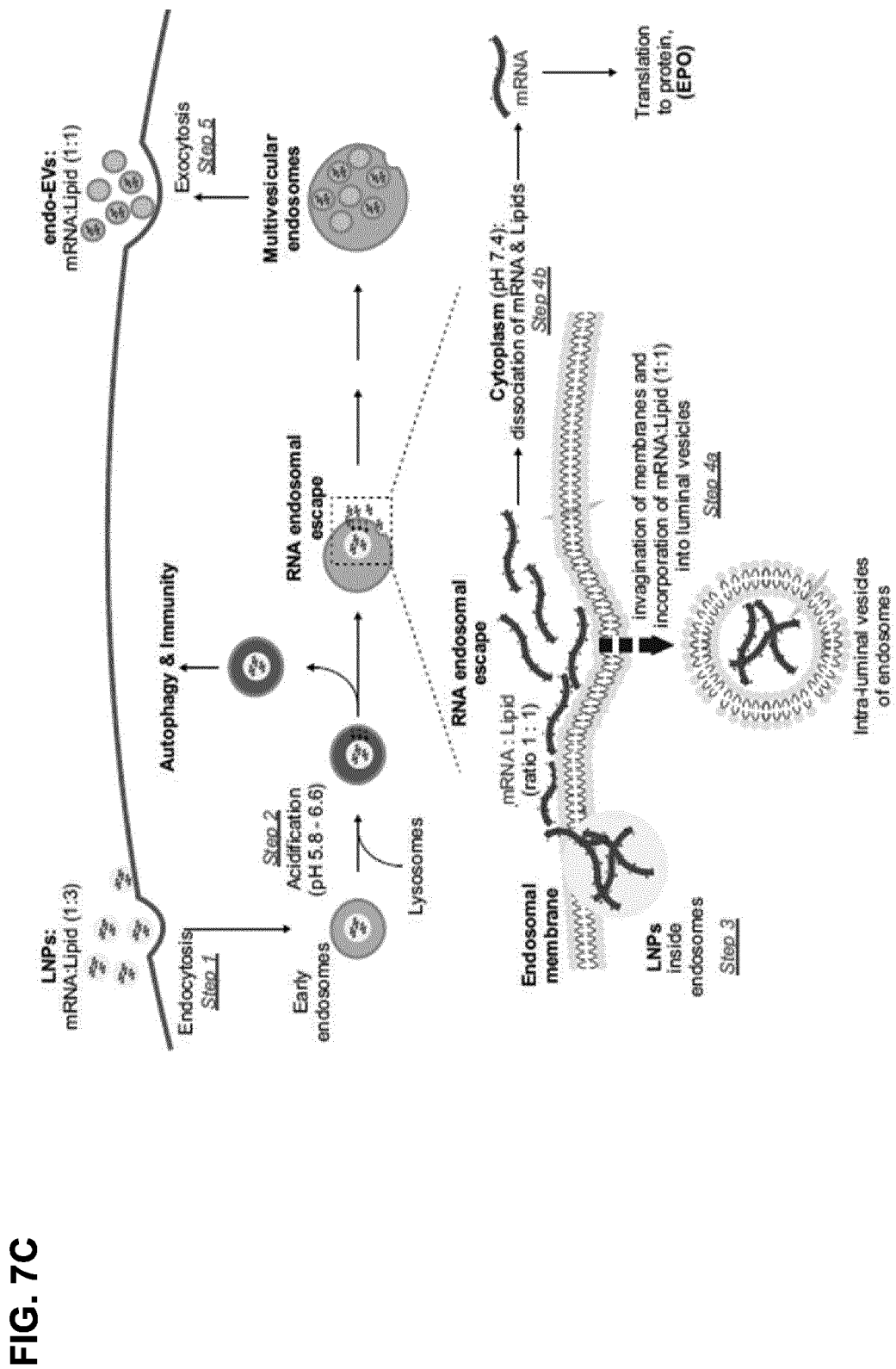
FIG. 7C shows an exemplary schematic of the hypothetical fate of LNP-endosomes.

To determine how efficiently EVs deliver hEPO mRNA relative to MC3-LNPs, the production of hEPO protein was compared following LNP- and EV-based hEPO mRNA delivery in vivo. In organs, the amount of hEPO protein from LNP-based hEPO mRNA delivery was generally comparable to EVs with the exception of the spleen, which showed a significant difference in protein production followed by the heart (with less significant difference) (FIG. 5). The amount of hEPO protein in the blood was higher for LNP delivery compared to EVs (FIG. 5). Additionally, the effect of MC3-LNPs and MC3-EVs on tissue weight was examined. MC3-LNPs and MC3-EVs showed no significant effect on organ weight in recipient mice (FIG. 15A-H).

Example 7: EVs Elicit a Reduced Immune/Inflammatory Response Relative to LNPs To investigate whether EVs are less immunogenic to recipient mice as compared to LNPs, single doses of MC3-LNPs (1.5 µg hEPO mRNA per mouse) and MC3-EVs (1.5 µg hEPO mRNA per mouse) were injected intravenously into C57BL6/NCrl mice. Concentrations of 8 different cytokines generally involved in immune and inflammatory responses were determined in the mouse plasma at two time intervals (5 hours and 24 hours). The secreted levels of several pro-inflammatory cytokines (notably IL-6, IP-10, RANTES, MCP-1, and KC) detected 5 hours after injection were significantly higher following LNPs delivery than following EVs delivery (FIG. 6A-E).

These results indicate that the systemic delivery of LNPs can elicit elevated inflammatory responses, whereas EVs are less immunogenic and appear to be well tolerated by recipient mice. Although LNPs may result in more hEPO protein production than EVs (FIG. 5), LNPs may be more immunogenic than EVs, potentially making EVs safer vehicles for delivery of therapeutic RNAs to human patients.

Figure 17A:
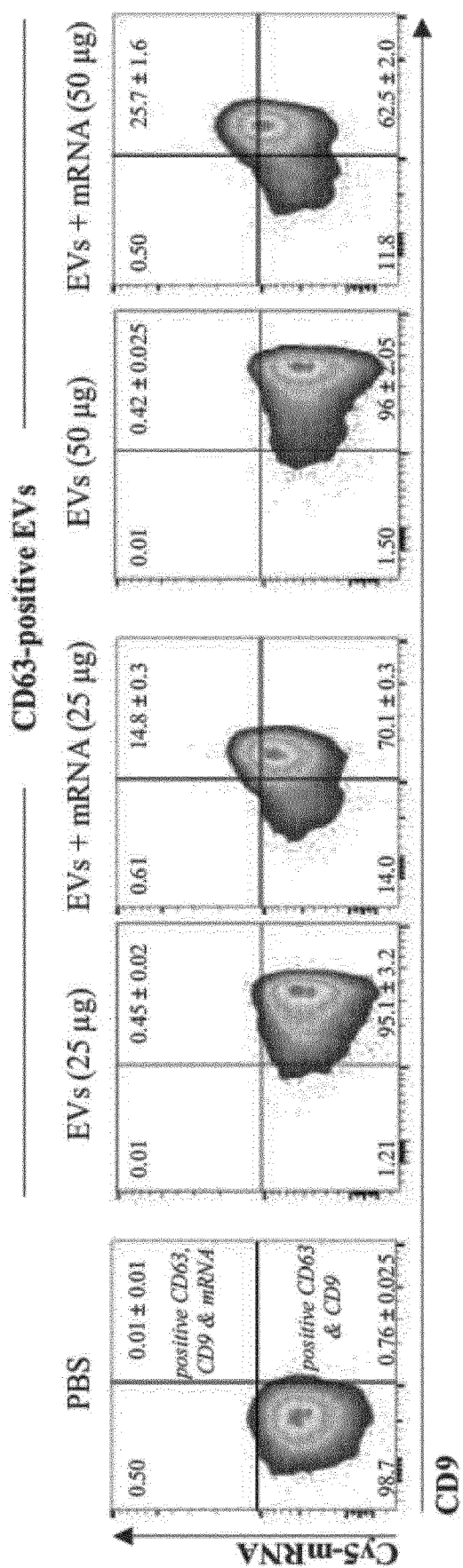
FIG. 17A and FIG. 17B show the characterization of EVs derived from LNP treated cells.

Example 8: Detection of EV Markers and Foreign mRNA in CD63/CD9 Positive EVs To confirm that LNP-mRNA is carried by EVs, HTB-177 cells were treated with or without MC3-LNPs containing 100 µg of Cy5-mRNA. After 96 hours, total EVs were isolated from the culturing medium of LNP treated cells (MC3-EVs) and untreated cells (EVs) by differential ultracentrifugation, resuspended in PBS, and quantified. 25 µg or 50 µg of total MC3-EVs or total untreated EVs were incubated with 20 µL paramagnetic Dynabeads conjugated with anti-CD63 antibody and CD63 positive EVs were specifically isolated using an Exosome-Human CD63 Isolation/Detection kit (Thermo Fisher Scientific). CD63 positive EVs were then stained with a mouse anti-human PE-CD9 antibody (BD Pharmingen, Cat. No. 555372) and analyzed by FACS for Cy5-mRNA detection. FACS analysis showed that approximately 96% of immunoprecipitated EVs (50 µg assay) from untreated cells were positive for CD63 and CD9, but negative for the mRNA. In contrast, approximately 88% of immunoprecipitated EVs (50 µg assay) from LNP-mRNA treated cells were positive for CD63 and CD9, and 26% contain mRNA (Cy5-mRNA) secreted after the endocytosis of LNPs containing Cy5-mRNA (FIG. 17A). In the negative controls (only beads and CD63/CD9 positive EVs derived from untreated cells), no Cy5-mRNA signal was detected, suggesting that mRNA is carried by EVs (CD63/CD9 positive EVs).

Example 9: EV-mRNA Protection Assay

Figure 17B:
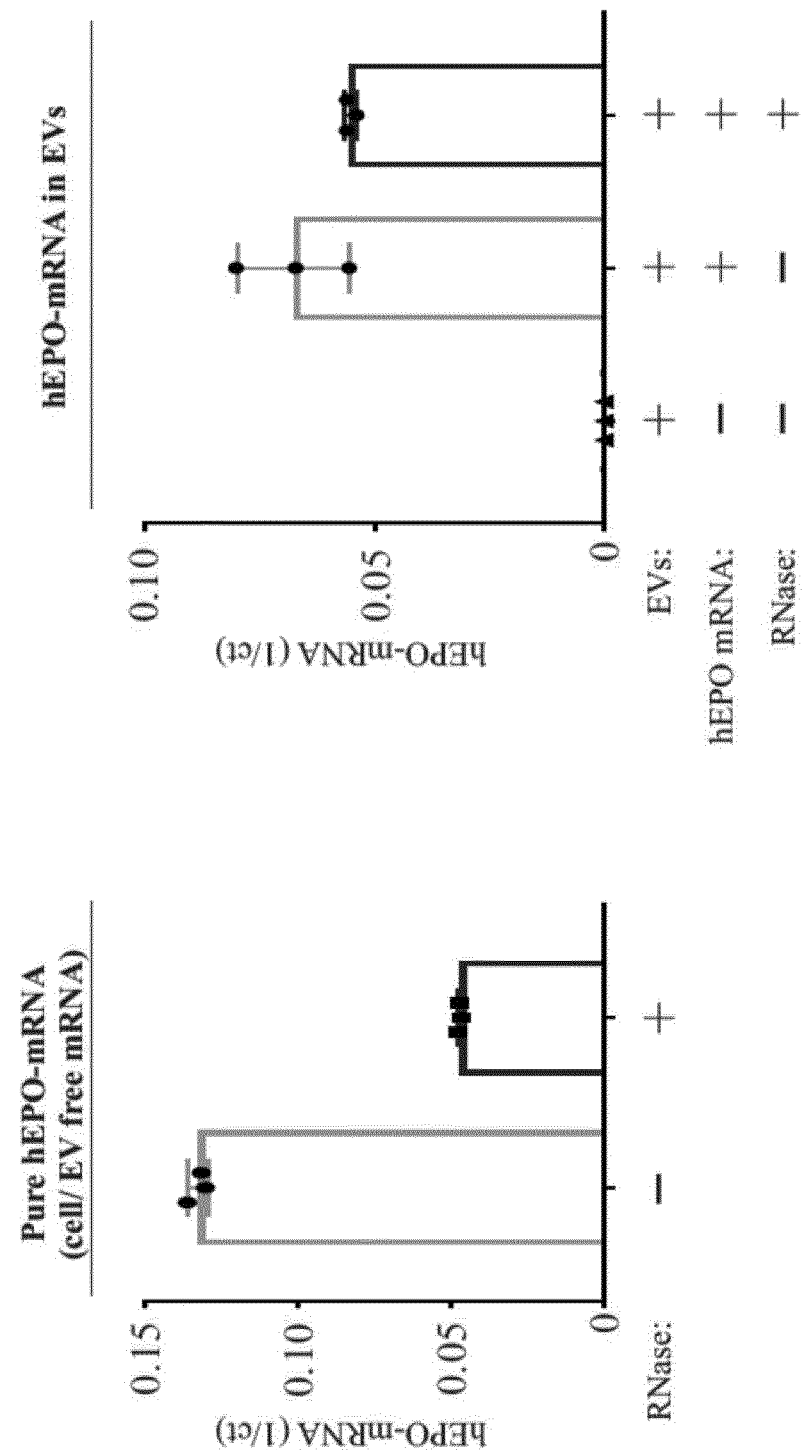

To confirm that mRNA is located and protected inside EVs rather than associated with EV membranes, MC3-EVs containing hEPO mRNA were exposed to RNase treatment. Total RNA was isolated from EVs after RNase treatment and hEPO mRNA was quantified by qPCR. Despite the efficient endonucleolytic activity of the RNase (shown on EV free RNA), only a 2 Ct fold-change decrease in hEPO mRNA content was observed in the RNase treated MC3-EVs as compared to the MC3-EVs not treated with RNase. The experiment was performed in three biological replicates (n=3) and the hEPO mRNA qPCR data are represented as a scatter dot plot and mean standard deviation (SD) (FIG. 17B). EVs derived from untreated cells, without RNase treatment, were used as a negative control. Although a small portion of the delivered mRNA could potentially be attached to the external membrane layer of the EVs, most hEPO mRNA was found to be protected from endonucleolytic activity and present within EVs.

The invention claimed is:

1. An isolated exosome comprising a modified ribonucleic acid (RNA) prepared by a process comprising:
   (a) providing one or more lipid nanoparticles (LNP) comprising the modified RNA;
   (b) contacting one or more cells with the LNP under conditions that allow LNP uptake by the one or more cells; and
   (c) isolating exosomes produced by the one or more cells, wherein at least one isolated exosome comprises the modified RNA;
   wherein the exosome comprises an ionizable lipid:modified RNA nucleotides molar ratio of about 1:1 to about 3:1, or less than about 1:1.

2. The isolated exosome of claim 1, wherein the LNP comprises at least one ionizable lipid, phospholipid, structural lipid, and/or PEG lipid, wherein the PEG lipid comprises a lipid portion and a polyethylene glycol portion.

3. The isolated exosome of claim 1, wherein the LNP comprises an ionizable lipid that is dilinoleylmethyl-4-dimethylaminobutyrate (DLin-MC3-DMA) or 1,2-dilinoleyloxy-3-dimethylaminopropane (DLin-DMA), a phospholipid that is 1,2-distearoyl-sn-glycero-3-phosphocholine (DSPC), a structural lipid that is cholesterol, and/or a PEG lipid that is PEG-DMPE or PEG2000-DMPE.

4. The isolated exosome of claim 1, wherein the LNP comprises an ionizable lipid:modified RNA nucleotides molar ratio of about 2:1 to about 4:1.

5. The isolated exosome of claim 1, wherein the exosome comprises at least one ionizable lipid, phospholipid, structural lipid, and/or PEG lipid.

6. The isolated exosome of claim 1, wherein the exosome comprises an ionizable lipid:modified RNA nucleotides molar ratio of about 3:1, about 2:1, about 1:1, or less than about 1:1.

7. The isolated exosome of claim 1, wherein the exosome comprises an ionizable lipid:modified RNA nucleotides molar ratio of about 1:1 or less than about 1:1.

8. The isolated exosome of claim 1, wherein the exosome comprises an ionizable lipid:modified RNA nucleotides molar ratio that is less than the ionizable lipid:modified RNA nucleotides molar ratio comprised by the LNP.

9. The isolated exosome of claim 1, wherein the one or more cells are is obtained from a subject.

10. The isolated exosome of claim 1, wherein the one or more cells are is an epithelial cells, immune cells, progenitor cells, or stem cells.

11. The isolated exosome of claim 1, wherein the process is performed in vitro.

12. The isolated exosome of claim 1, wherein isolating exosomes comprises isolating exosomes from a sample of in vitro cell culture medium.

13. A pharmaceutical composition comprising at least one isolated exosome of claim 1, and a pharmaceutically acceptable carrier.

14. A method of treating or preventing a disorder in a subject, comprising administering to the subject an effective amount of the isolated exosomes of claim 1, wherein the isolated exosomes comprise a modified RNA effective to treat the disorder.

15. The method of claim 14, wherein the subject has a reduced immune and/or inflammatory response to treatment in the presence of an isolated exosome as compared to treatment in the absence of an isolated exosome.

16. The method of claim 14, wherein the isolated exosomes are isolated from a cell obtained from the subject.

* * * * *

SEQUENCE LISTING

<160> NUMBER OF SEQ ID NOS: 3

<210> SEQ ID NO 1
<211> LENGTH: 193
<212> TYPE: PRT
<213> ORGANISM: Homo sapiens
<220> FEATURE:
<223> OTHER INFORMATION: Human erythropoietin (protein)

<400> SEQUENCE: 1

```
Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg
```

<210> SEQ ID NO 2
<211> LENGTH: 1340
<212> TYPE: RNA
<213> ORGANISM: Artificial Sequence
<220> FEATURE:
<223> OTHER INFORMATION: Human erythropoietin (mRNA)

<400> SEQUENCE: 2

```
cccggagccg daccggggcc accgcgcccg ctctgctccg acaccgcgcc ccctggacag      60
ccgccctctc ctccaggccc gtggggctgg ccctgcaccg ccgagcttcc cgggatgagg     120
gcccccggtg tggtcacccg cgcgcccca ggtcgctgag gaccccggc caggcgcgga      180 gatgggggtg cacgaatgtc ctgcctggct gtggcttctc ctgtccctgc tgtcgctccc      240
tctgggcctc ccagtcctgg gcgccccacc acgcctcatc tgtgacagcc gagtcctgga      300
gaggtacctc ttggaggcca aggaggccga gaatatcacg acgggctgtg ctgaacactg      360
cagcttgaat gagaatatca ctgtcccaga caccaaagtt aatttctatg cctggaagag      420
gatggaggtc gggcagcagg ccgtagaagt ctgcagggc ctggccctgc tgtcggaagc      480
tgtcctgcgg ggccaggccc tgttggtcaa ctcttcccag ccgtgggagc cctgcagct      540 gcatgtggat aaagccgtca gtggccttcg cagcctcacc actctgcttc gggctctggg      600
```

-continued

```
agcccagaag gaagccatct cccctccaga tgcggcctca gctgctccac tccgaacaat        660
cactgctgac actttccgca aactcttccg agtctactcc aatttcctcc ggggaaagct        720
gaagctgtac acaggggagg cctgcaggac aggggacaga tgaccaggtg tgtccacctg        780
ggcatatcca ccacctccct caccaacatt gcttgtgcca caccctcccc cgccactcct        840 gaacccgtc gaggggctct cagctcagcg ccagcctgtc ccatggacac tccagtgcca         900
gcaatgacat ctcaggggcc agaggaactg tccagagagc aactctgaga tctaaggatg        960
tcacagggcc aacttgaggg cccagagcag gaagcattca gagagcagct ttaaactcag        1020
ggacagagcc atgctgggaa gacgcctgag ctcactcggc accctgcaaa atttgatgcc        1080
aggacacgct ttggaggcga tttacctgtt ttcgcaccta ccatcaggga caggatgacc        1140
tggataactt aggtggcaag ctgtgacttc tccaggtctc acgggcatgg gcactccctt        1200
ggtggcaaga gccccttga caccggggtg gtgggaacca tgaagacagg atgggggctg        1260
gcctctggct ctcatggggt ccaagttttg tgtattcttc aacctcattg acaagaactg        1320
aaaccaccaa aaaaaaaaa                                                    1340

<210> SEQ ID NO 3
<211> LENGTH: 582
<212> TYPE: RNA
<213> ORGANISM: Artificial Sequence
<220> FEATURE:
<223> OTHER INFORMATION: Human erythropoietin (mRNA, coding region)

<400> SEQUENCE: 3
atgggggtgc acgaatgtcc tgcctggctg tggcttctcc tgtccctgct gtcgctccct         60
ctgggcctcc cagtcctggg cgccccacca cgcctcatct gtgacagccg agtcctggag        120
aggtacctct tggaggccaa ggaggccgag aatatcacga cgggctgtgc tgaacactgc        180
agcttgaatg agaatatcac tgtcccagac accaaagtta atttctatgc ctggaagagg        240
atggaggtcg ggcagcaggc cgtagaagtc tggcagggcc tggccctgct gtcggaagct        300
gtcctgcggg gccaggccct gttggtcaac tcttcccagc cgtggagcc ctgcagctg         360 catgtggata aagccgtcag tggccttcgc agccctcacca ctctgcttcg ggctctggga        420
gcccagaagg aagccatctc ccctccagat gcggcctcag ctgctccact ccgaacaatc        480
actgctgaca ctttccgcaa actcttccga gtctactcca atttcctccg gggaaagctg        540
aagctgtaca caggggaggc ctgcaggaca ggggacagat ga                          582
```